(12) United States Patent
Molnar

(10) Patent No.: US 10,653,307 B2
(45) Date of Patent: May 19, 2020

(54) MEDICAL DEVICES FOR AIRWAY MANAGEMENT AND METHODS OF PLACEMENT

(71) Applicant: WM & DG, Inc., Deerfield, IL (US)

(72) Inventor: Robert W. Molnar, Long Grove, IL (US)

(73) Assignee: WM & DG, INC., Deerfield, IL (US)

( * ) Notice: Subject to any disclaimer, the term of this patent is extended or adjusted under 35 U.S.C. 154(b) by 0 days.

(21) Appl. No.: 16/416,592

(22) Filed: May 20, 2019

(65) Prior Publication Data

US 2020/0113427 A1 Apr. 16, 2020

Related U.S. Application Data

(63) Continuation-in-part of application No. 16/156,322, filed on Oct. 10, 2018.

(51) Int. Cl.
*A61B 1/267* (2006.01)
*A61M 16/04* (2006.01)
(Continued)

(52) U.S. Cl.
CPC ............... *A61B 1/267* (2013.01); *A61B 1/04* (2013.01); *A61B 1/0676* (2013.01);
(Continued)

(58) Field of Classification Search
CPC ... A61B 17/2673; A61B 17/2676; A61B 1/04; A61B 1/0676; A61M 16/04;
(Continued)

(56) References Cited

U.S. PATENT DOCUMENTS 4,231,365 A 11/1980 Scarberry
4,360,008 A 11/1982 Corazzelli, Jr.
(Continued)

FOREIGN PATENT DOCUMENTS

EP 0665029 A2 8/1995
KR 20120095385 8/2012
(Continued)

OTHER PUBLICATIONS

Bledsoe B., "The Disappearing Endotrachael Tube"., Clinical Professor of Emergency Medicine, University of Nevada School of Medicine, 2009, 84 pages.
(Continued)

*Primary Examiner* — Matthew J Lawson
(74) *Attorney, Agent, or Firm* — Greer, Burns & Crain, Ltd.

(57) ABSTRACT

Oral airway devices having a tubal body curved anteriorly and comprising a central lumen and one or more peripheral hollow passages for hosting a camera and/or one or more tools including a gastric suction tube, including oral airway devices in which the tubal body ends with a tongue and the wall of the tubal body encircles a central lumen. Oral airway devices also include those which comprise three channels, two of which are peripheral channels located in the flanks of the wall of the tubal body, the oral airway devices being compatible with a laryngoscope. Methods for ventilating, intubating and extubating a patient with the medical devices.

18 Claims, 41 Drawing Sheets

(51) Int. Cl.
    *A61B 1/04* (2006.01)
    *A61B 1/06* (2006.01)
    *A61B 90/00* (2016.01)

(52) U.S. Cl.
    CPC .... *A61M 16/0402* (2014.02); *A61M 16/0434* (2013.01); *A61M 16/0488* (2013.01); *A61B 90/361* (2016.02)

(58) Field of Classification Search
    CPC ........ A61M 16/0402; A61M 16/07404; A61M 16/0434; A61M 16/0463; A61M 16/0488
    See application file for complete search history.

(56) References Cited

U.S. PATENT DOCUMENTS

| | | |
|---|---|---|
| 4,577,638 A | 3/1986 | Graham |
| 4,584,998 A | 4/1986 | McGrail |
| 4,607,643 A | 8/1986 | Bell et al. |
| 4,846,153 A | 7/1989 | Berci |
| 5,052,386 A | 1/1991 | Fischer, Jr. |
| 5,025,778 A | 6/1991 | Silverstein et al. |
| 5,174,283 A | 12/1992 | Parker |
| 5,193,692 A | 3/1993 | Farley et al. |
| 5,241,956 A | 9/1993 | Brain |
| 5,353,787 A | 10/1994 | Price |
| 5,372,131 A | 12/1994 | Heinen, Jr. |
| 5,400,771 A | 3/1995 | Pirak et al. |
| 5,499,625 A | 3/1996 | Frass et al. |
| 5,511,916 A | 4/1996 | Farley et al. |
| 5,513,627 A | 5/1996 | Flam |
| 5,515,844 A | 5/1996 | Christopher |
| 5,551,947 A | 9/1996 | Kaali |
| 5,632,271 A | 5/1997 | Brain |
| 5,665,052 A | 9/1997 | Bullard |
| 5,682,880 A | 11/1997 | Brain |
| 5,733,242 A | 3/1998 | Rayburn et al. |
| 5,740,791 A | 4/1998 | Aves |
| 5,819,733 A | 10/1998 | Bertram |
| 5,879,306 A | 3/1999 | Fontenot et al. |
| 5,888,195 A | 3/1999 | Schneider |
| 6,038,629 A | 3/2000 | Ogilvie et al. |
| 6,115,523 A | 9/2000 | Choi et al. |
| 6,142,144 A | 11/2000 | Pacey |
| 6,189,533 B1 | 2/2001 | Simon et al. |
| 6,196,225 B1 | 3/2001 | Allgeyer |
| 6,349,720 B1 | 2/2002 | Clark |
| 6,386,199 B1 | 5/2002 | Alfery |
| 6,439,232 B1 | 8/2002 | Brain |
| 6,440,061 B1 | 8/2002 | Wenner et al. |
| 6,443,156 B1 | 9/2002 | Niklason et al. |
| 6,527,704 B1 | 3/2003 | Chang et al. |
| 6,543,447 B2 | 4/2003 | Pacey |
| 6,626,169 B2 | 9/2003 | Gaitini |
| 6,631,720 B1 | 10/2003 | Brain |
| 6,634,354 B2 | 10/2003 | Christopher |
| 6,655,377 B2 | 12/2003 | Pacey |
| 6,860,264 B2 | 3/2005 | Christopher |
| 6,860,270 B2 | 3/2005 | Sniadach |
| 6,918,391 B1 | 7/2005 | Moore |
| 7,052,456 B2 | 5/2006 | Simon |
| 7,128,509 B2 | 10/2006 | Farley et al. |
| 7,156,091 B2 | 1/2007 | Koyama et al. |
| 7,237,993 B2 | 7/2007 | Farley et al. |
| 7,331,925 B2 | 2/2008 | McMorrow et al. |
| 7,421,877 B2 | 9/2008 | Frenken |
| 7,450,746 B2 | 11/2008 | Yang et al. |
| 1,493,901 A1 | 2/2009 | Brain |
| 7,520,857 B2 | 4/2009 | Chalana et al. |
| 7,527,601 B2 | 5/2009 | Dubey et al. |
| 7,611,466 B2 | 11/2009 | Chalana et al. |
| 7,654,970 B2 | 2/2010 | Dubey |
| D611,138 S | 3/2010 | Nasir |
| D615,188 S | 3/2010 | Nasir |
| 7,713,189 B2 | 5/2010 | Hanke |
| 7,713,216 B2 | 5/2010 | Dubey et al. |
| 7,727,150 B2 | 6/2010 | Chalana et al. |
| 7,744,534 B2 | 6/2010 | Chalana et al. |
| 7,749,165 B2 | 7/2010 | McMorrow et al. |
| 7,749,176 B2 | 7/2010 | Dubey |
| 7,806,119 B2 | 10/2010 | Nasir |
| 7,811,239 B2 | 10/2010 | Dubey et al. |
| 7,819,806 B2 | 10/2010 | Yang et al. |
| 7,854,324 B2 | 12/2010 | Farley et al. |
| 7,896,007 B2 | 3/2011 | Brain |
| 7,921,847 B2 | 4/2011 | Totz |
| 7,942,813 B2 | 5/2011 | Mackin |
| 7,976,458 B2 | 7/2011 | Stefanchik et al. |
| 8,016,760 B2 | 9/2011 | Chalana et al. |
| 8,038,629 B2 | 10/2011 | Solanki et al. |
| 8,202,215 B2 | 6/2012 | Xiao et al. |
| 8,215,307 B2 | 7/2012 | Nasir |
| 8,297,275 B2 | 10/2012 | Ogilvie et al. |
| 8,308,644 B2 | 11/2012 | McMorrow et al. |
| 8,371,303 B2 | 2/2013 | Schaner et al. |
| 8,529,442 B2 | 9/2013 | Pacey et al. |
| 8,677,990 B2 | 3/2014 | Gabriel |
| 8,863,746 B2 | 10/2014 | Totz |
| 8,928,746 B1 | 1/2015 | Stevrin et al. |
| 9,211,060 B2 | 12/2015 | Waldron et al. |
| 9,415,179 B2 | 8/2016 | Molnar |
| 9,427,142 B2 | 8/2016 | Terliuc |
| 9,579,012 B2 | 2/2017 | Vazales et al. |
| 9,833,587 B2 | 12/2017 | Cook |
| 10,213,567 B1 | 2/2019 | Theventhiran |
| 10,342,944 B2 | 7/2019 | Molnar |
| 2002/0108610 A1 | 8/2002 | Christopher |
| 2002/0195103 A1 | 12/2002 | O'Mara |
| 2003/0220542 A1 | 11/2003 | Belson et al. |
| 2004/0230136 A1 | 11/2004 | Corrigan, Jr. |
| 2004/0258249 A1 | 12/2004 | Niederdrank et al. |
| 2005/0182297 A1 | 8/2005 | Gravenstein et al. |
| 2005/0228226 A1 | 10/2005 | Muckner |
| 2005/0244801 A1 | 11/2005 | DeSalvo |
| 2005/0268917 A1 | 12/2005 | Boedeker et al. |
| 2006/0004260 A1 | 1/2006 | Boedeker et al. |
| 2006/0032505 A1 | 2/2006 | Alfery et al. |
| 2006/0111633 A1 | 5/2006 | McMorrow et al. |
| 2006/0149129 A1 | 7/2006 | Watts et al. |
| 2006/0162730 A1 | 7/2006 | Glassenberg et al. |
| 2006/0167375 A1 | 7/2006 | Terrassse et al. |
| 2006/0180155 A1 | 8/2006 | Glassenberg et al. |
| 2006/0276694 A1 | 12/2006 | Acha Gandarias |
| 2007/0095351 A1 | 5/2007 | Gobel |
| 2007/0106121 A1 | 5/2007 | Yokota et al. |
| 2007/0137651 A1 | 7/2007 | Glassenberg et al. |
| 2007/0156068 A1 | 7/2007 | Dubey |
| 2007/0175482 A1 | 8/2007 | Kimmel et al. |
| 2007/0180887 A1 | 8/2007 | Frenken |
| 2007/0203393 A1 | 8/2007 | Stefanchik |
| 2007/0239197 A1 | 10/2007 | Dubey |
| 2007/0255185 A1 | 11/2007 | Dubey |
| 2008/0029100 A1 | 2/2008 | Glassenberg et al. |
| 2008/0076989 A1 | 3/2008 | Hete et al. |
| 2008/0114268 A1 | 5/2008 | Dubey |
| 2008/0115783 A1 | 5/2008 | Brain |
| 2008/0146879 A1 | 6/2008 | Pacey |
| 2008/0188774 A1 | 8/2008 | Dubey |
| 2008/0221391 A1 | 9/2008 | Weitzner et al. |
| 2008/0276932 A1* | 11/2008 | Bassoul ............... A61M 16/04 128/200.26 |
| 2008/0287834 A1 | 11/2008 | Pusch |
| 2009/0088596 A1 | 4/2009 | Yaegashi |
| 2009/0090356 A1* | 4/2009 | Cook .................. A61M 16/04 128/200.26 |
| 2009/0105600 A1 | 4/2009 | Marks et al. |
| 2009/0177044 A1 | 7/2009 | Cohen et al. |
| 2009/0194102 A1 | 8/2009 | Chen et al. |
| 2009/0194114 A1 | 8/2009 | Chen et al. |
| 2009/0227835 A1 | 9/2009 | Terliuc |
| 2010/0051024 A1 | 3/2010 | Abrons |
| 2010/0056879 A1 | 3/2010 | Greenspan et al. |
| 2010/0056906 A1 | 3/2010 | Van Der Brug |
| 2010/0113916 A1 | 5/2010 | Kumar |

(56) References Cited

U.S. PATENT DOCUMENTS

| | | | |
|---|---|---|---|
| 2010/0147309 A1 | 6/2010 | Cuevas et al. | |
| 2010/0204546 A1 | 8/2010 | Hassidov et al. | |
| 2010/0249639 A1 | 9/2010 | Bhatt | |
| 2010/0261967 A1 | 10/2010 | Pacey et al. | |
| 2010/0312069 A1 | 12/2010 | Sutherland et al. | |
| 2011/0030694 A1 | 2/2011 | Schaner et al. | |
| 2011/0130632 A1 | 6/2011 | McGrail et al. | |
| 2011/0137127 A1 | 6/2011 | Schwartz et al. | |
| 2011/0178372 A1* | 7/2011 | Pacey | A61B 1/00142 600/188 |
| 2011/0201882 A1 | 8/2011 | Schwartz et al. | |
| 2011/0315147 A1 | 12/2011 | Wood et al. | |
| 2012/0059223 A1 | 3/2012 | McGrath et al. | |
| 2012/0259173 A1 | 10/2012 | Waldron et al. | |
| 2012/0260921 A1 | 10/2012 | Sangwan | |
| 2012/0302833 A1 | 11/2012 | Hayman et al. | |
| 2013/0006051 A1 | 1/2013 | Stace et al. | |
| 2013/0030249 A1 | 1/2013 | Vazales et al. | |
| 2013/0096379 A1 | 4/2013 | Golbert | |
| 2013/0109918 A1 | 5/2013 | Pagan | |
| 2013/0158351 A1 | 6/2013 | Daher et al. | |
| 2013/0197303 A1 | 8/2013 | Chun | |
| 2013/0253368 A1 | 9/2013 | Are et al. | |
| 2013/0324798 A1* | 12/2013 | Molnar | A61M 16/04 600/120 |
| 2014/0018626 A1 | 1/2014 | Lee | |
| 2014/0073853 A1 | 3/2014 | Swisher et al. | |
| 2014/0076309 A1* | 3/2014 | Takeda | A61M 16/0434 128/200.26 |
| 2014/0096766 A1* | 4/2014 | Avitsian | A61B 1/00135 128/200.26 |
| 2014/0166020 A1 | 6/2014 | Chang | |
| 2014/0194694 A1 | 7/2014 | Chen | |
| 2014/0323806 A1 | 10/2014 | Brain | |
| 2014/0338826 A1 | 11/2014 | Nasir | |
| 2014/0357951 A1 | 12/2014 | Muller et al. | |
| 2015/0122251 A1 | 5/2015 | Azhir et al. | |
| 2016/0038008 A1 | 2/2016 | Molnar | |
| 2016/0038014 A1 | 2/2016 | Molnar | |
| 2016/0262603 A1 | 9/2016 | Molnar | |
| 2016/0317768 A1 | 11/2016 | Nasir et al. | |
| 2016/0331918 A1 | 11/2016 | Nasir et al. | |
| 2016/0345803 A1 | 12/2016 | Mallory et al. | |
| 2016/0346493 A1 | 12/2016 | Wight | |
| 2017/0072154 A1 | 3/2017 | Hoftman et al. | |
| 2017/0196445 A1* | 7/2017 | Gardner | A61M 16/0445 |
| 2017/0209022 A1 | 7/2017 | Molnar | |
| 2017/0216544 A1* | 8/2017 | Baska | A61M 16/045 |
| 2018/0104427 A1* | 4/2018 | Avitsian | A61M 16/0434 |
| 2018/0169365 A1* | 6/2018 | Sawyer | A61M 16/0488 |
| 2019/0059710 A1* | 2/2019 | Molnar | A61B 1/05 |

FOREIGN PATENT DOCUMENTS

| | | |
|---|---|---|
| WO | WO9405200 | 3/1994 |
| WO | 03/084719 A2 | 10/2003 |
| WO | 2003084719 | 10/2003 |
| WO | 2008123934 A1 | 10/2008 |
| WO | 2009025843 A1 | 2/2009 |
| WO | WO2010120950 | 10/2010 |
| WO | 2012/080293 A2 | 6/2012 |
| WO | 2013/017535 A2 | 2/2013 |
| WO | 2015013172 | 1/2015 |
| WO | WO2016022759 A1 | 2/2016 |

OTHER PUBLICATIONS

Bledso B., "Incubation Threatened by New Devices and Lack of Paramedic Practice", Patient Care, Jems.com; http://www.jems.com/article/patient-care/incubation-threatened-new-devi, printed Feb. 21, 2015, 8 pages.

Bledso B., "Incubation Threatened by New Devices and Lack of Paramedic Practice", Patient Care; http://www.jems.com/article/patient-care/intubation-threatened-new-devi, printed Mar. 20, 2015, 14 pages.

Genzwuerker, MD. et al. "Laryngeal tube: a review of current literature" AJA-Online.com 2011:vol. 12, p. 22-33.

Kodali MD, "Capnography in emergency medicine-911" http://www.capnography.com/outside/922.htm., printed Feb. 21, 2015, 9 pages.

ETView Medical, Ltd., Announces the Appointment of David Amar, MD to Its Scientific Advisory Board, 2012; http://finance.yahoo.com/news/etview-medical-ltd-announces-appointment-104300770.html, Jun. 4, 2012, 3 pages.

Etview, "VivaSight-DL disposable dual lumen airway ventilation tube with integrated high resolution airway imaging system permitting airway control and lung isolation", http://www.etview.com/index_old.php, Jun. 21, 2012. 1 page.

"How to Use a Jem Endotrachael Tube Changer," Endotrachael Tube Changers, Instrumentatio Industries, Inc., Bethal Park, PA, 2015, 2 pages.

ETView Medical Ltd., "ETView Medical, Ltd., Announces Exclusive Patent License Agreement—Feb. 2, 2012", http://worldnetdaily.com.uk/markets/news/read/20671060/etview_medical, Jul. 5, 2012, 3 pages.

Kapoor et al., "Comparison of supraglottic devices i-gel® and LMA Fastrach® as conduit for endotracheal intubation" Indian Journal of Anaesthesia, Jul.-Aug. 2014, pp. 397-402, vol. 58(4).

Naik et al., "Intubation Success through I-Gel® and Intubating Laryngeal Mask Airway® Using Flexible Silicone Tubes: A Randomised Noninferiority Trial", Anesthesiology Research and Practice, 2016, pp. 1-8.

PCT International Search Report for Application No. PCT/US2019/055138 dated Feb. 3, 2020.

* cited by examiner

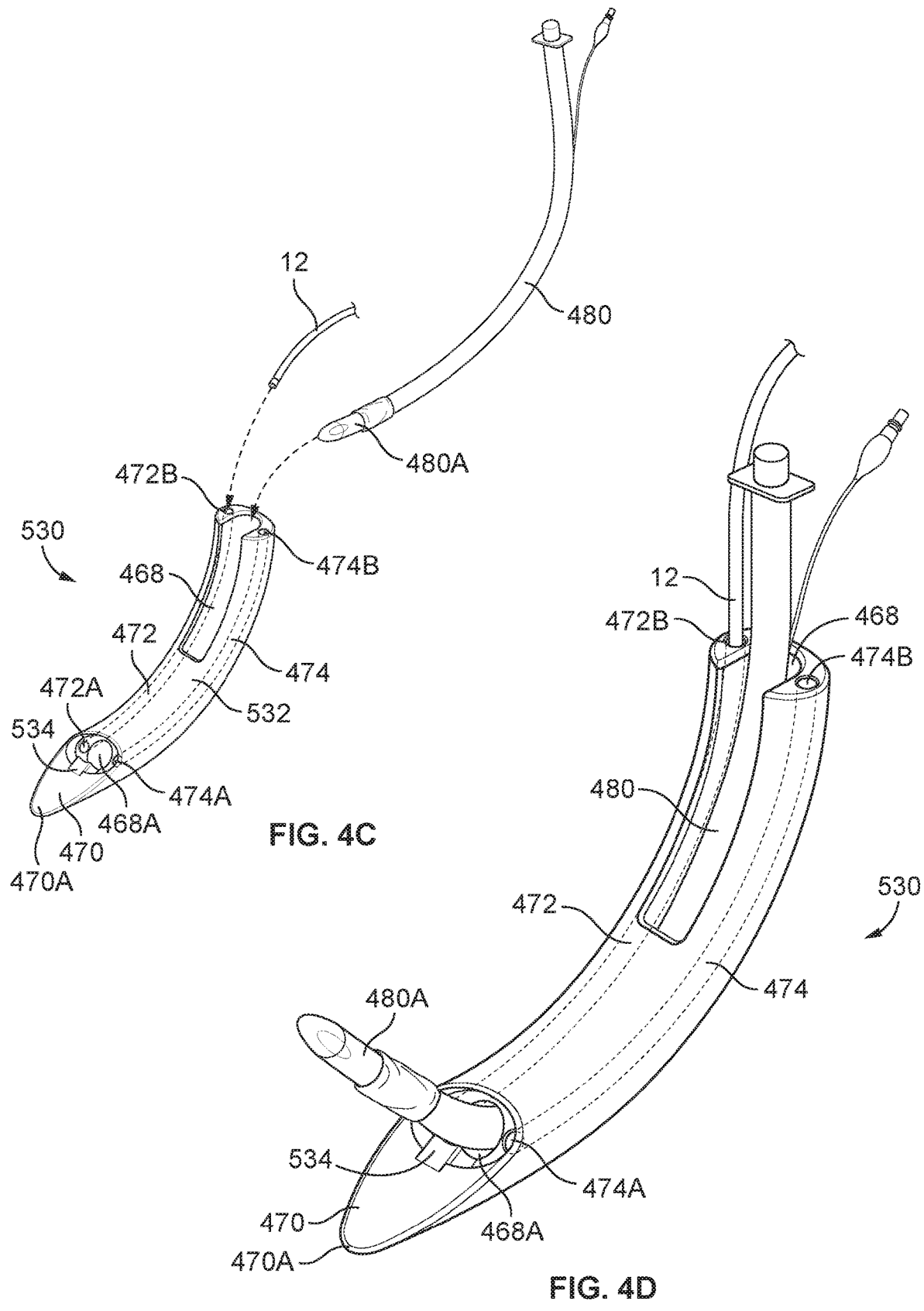

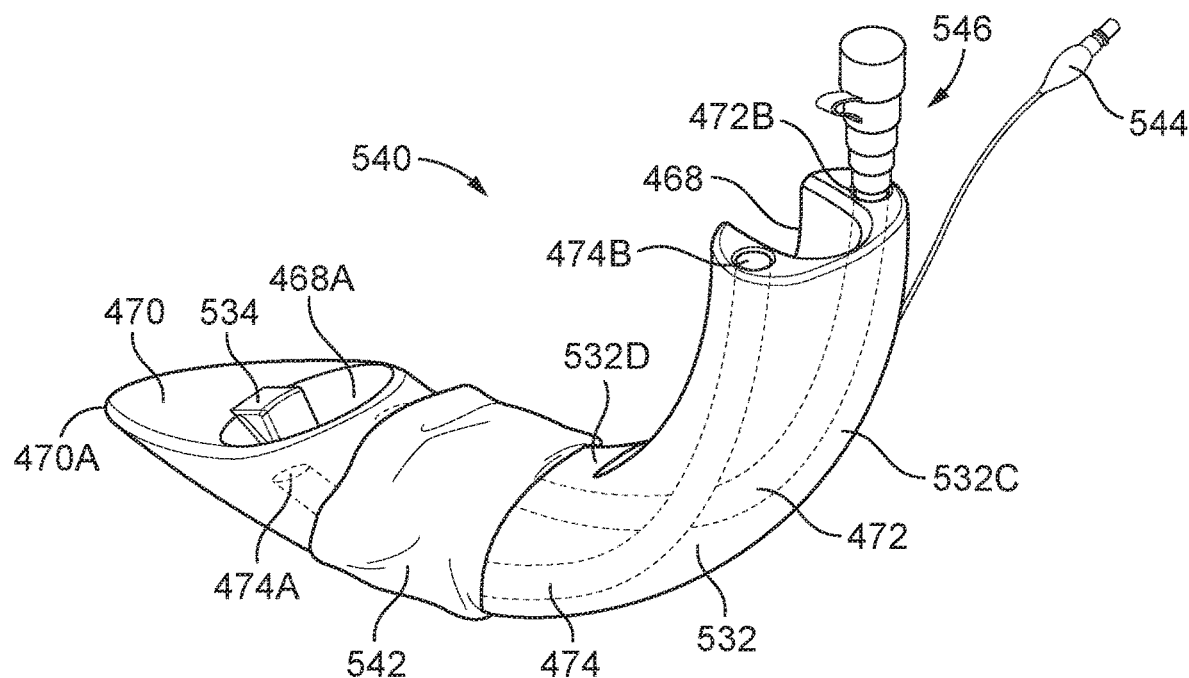
FIG. 4G
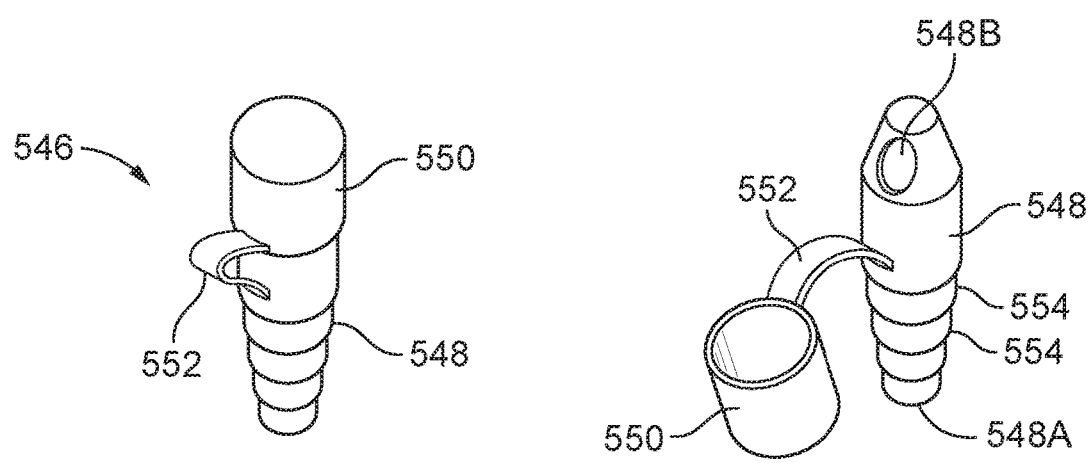
FIG. 4H
FIG. 4I

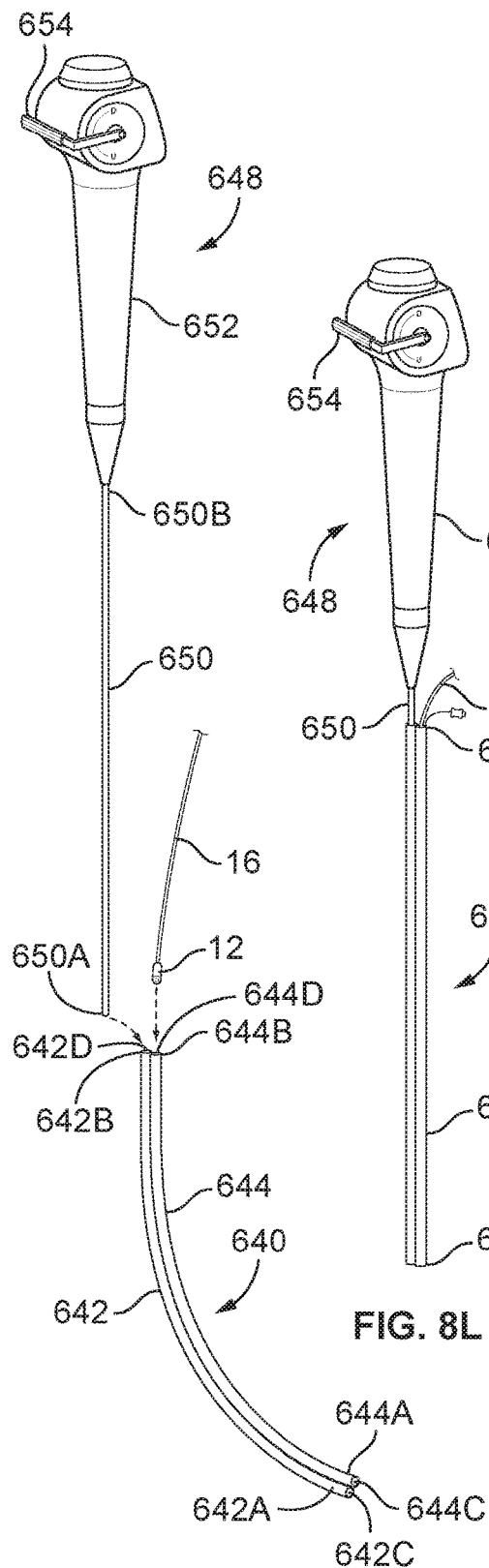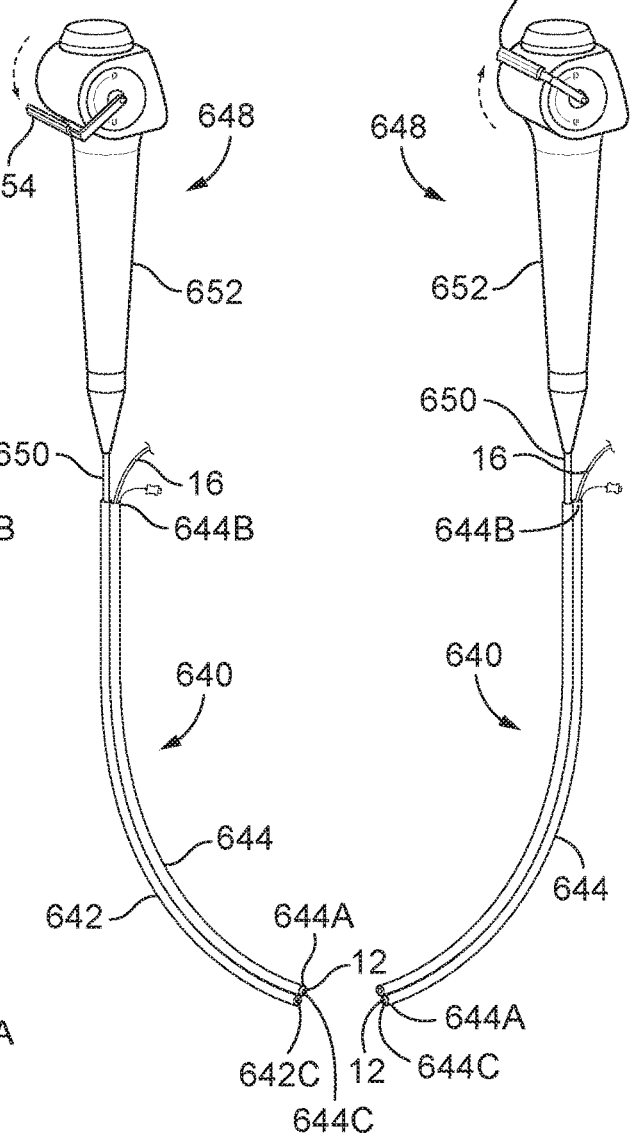
FIG. 8K
FIG. 8L
FIG. 8M
FIG. 8N

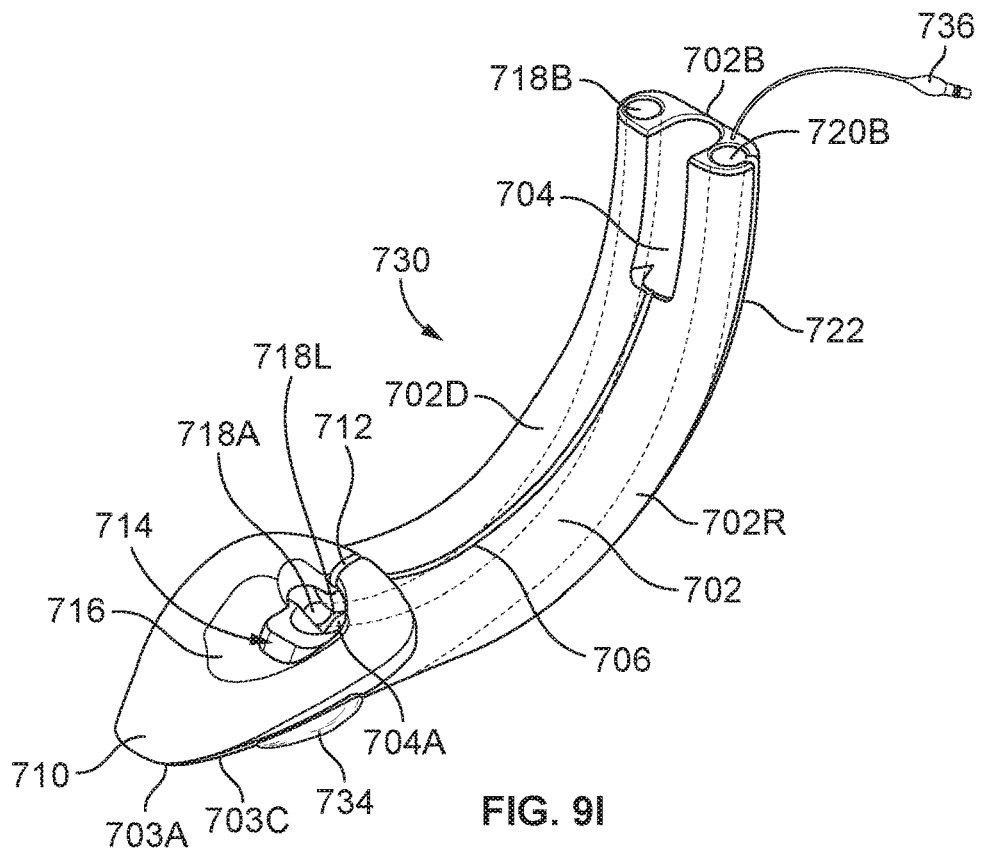
FIG. 9I
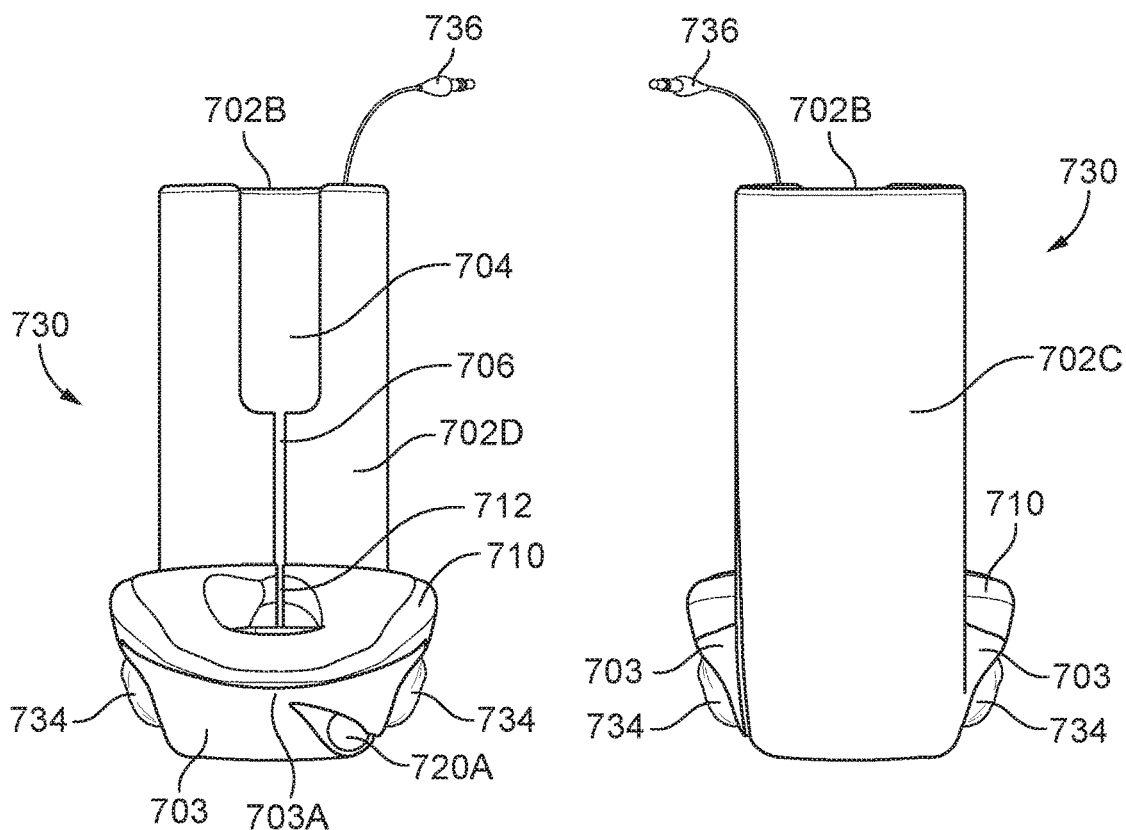
FIG. 9J
FIG. 9K

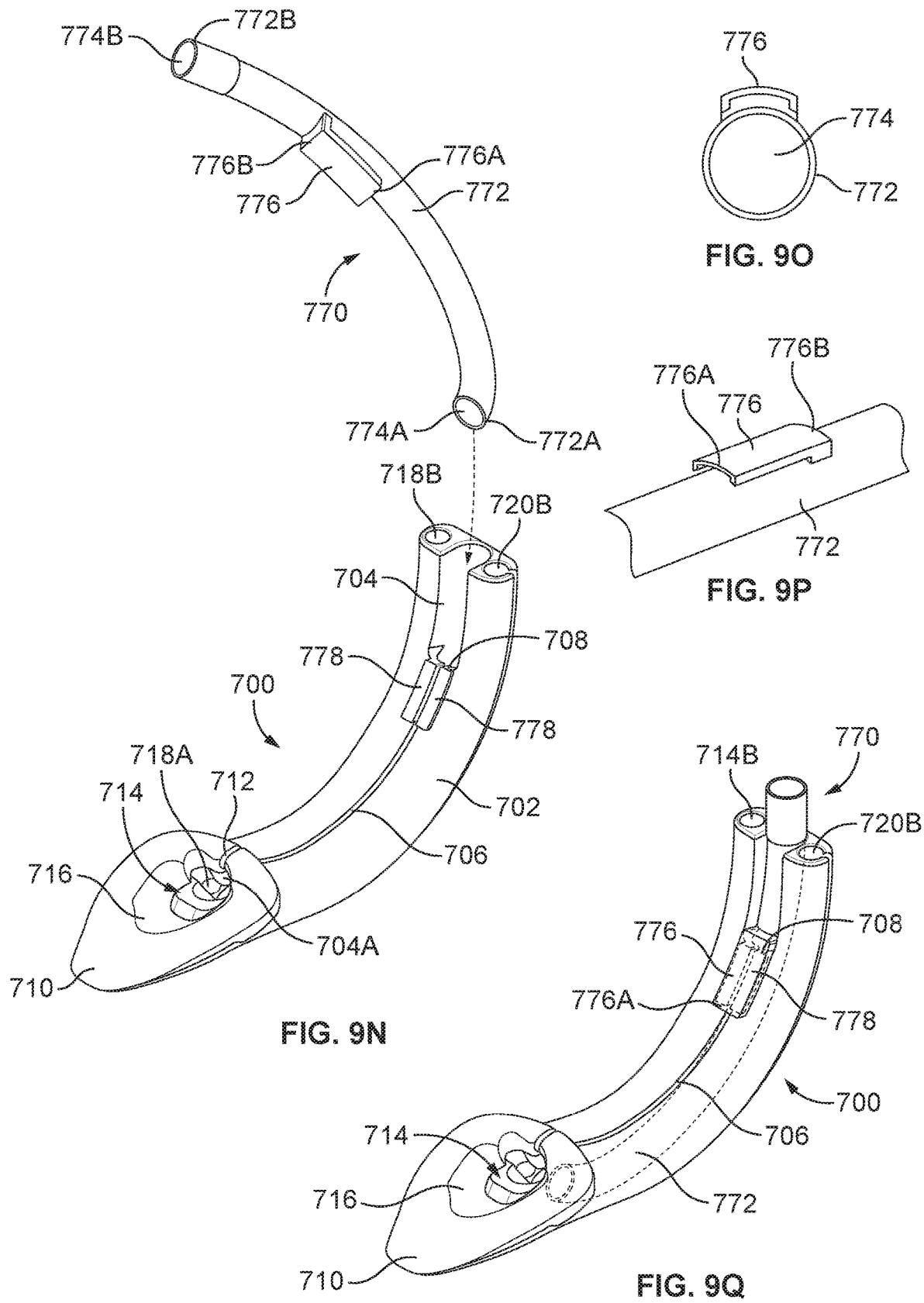

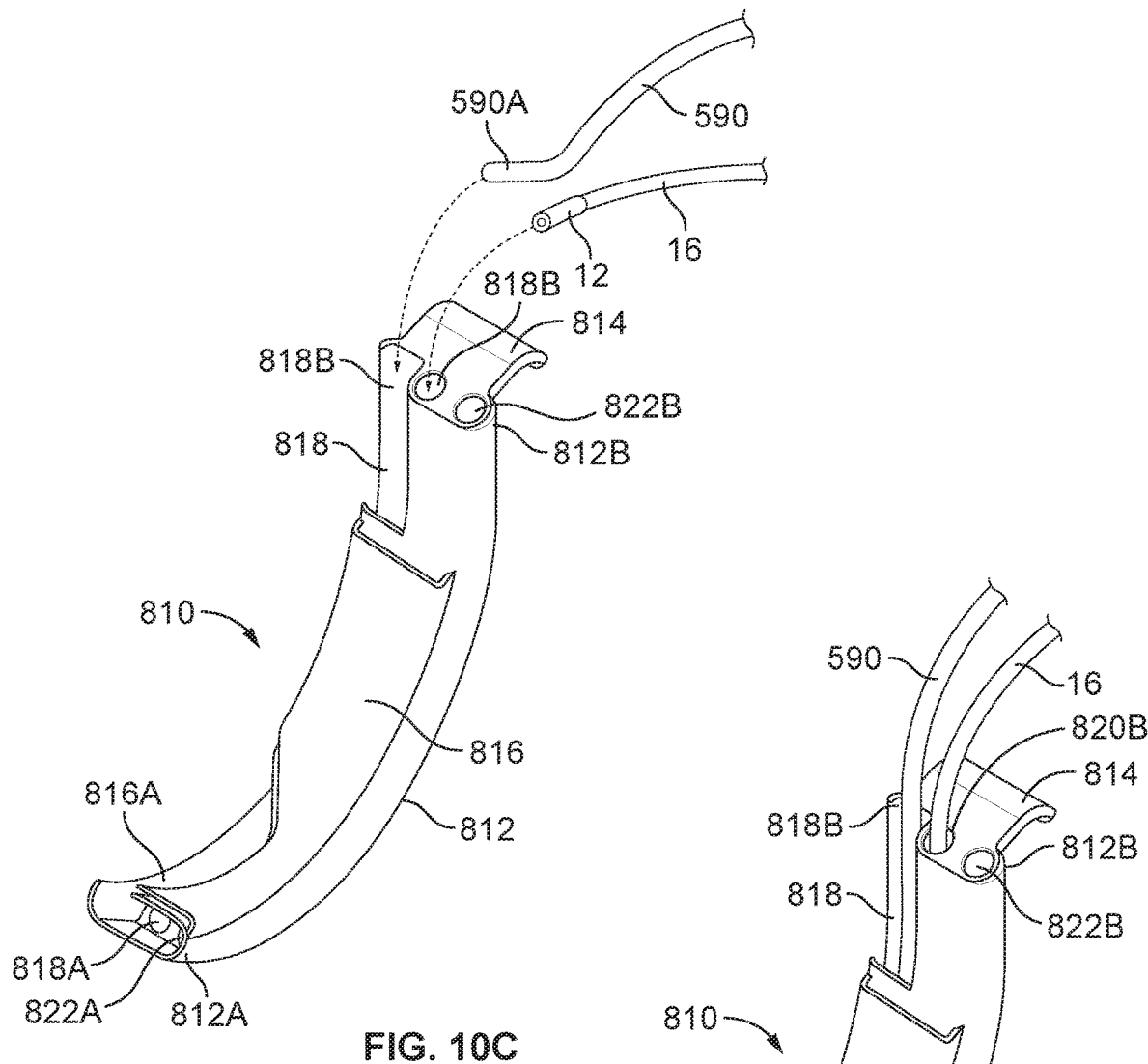

MEDICAL DEVICES FOR AIRWAY MANAGEMENT AND METHODS OF PLACEMENT

CROSS-REFERENCE TO RELATED APPLICATIONS

This application is a continuation-in-part application of U.S. patent application Ser. No. 16/156,322 filed Oct. 10, 2018, the entire disclosure of which is incorporated herein by reference.

TECHNICAL FIELD

This disclosure relates to the field of medical devices for airway management and provides disposable oral airway management devices, including various oral airway devices and adaptors, which are compatible with a camera, providing continuous visualization and monitoring during and after placement.

BACKGROUND

Various medical devices are available to stabilize a patient and facilitate his/her breathing, feeding and medication delivery. Such devices may be used in patients during surgical procedures, after certain traumas including spinal cord injuries, and in patients suffering from certain medical conditions including advanced Alzheimer's disease. These devices include endotracheal tubes, airway devices, feeding tubes, oral airways, nasal cannulas and many other devices.

A process of placing a breathing tube in a patient is called intubation. Devices such as laryngoscopes, videolaryngoscopes, fiberoptic scopes, as well as other proprietary videoscopes have been developed which are typically used in order to place an endotracheal tube into a patient. These devices may provide accuracy for initial placement, but do not provide continuous visualization or mobility of the image after the endotracheal tube has been placed in the patient. Newer devices, such as Vivasight SL or DL endotracheal tubes, provide continuous visualization, but are costly because they depend on a single use of disposable cameras and they are not transferrable from one medical device to another. The Totaltrack VLM supraglottic airway has a proprietary reusable camera for only its one device, and it cannot be transferred to other medical devices.

Certain medical devices which provide continuous visualization are described in U.S. Pat. Nos. 9,357,905, 9,415,179, 9,918,618, and Patent Publications US 2016-0038008; US 2016-0038014; and US 2016-0262603. In these devices, a camera is placed inside of a camera tube which is a separate lumen sealed at the distal end.

However, the need remains for medical devices which can be easily, rapidly and reliably inserted and removed while the devices are also compatible with a camera. There remains the need for devices which can be easily monitored during placement and after the placement has been completed for an adverse reaction in a patient such as for example, airway secretion, apnea, vomiting, internal bleedings, etc. There also remains the need for devices which can be used to ventilate a patient.

SUMMARY

The present disclosure provides medical oral airway devices and adaptors which are compatible with a camera and can be used for management of airways and/or intubation of a patient. One practitioner can perform an intubation procedure by using the devices, which eliminates the need for multiple operators and/or excessive lifting force. The use of a laryngoscope may be also avoided. The devices ensure visualization of a patient's larynx and vocal cords during placement, ventilation, intubation and/or extubation. They facilitate a placement, exchange and/or removal procedures without multiple or prolonged attempts. The present medical devices assemble various tools together for a single-step placement and eliminate the need for a multi-step intubation process. The present medical devices can be used for intubating patients who are difficult to intubate and also in at least some of patients with damaged airways. The present medical devices are also suitable for monitoring a patient for an adverse reaction such as for example, vomiting and/or obstruction.

In one aspect, the present disclosure provides an oral airway device having a tubal body curved anteriorly and made by a wall wherein the wall has a length between a distal end and a proximal end, the tubal body ends with a tongue at the distal end, wherein the wall has a dorsal surface and a ventral surface and the tongue has a dorsal surface and a ventral surface, the wall encircles a central lumen, the central lumen has a proximal opening located at the proximal end of the wall and a distal opening located at the distal end of the wall, the distal opening of the central lumen opens the central lumen onto the ventral surface of the tongue, wherein the central lumen is sloped at a first predetermined angle from the dorsal surface of the tongue and the central lumen projects an endotracheal tube or a tool above the ventral surface of the tongue when the endotracheal tube or the tool is hosted in the central lumen; the wall has a slit along the distal-proximal axis on the ventral surface of the wall, the slit opens into the central lumen; wherein the oral airway device further comprises a central ramp located on the ventral surface of the tongue in front of the distal opening of the central lumen; wherein the wall further comprises a camera channel which is a hollow passage in the wall, the camera channel runs along the distal/proximal axis, the camera channel has a distal opening which is an outlet from the wall and a proximal opening which is an inlet in the wall, the distal opening of the camera channel opens the camera channel onto the ventral surface of the tongue, wherein the camera channel is sloped at a second predetermined angle from the dorsal surface of the tongue and the camera channel projects a camera above the ventral surface of the tongue when the camera is hosted in the camera channel; and wherein the oral airway device further comprises a laryngeal cuff formed around the perimeter of the ventral surface of the tongue, and wherein the laryngeal cuff comprises a slit which is aligned with the slit of the wall.

The oral airway device may further comprise a gastric channel which is a hollow channel in the wall, the gastric channel having a proximal opening located at the proximal end of the wall and a distal opening which opens on the dorsal surface of the wall.

In some of the oral airway devices, the laryngeal cuff of the oral airway device is formed only around the distal portion of the perimeter of the ventral surface of the tongue and the laryngeal cuff does not occlude the larynx inlet completely or the laryngeal cuff is absent and is replaced with an upper esophagus cuff, and wherein the oral airway device further comprises a peripheral cuff with a slit, the peripheral cuff being wrapped around the wall proximally to the distal end of the wall, the slit of the peripheral cuff being aligned over the slit of the wall.

In some of the oral airway devices, the first predetermined angle is greater than the second predetermined angle.

In any of these oral airway devices, the laryngeal cuff may be non-inflatable or inflatable, or only lateral portions of the laryngeal cuff may be inflatable, while the distal portion of the laryngeal cuff is not inflatable.

In some of the oral airway devices, the wall does not have a slit.

In some of the oral airway devices, a diameter of the central lumen is smaller than a diameter of an endotracheal tube, and the central lumen does not carry the endotracheal tube, and wherein the oral airway device can be used with a bag-mask to ventilate a patient.

Some of the oral airway devices may further comprise at least one camera, wherein the camera is insertable into the camera channel, the camera is built-in the wall, the camera is sealed to the wall, or the camera is connected slidably along the wall. The at least one camera may transmit images, heart tones, temperature measurements and/or breath sounds wirelessly to one or more monitors being positioned at one or more remote locations.

The oral airway device may further comprise one or more of the following: a plug insertable and removable from a proximal opening the camera channel; and an accessory cap which is a hollow tube with a clip attached to the wall, the accessory cap insertable into and removable from the central lumen and the clip capable of holding edges of the wall together at the slit. Some of the oral airway devices comprise one or more cameras, each of the cameras: being insertable into the camera channel and/or central lumen, being built-in the wall, being sealed to the wall, or being connected slidably along the wall.

Some of the oral airway devices further comprise a dorsal inflatable cuff positioned on the dorsal surface of the tongue.

Some of the oral airway devices further comprises a peripheral channel which is a hollow channel in the wall, the peripheral channel having a proximal opening located at the proximal end of the wall and a distal opening which opens on the ventral surface of the tongue proximally to the laryngeal cuff and wherein the peripheral channel has a slit which opens the peripheral channel to the dorsal surface and/or a flank of the wall.

In further aspect, this disclosure provides an oral airway device comprising a tubal body created by a wall which has a length between a distal end and a proximal end, the tubal body being curved anteriorly, the wall having a dorsal surface and a ventral surface and two flanks, a first flank and a second flank, wherein the oral airway device comprises three channels, a first channel, a second channel and a third channel, the second channel and the third channel are hollow passages in the wall along the distal-proximal axis of the wall, each of the two channels opening with a proximal opening at the proximal end of the wall, and each of the channels opening with a distal opening at the distal end of the wall, wherein the first channel is located peripherally in the first flank and is a groove which runs along the proximal-distal axis of the wall and the first channel is not covered by the wall at least on a portion of the ventral surface and/or the first flank of the wall, the first channel opens with a proximal opening at the proximal end of the wall and the first channel opens with a distal opening at the distal end of the wall; wherein the second channel is located centrally in the oral airway device and second channel is compatible with a camera which can be inserted and removed from the second channel, and the third channel is located peripherally in the second flank and the third channel is compatible with a camera which can be inserted and removed from the third channel.

These oral airway devices are compatible with a laryngoscope which comprises a blade attached to a handle, and wherein the oral airway device has a holder attached to the ventral surface of the wall, the blade of the laryngoscope being insertable and removable from the holder.

In further aspects, this disclosure provides an oral airway device comprising a handle which has a length between a distal end an a proximal end, the handle formed as a semi-lumen capable of hosting an endotracheal tube, the handle ending with a tongue at the distal end of the handle, the tongue having a ventral surface and a dorsal surface, wherein a laryngeal cuff is formed around the perimeter of the ventral surface of the tongue or at least a portion of the perimeter of the ventral surface of the tongue, and wherein the tongue and the laryngeal cuff comprise a laryngeal mask, and wherein the oral airway device comprises a camera channel running along the proximal-distal axis of the handle, and wherein the camera channel is either a hollow passage in the handle or the camera channel is a tube attached along the handle, the camera channel has a proximal opening and a distal opening, and wherein the distal opening of the camera channel is located on the ventral surface of the tongue; and wherein the semi-lumen opens with a distal opening on the ventral surface of the tongue; and wherein the laryngeal cuff is inflatable, non-inflatable or some portions of the laryngeal cuff are inflatable, while other portions of the laryngeal cuff are non-inflatable.

In further aspect, this disclosure provides a method for ventilating a patient, the method comprising: inserting a camera into the camera channel in any of the oral airway devices of this disclosure, inserting the assembly of the oral airway device with the camera into the patient's oral cavity under continuous visualization by the camera, and positioning the assembly in the patient's pharynx, establishing a closed system in the assembly, and connecting the assembly to a ventilator. The method may further comprise inserting at least one of a tool and/or suction tube into the oral airway device and wherein the closed system is established by at least one of the following: placing a ventilation adaptor over the wall of the oral airway device and/or inserting the accessory cap in the central lumen of the oral airway device.

Further aspects of this disclosure include a system for managing airways in a patient, the system comprising:

any of the oral airway devices with the camera channel of this disclosure;

a camera insertable and removable from the camera channel; and a ventilator adaptor with at least one cap for establishing a closed system in the oral airway device.

Further aspects of this disclosure include a method for intubating a patient, the method comprising:
  a) inserting an endotracheal tube into the central lumen of the oral airway device of this disclosure,
  b) positioning the assembly of step a) in the patient and inserting the endotracheal tube through the vocal cords under visualization by a camera;
  c) separating the endotracheal tube from the oral airway device through the slit; and
  d) removing the oral airway device from the patient while the endotracheal tube remains inserted.

Further aspects of this disclosure include a method for extubating or exchanging an endotracheal tube in a patient intubated with a first endotracheal tube placed in the oral airway device of this disclosure, the method comprising:

a) removing the first endotracheal tube from the patient while the oral airway device remains placed in the patient under continuous visualization from a camera placed in the camera channel of the oral airway device; and b) if the first endotracheal tube should be exchanged, inserting a second endotracheal tube into the central lumen of the oral airway device which is still placed in the patient and placing the second endotracheal tube through the patient's vocal cords under continuous visualization by the camera.

BRIEF DESCRIPTION OF THE DRAWINGS

FIG. 4C depicts loading an endotracheal tube and inserting a camera into the oral airway device of FIG. 4A.

FIG. 4D depicts an endotracheal tube being loaded and a camera being inserted into the oral airway device of FIG. 4A.

FIG. 4G depicts the oral airway device of FIG. 4B from the dorsal surface with a plug inserted into one of the peripheral channels.

FIG. 4H depicts a plug which is capped with a cap.

FIG. 4I depicts the plug of FIG. 4H with the cap being removed.

FIG. 8K depicts a bronchoscope being combined with a camera via the adaptor of FIG. 8C.

FIG. 8L depicts the adaptor of FIG. 8K hosting the bronchoscope of FIG. 8K and the camera.

FIG. 8M depicts how the adaptor of FIG. 8K hosting the bronchoscope of FIG. 8K and the camera can be manipulated by toggling a bronchoscope handle counter-clockwise.

FIG. 8N depicts how the adaptor of FIG. 8K hosting the bronchoscope of FIG. 8K and the camera can be manipulated by toggling a bronchoscope handle clockwise.

FIG. 9I depicts an oral airway device with a laryngeal cuff and a distal inflatable cuff.

FIG. 9J depicts another view of the oral airway device of FIG. 9I.

FIG. 9K depicts another view of the oral airway device of FIG. 9I.

FIG. 9N depicts insertion of an accessory cap into the oral airway device of FIG. 9A.

FIG. 9O depicts a cross-sectional view of the accessory cap with a clip of FIG. 9N.

FIG. 9P is an enlarged side view of a portion of the accessory cap of FIG. 9N.

FIG. 9Q is the oral airway device of FIG. 9A assembled with the accessory cap of FIG. 9N.

FIG. 10C depicts the oral airway device of FIG. 10A being assembled with a bougie and a camera.

FIG. 10D depicts the oral airway device of FIG. 10A hosting a bougie and a camera.

DETAILED DESCRIPTION

Figure 1A:
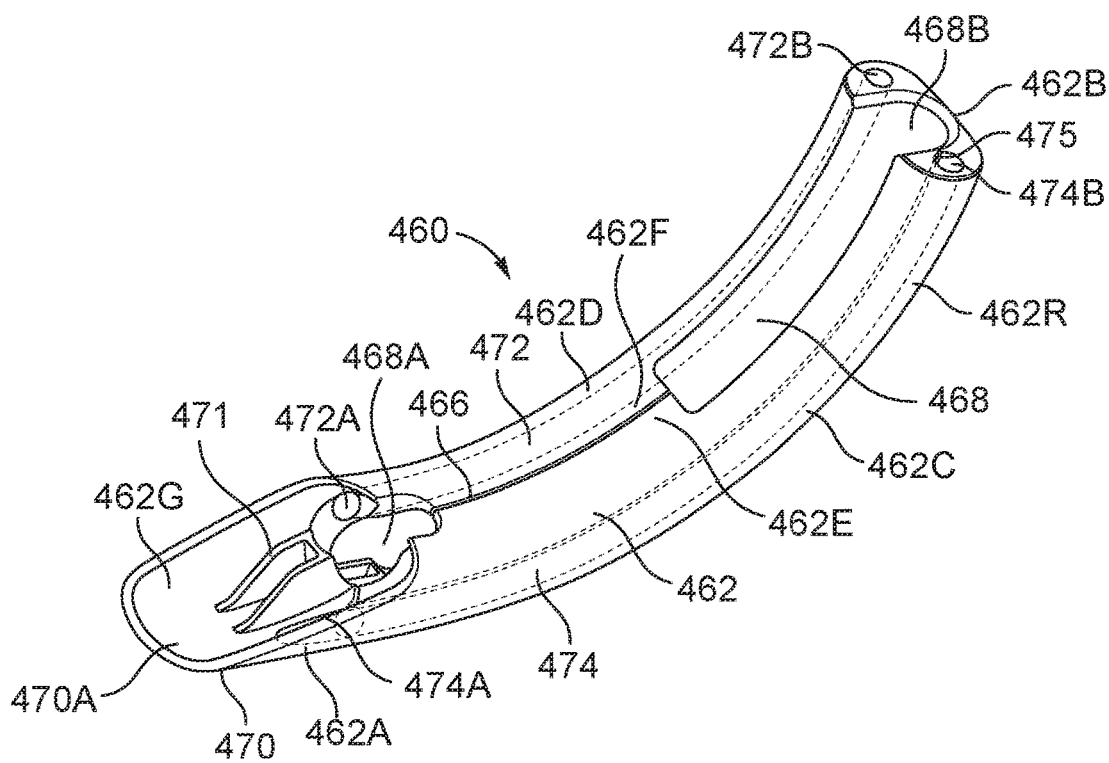
FIG. 1A depicts an oral airway device comprising a peripheral camera channel.

The present disclosure provides medical devices for airway management, including ventilation, intubation, and monitoring a patient. The present disclosure also provides methods for a rapid and accurate placement of an airway management device in a patient and remote continuous real-time monitoring of the patient after the placement.

The present devices comprise at least one hollow channel with an inlet and outlet. The present devices are compatible with a camera which can be inserted into the channel. Thus, ventilation, intubation and/or extubation of a patient is conducted under continuous visualization. The devices can also monitor heart tones, sound transmission and temperature.

A camera compatible with the present devices may comprise a digital camera coupled to a power cord. The digital camera may comprise CCD (charge-coupled device) and/or CMOS (complementary metal-oxide semiconductor) sensors. The captured images may be transmitted either with a wire or wirelessly. The camera may be also equipped with means for monitoring sounds, including breath sounds and heart tones. The camera may be connected to a cable. The camera may transmit images, sounds and heart tones wirelessly to one or more remote locations. Accordingly, a patient can be monitored remotely and from different locations. This may be helpful when a first responder has to perform an emergency rescue ventilation immediately at the scene. Such emergency placements can be guided and/or evaluated remotely with the help a camera which in the present devices may transmit images and sounds to monitors, such as telephone and/or computer screens located remotely, for example in a hospital and/or an emergency room.

In this disclosure, if the same element appears in several different drawings, the element may be referred to by the same reference number. It will be appreciated that if an element is described in connection with one embodiment, other embodiments may comprise this element as well. If an element was described in detail in a first embodiment and the element is then referred to under the same reference number in connection with other subsequent embodiments, the description from the first embodiment still applies even if the description is not repeated in full again in connection with the subsequent embodiments.

In one aspect, the present disclosure provides oral airway devices which comprise an endotracheal tube (ETT) lumen with a slit for delivering a breathing tube, and one or more additional channels for a robust assembly with one or more cameras and additional tools, including, but not limited to a bougie and a gastric suction tube. The oral airway devices also comprise a ramp which ensures an optimum angle for an entry of an endotracheal tube through the vocal cords such that the placement can be completed expeditiously and the risks of esophageal intubation and/or injuries to vocal cords are minimized. The oral airway devices can be also used to ventilate a patient. The oral airway devices provide continuous visualization and monitoring of breathing sounds and heart beats. Thus, a patient who is ventilated and/or is intubated can be monitored continuously and remotely, if needed, for adverse reactions, including vomiting, bleeding, obstruction and any failure in a system that may require a replacement of an endotracheal tube and/or oral airway device. The oral airway devices also provide a continuous monitoring during placement, intubation and extubation. Because the oral airway devices comprise a slit leading into an the ETT lumen, the oral airway devices can be separated and removed from an endotracheal tube after the endotracheal tube has been placed and while the endotracheal tube remains inserted. Some of the oral airway devices also comprise a laryngeal cuff which creates a seal needed to ventilate a patient through the ETT lumen of the oral airway devices. The oral airway devices can be made in different sizes in order to accommodate pediatric patients and adults of different height and weight, including obese patients.

These oral airway devices with the ETT lumen will now be described with reference to FIGS. 1A-1V, FIG. 2, FIGS. 3A-3C, FIGS. 4A-4K and FIGS. 9A-9W.

Referring to FIG. 1A, it provides one embodiment of an oral airway device according to this disclosure, generally 460. The oral airway device 460 is a tubal body which is curved such that the oral airway device 460 follows the contour of the roof of a patient's mouth during insertion of the device 460 into the patient.

The curved tubal body of the oral airway device 460 is made by a wall 462 with a distal end 462A and a proximal end 462B.

In this disclosure, "the proximal end of a device" means the end which is the closest to a practitioner during insertion of the device into a patient's body. In this disclosure, "the distal end of a device" means the end which is opposite to the proximal end of the device. The distal end is the end which is inserted first into the patient. The distal end is also considered to be the most distal end to a practitioner during insertion of a device into the patient.

In the oral airway device 460, the wall 462 is curved along the distal-proximal 462A-462B axis such that the wall 462 follows the contour of the roof of a patient's mouth. The wall 462 creates an arch. The wall 462 has a dorsal surface 462C and a ventral surface 462D. Because of the arch curvature, a length of the wall 462 is longer on the dorsal surface, 462C than on the ventral surface, 462D.

Typically, the ventral surface 462D is in contact with the patient's tongue during the insertion of the device 460 into an oral cavity. The dorsal surface 462C, is opposite to the ventral surface, 462D.

In this disclosure, the ventral surface of a device is the surface which is in contact with a patient's tongue during the insertion into the patient's oral cavity. The distal surface is the surface which is opposite to the ventral surface. In this disclosure, a lateral surface or a flank is a surface located between the dorsal and ventral surfaces. An oral airway device in this disclosure has two flanks, the left flank and the right flank.

In the drawing of FIG. 1A, the ventral surface 462D and the right flank 462R are shown. The left flank, 462L is opposite to the right flank 462R and is not visible in the drawing of FIG. 1A. In the drawing of FIG. 1A, only a portion of the dorsal surface 462C is visible.

The wall 462 encircles a lumen 468. The lumen 468 is hollow and has a distal opening 468A in proximity to the distal end 462A of the wall 462. The lumen 468 has a proximal opening 468B at the proximal end of the wall 462.

A medical device, such as for example an endotracheal tube or any other tool or device suitable for managing patient's airways, can be placed in the lumen 468 or removed from the lumen 468 by opening the wall 462 along the slit 466 which runs along the distal-proximal axis 462A-462B.

In the embodiment of FIG. 1A, the wall 462 has the slit 466 which runs along the distal-proximal 462A-462B axis on the ventral surface 462D. In other embodiments, the slit 466 may be placed at other surfaces of the wall 462, so long the slit 466 is located such that a practitioner can access the lumen 468 through the slit 466.

The wall 462 is made of a flexible material, such as for example, plastic or rubber. Accordingly, once an endotracheal tube is loaded in the lumen 468, the wall 462 can close back along the slit 466 and it holds the endotracheal tube in place.

Thus, one of the uses for the lumen 468 is to deliver an endotracheal tube during endotracheal placement into a patient. Accordingly, the lumen 468 may be referred in this disclosure as the endotracheal tube (ETT) lumen. However, it will be understood that the ETT lumen 468 may be used for delivery of other breathing tubes and/or tools and/or devices suitable for managing airways. As discussed in more detail below, the ETT lumen 468 itself can be used for ventilating a patient if needed. Accordingly, the device 460 can be used with or without an endotracheal tube for managing airways.

It will be appreciated that in the drawing of FIG. 1A, the ETT lumen 468 is positioned centrally in the curved tubal body of the oral airway device 460. In other embodiments and as discussed in more detail below, the ETT lumen 468 may be positioned peripherally in the curved tubal body of the oral airway device 460.

The oral airway device 460 provides several technical advantages in comparison to conventional oral airway devices which do not have a slit. First, it is much easier to load an endotracheal tube or any other breathing tube or tool or device into the ETT lumen 468 of the oral airway device 460 by opening the wall 462 at the slit 466.

Second, the oral airway device 460 can be separated and removed from a patient after the endotracheal tube has been inserted in the patient and while the endotracheal tube still remains inserted and in place in the patient without the need of removing the whole assembly from the patient first.

In the drawing of FIG. 1A, the wall 462 has two flaps, 462E and 462F, one on each side of the slit 466. The flaps 462E and 462F hold a device, such as for example an endotracheal tube, loaded into the ETT lumen 468 in place and prevent a slippage of an endotracheal tube from the ETT lumen 468 during insertion into a patient.

In other embodiments, the slit 466 may not have flaps. In some embodiments, the edges of the wall 462 may touch at the slit 466. In other embodiments, there is a gap between the edges of the wall 462 at the slit 466.

In the drawing of FIG. 1A, at least some proximal portion of the ETT lumen 468 is not covered by the wall 462 on the ventral surface 462D. Accordingly, some proximal portion of the ETT lumen 468 is exposed on the ventral surface 462D. In other embodiments, where the wall 462 does not have flaps, at least some proximal portion of the ETT lumen may still not be covered by the wall 462. Exposing a portion of the ETT lumen 468 facilitates insertion and removal of an endotracheal tube or other tool/device into and from the ETT lumen 468.

In other embodiments, the slit 466 may still provide access to the ETT lumen 468, but runs all the way or almost all the way from the proximal end 462B to the distal end 462A of the wall 462. In these embodiments, no ETT lumen 468 or only a very minimal portion of it is not covered by the wall 462 on the ventral surface 462D. In these embodiments, (not shown) two or more flaps (not shown) may be positioned on each side of the slit along the distal-proximal 462A-462B axis.

In some other embodiments, the slit 466 may be narrow such that the edges of the wall 462 touch or almost touch along the length of the slit 466. In other embodiments, the slit 466 has a gap such that there is always a gap between the edges of the wall 462 along the slit 466. In the drawing of FIG. 1A, the slit 466 is on the ventral surface 462D. In other embodiments (not shown), the slit 466 still provides access to the ETT lumen, but the slit 466 is positioned on the dorsal surface 462C or at some location other than the ventral surface. For example, between the dorsal and ventral surfaces.

At the distal end 462A, the wall 462 ends with a tongue 470 on the dorsal surface 462C. The distal end 470A of the tongue 470 may be in an oval or round shape. The tongue 470 is tapered at its distal end 470A. The tongue 470 is used to gently push patient's tissues apart during insertion of the oral airway device 460 through the patient's oral cavity and pharynx. The tongue 470 protrudes distally from the wall 462.

There is a ramp 471 attached to the internal surface 462G of the tongue 470. The ramp 471 is positioned proximally to the tongue 470 and distally to the distal opening 468A of the ETT lumen 468.

The ramp 471 elevates above the surface of the internal surface 462G of the tongue. The function of the ramp 471 is to lift and support a distal end of a device loaded in the ETT lumen 468, such as for example an endotracheal tube, above the surface of the internal surface 462G.

The wall 462 has at least two hollow channels, 472 and 474. The channel 472 is a hollow passage in the wall 462. The channel 472 is positioned peripherally to the ETT lumen 468 in the embodiment of FIG. 1A. In other embodiments, the ETT lumen 468 may be positioned peripherally and the channel 472 may be positioned centrally. The channel 472 may be used for inserting a camera or some other tools or devices. Accordingly, the channel 472 may be referred in this disclosure as the camera channel 472. It will be appreciated, that the channel 472 may be used for insertion of other tools and or devices.

The camera channel 472 has a proximal opening 472B which is an inlet into the camera channel 472 and which is positioned at the proximal end 462B of the wall 462. The camera channel 472 runs along the distal-proximal 462A-462B axis of the wall 462. The camera channel 472 ends with a distal opening 472A which is an outlet from the camera channel 472. In the drawing of FIG. 1A, the distal opening 472A is positioned near the distal end 462A of the wall 462. In other embodiments, the length of the camera channel 472 may be shorter and the distal opening 472A may be poisoned anywhere along the length of the wall 462, for example, two-thirds of the wall length.

The distal opening 472A of the camera channel 472 preferably is not sealed such that a camera can protrude distally from the camera channel 472. In some embodiments, the distal opening 472A is sealed with a transparent material (not shown in the drawing of FIG. 1A) such that a camera can capture images through the sealed window while located in the camera channel 472.

A camera (not shown) can be inserted through the proximal opening 472B in the camera channel 472. The camera can protrude from the distal opening 472A of the channel 472. Any camera suitable for visualization of patient's organs can be used in the oral airway device 460. The camera is insertable and removable from the camera channel 472. A position of the camera at the distal opening 472A of the camera channel 472 can be adjusted as needed in order to monitor patient's tissues and passage of the oral airway device 460 through the patient's oral cavity and into a pharynx during placement. The oral airway device 460 when equipped with a camera can provide continuous visualization of patient's larynx and vocal cords. This facilitates an accurate and rapid placement and avoids the need for multiple and lengthy attempts.

In some other embodiments, the oral airway device 460 may comprise at least one camera (not shown) which is built-in the wall 462, sealed to the wall 462 or is connected slidably along the wall 462. In further embodiments, the oral airway device 460 may comprise multiple cameras.

At least one or more cameras may transmit images wirelessly to one or more monitors and at least some of the monitors may be positioned at one or more remote locations. At least some the cameras may have a capability to transmit images, and also heart tones and sounds.

In further embodiments, the oral airway device 460 may comprise an esophageal stethoscope (not shown) which may be either built-in the wall 462 or the esophageal stethoscope may be insertable into the channel 472, the ETT lumen and/or the channel 472. In further embodiments, the oral airway device 460 may comprise a temperature probe (not shown) which may be either combined with the esophageal stethoscope (not shown) or the temperature probe may be built-in the wall 462 or the temperature probe may be insertable into the channel 472, the ETT lumen and/or the channel 472.

In some embodiments, the camera channel 472 is a hollow passage in the wall 462 and the camera channel 472 is completely separated from the ETT lumen 468.

In other embodiments, the camera channel 472 is a semi-lumen which is connected to the ETT lumen 468 with gap or slit. In further embodiments, there is a slit that runs along the length of the camera channel 472 on one of the surfaces of the wall 462. A camera can be easily inserted and removed from the camera channel 472 by being pulled through the slit.

In the embodiment of FIG. 1A, the oral airway device 460 comprises a second channel 474. In other embodiments, the channel 474 may be missing. In some other embodiments, more than one channel 474 is present.

The channel 474 is a hollow passage in the wall 462. The channel 474 can be used for aspirating fluids by inserting a suction tube in the channel 474. In this disclosure, the channel 474 may be referred as the esophageal channel 474. The esophageal channel 474 may be used for aspirating stomach contents and in order to prevent vomiting.

The esophageal channel can be also used for inserting other tools, including, but not limited to, a bougie, stylet, forceps, esophageal stethoscope and/or camera.

The esophageal channel 474 runs along the distal-proximal 462A-462B axis of the wall 462. The esophageal channel 474 is located peripherally to the ETT lumen 468 in the embodiment of FIG. 1A. As can be seen in the FIG. 1A, the channels 472 and 474 flank the ETT lumen 468 which is positioned between the channels 472 and 474.

In other embodiments, the camera channel 472 may be positioned centrally on the dorsal surface 462C and as discussed in more detail below. In other embodiments, the esophageal channel 474 may be positioned centrally on the dorsal surface 462C and as discussed in more detail below.

In yet other embodiments, the ETT lumen 468 may be positioned peripherally, as discussed in more detail below.

However, in all embodiments of the oral airway device 460, the relative positioning of the ETT lumen 468, the camera channel 472 and the esophageal channel 474 is such that it permits a practitioner to visualize by using camera tools/devices protruding from the ETT lumen and/or the esophageal channel 474.

The esophageal channel 474 opens with a proximal opening 474B near the proximal end 462 of the wall 462. The proximal opening 474B is an inlet through which a tool can be inserted into the esophageal channel 474.

The esophageal channel 474 ends with a distal opening 474A which is an outlet in near proximity to the distal end 462A of the wall 462. A tool or camera which is inserted into the channel 474 may protrude distally from the channel 474 from the distal end 474A.

In some embodiments, the esophageal channel 474 can be extended through the tongue 470 and up to the tongue tip 470A. In this embodiments, the distal opening 474 is located distally to eh distal end 462A of the wall 462.

A tool, such as for example a suction tube, (not shown) can be inserted through the proximal opening 474B in the esophageal channel 474. The suction tube (or any other tool being inserted in the channel 474) can protrude from the distal opening 474A of the channel 474. The esophageal channel 474 can be used for hosting a bougie, a stylet, a camera, stethoscope, a temperature probe, a sound-monitoring and/or heart tone device which may be combined with a camera, forceps and/or any other tool that is used during intubation and or extubation of a patient.

Any of these tools are insertable and removable from the esophageal channel 474 and/or the camera channel 472 and can be used as needed for hosting these tools as well. A position of the tool at the distal opening 474A can be adjusted as needed in order to manipulate patient's tissues and/or provide suction if needed. In some embodiments, the esophageal channel 474 is a passage in the wall 462 and the esophageal channel 474 is completely separated from the ETT lumen 468.

In other embodiments, the esophageal channel 474 is a semi-lumen which is connected to the ETT lumen 468 with a slit 475 as showing in FIG. 1A. The slit 475 that runs along the length of the esophageal channel 474. The slit 475 opens into the ETT lumen 468 in the embodiment of FIG. 1A. In other embodiments, the slit 475 may open externally on the wall 462.

While the individual position of the two channels 472 and 474 may vary in the wall 462, a relative positioning of the channels 472 and 474 is such that when a camera is inserted in the camera channel 472 and protrudes from the distal opening 472A of the camera channel 472, the camera can visualize a distal end of a tool inserted into the esophageal channel 474 and protruding from the distal opening 474A of the esophageal channel 474. Accordingly, manipulations of the tool can be visualized with the camera, as needed.

Because the oral airway device 460 assembles several tools together, one practitioner can perform a placement of the oral airway device 460. There is no need to involve multiple operators for manipulating different tools.

In the drawing of FIG. 1A, the camera channel 472 is positioned in the wall 462 such that the distal opening 472A of the channel 472 opens on the ventral surface 462D or near the ventral surface 462D. The channel 474 is positioned such that its distal opening 474A opens on the dorsal surface 462C or near the dorsal surface 462C of the wall 462. In other embodiments, the camera channel 472 is positioned in the wall 462 such that the distal opening 472A of the channel 472 opens on the dorsal surface 462C or near the dorsal surface 462C. The esophageal channel 474 can be positioned such that its distal opening 474A opens on the dorsal surface 462C or near the dorsal surface 462C of the wall 462.

As can be appreciated by a person of skill, in some embodiments, the channels 472 and 474 may be interchangeable, i.e. a camera can be inserted into either of the two channels, as needed. In further embodiments, the device 460 may have more than two channels in the wall 462. These additional channels may be located peripherally to the ETT lumen 468. In some procedures, a camera can be also placed into the ETT lumen 468, if needed.

In the embodiment of FIG. 1A, the wall 462 has uneven thickness. The thickness of the wall 462 may be greater on the dorsal surface of the wall 462 and/or in flanks 462L and/or 462R between the dorsal surface 462C and the ventral surface 462D in order to accommodate the channels 472 and 474 which are typically hollow passages in the wall 462. In other embodiments, the thickness of the wall 462 may be the same or nearly the same around the perimeter of the oral airway device 460.

Figure 1B:
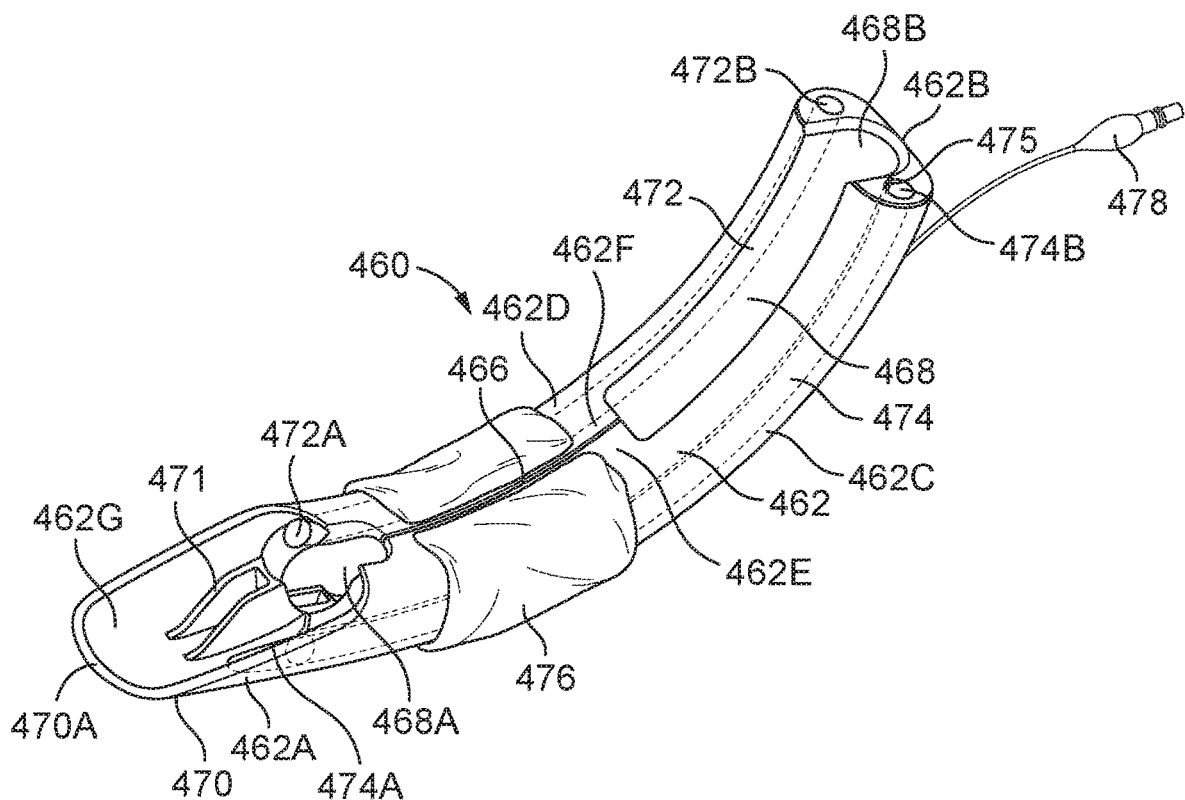
FIG. 1B depicts an oral airway device with a cuff and comprising a peripheral camera channel.

FIG. 1B provides a further embodiment of the oral airway device 460. All elements are as described in connection with FIG. 1A, except the oral airway device 460 in the embodiment of FIG. 1B comprises a cuff 476. The cuff 476 is attached around the perimeter of the wall 462 and it wraps around the wall 462 proximally to the distal opening 468A of the ETT lumen 468. The cuff 476 can be inflated with means 478. If needed, the cuff 476 is inflated after the device 460 is inserted into a patient in order to establish a closed system and to ventilate a patient. The cuff 476 is attached to the wall 462 and it does not go over the slit 466 such that when the cuff 476 is not inflated, the edges of the wall 462 can be still pulled apart at the slit 466 in the area where the cuff 476 is attached to the wall 462. While in the embodiment of FIG. 1B, the cuff 476 is inflatable, in other embodiments, the cuff 476 may be a soft donut-like cushion which is not inflatable.

Figure 1C:
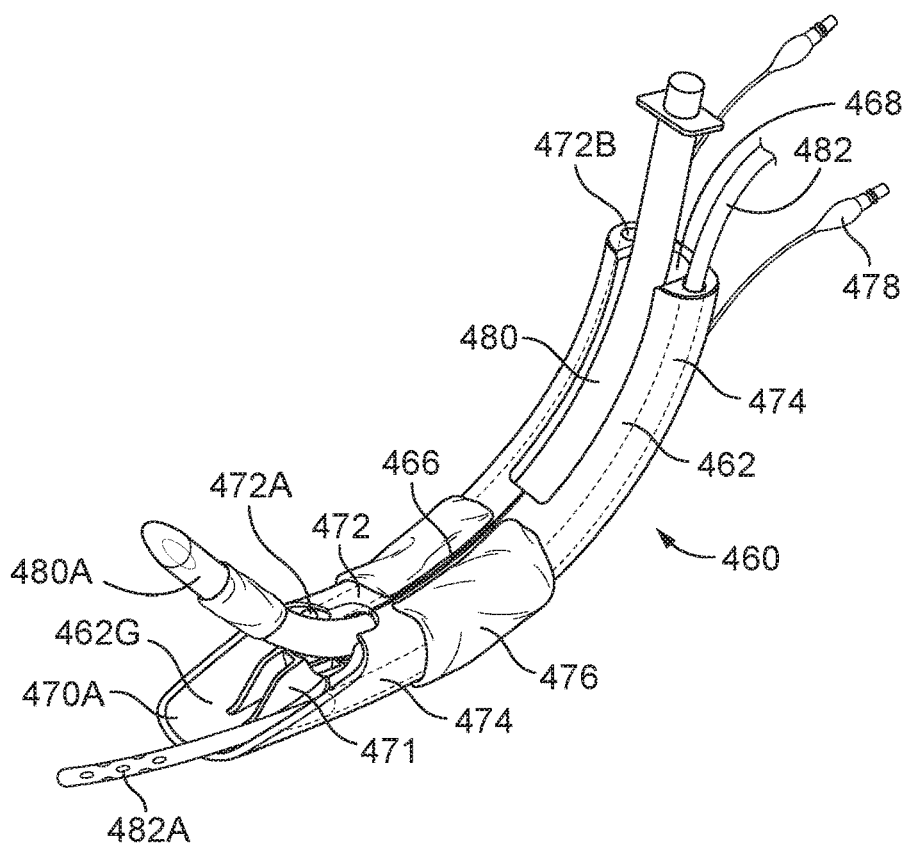
FIG. 1C depicts an endotracheal tube and a suction tube loaded onto the oral airway device of FIG. 1B.

FIG. 1C shows an endotracheal tube 480 and a suction tube 482, both of which are inserted into the oral airway device 460. All elements of the oral airway device 460 as were described in connection with FIGS. 1A and 1B. As can be seen in FIG. 1C, the endotracheal tube 480 is inserted into the ETT lumen 468. A distal end 480A of the endotracheal tube 480 protrudes from the distal opening 468A of the ETT lumen 468. The endotracheal tube 480 is elevated above the surface of the internal surface 462G by the ramp 471. This provides a technical advantage of preventing the distal end 480A of the endotracheal tube 480 from pushing and dragging against the surface of the device 460 and/or against tissues of a patient during insertion of the device 460 into the patient.

Accordingly, with the help of the ramp 471 and under continuous visualization from a camera inserted into the camera channel 472, an insertion of the endotracheal tube 480 (or any other device loaded in the ETT lumen 468) can be accomplished quicker as the position of the endotracheal tube 480 is guided and the endotracheal tube 480 is prevented from folding, bending and otherwise blocking completion of the insertion.

The oral airway device 460 provides a capability for combining several cameras, each of the cameras being positioned at a different location and accordingly providing a view of the patient's tissues from a different angle. This improves accuracy for endotracheal tube placement.

In the drawing of FIG. 1C, the suction tube 482 is inserted into the esophageal channel 474. The distal end 482A of the suction tube 482 protrudes from the distal opening 474A of the channel 474. Just like a camera which is insertable and removable from the camera channel 472, the suction tube 482 can be also easily inserted and removed from the esophageal channel 474.

Figure 1D:
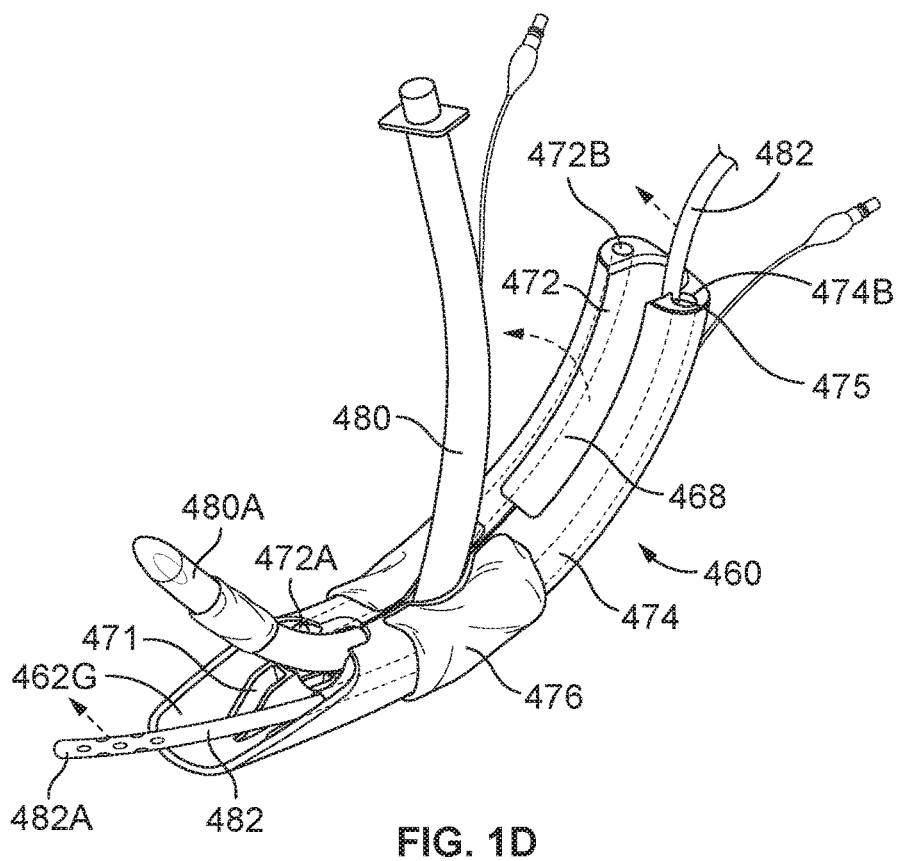
FIG. 1D depicts a removal of the endotracheal tube from the oral airway device of FIG. 1B.

Referring to the drawing of FIG. 1D, it shows how the endotracheal tube 480 can be separated from the oral airway device 460 by being pulled through the slit 466. This allows a practitioner to easily remove and/or replace an endotracheal tube as needed while the oral airway device 460 is still placed in a patient. In alternative, the oral airway device 460 can be easily removed from the patient while the endotracheal tube 480 remains inserted and in place in the patient. This provides a technical advantage of not needing to conduct multiple rounds of intubation and extubation.

As is also shown in the drawing of FIG. 1D, the suction tube 482 can be easily removed from the oral airway device 460 from the slit 475 of the esophageal channel 474. Thus, a practitioner can remove the suction tube 482 or any other tool, such as for example as a bougie, while the oral airway device 460 remains inserted into the patient.

Figures 1E, 1F, 1G:
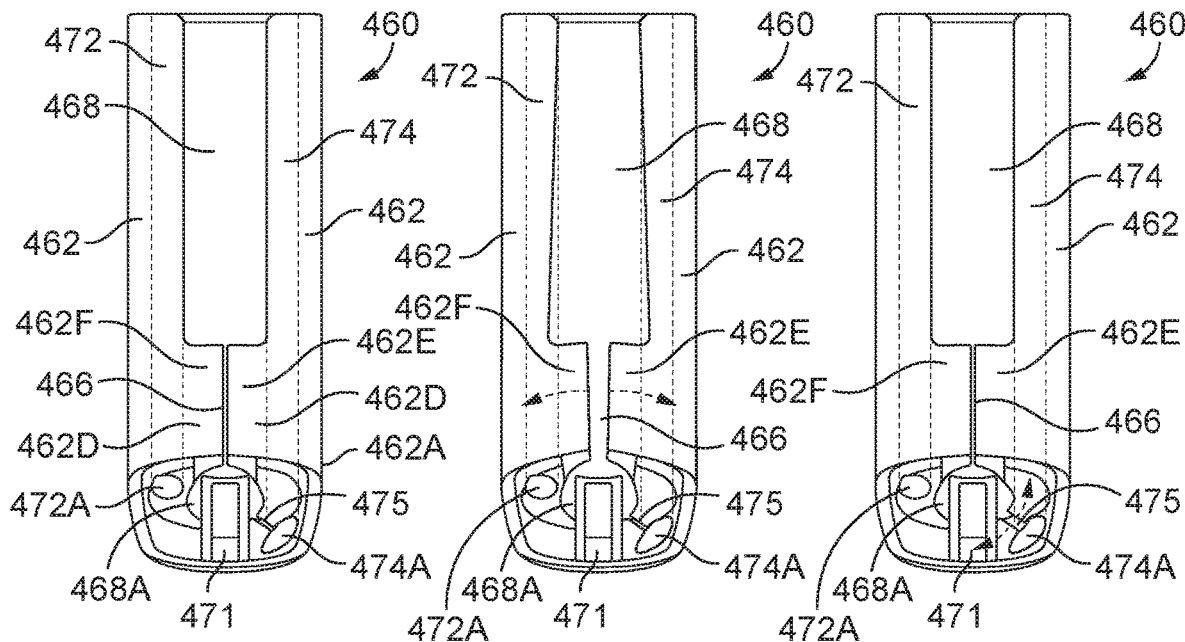
FIG. 1E depicts the distal end of the oral way device of FIG. 1A.
FIG. 1F depicts the distal end of the oral way device of FIG. 1A with the flaps being pushed apart.
FIG. 1G depicts the distal end of the oral way device of FIG. 1A and showing a gap widening in the slit of the esophageal channel.

Referring to FIGS. 1E, 1F and 1G, they are an enlarged view of details at the distal end of the oral airway device 460. The oral airway device 460 is shown in these drawings from the ventral surface 462D.

All elements are labeled in the same way as in connection with FIGS. 1A-1D. In FIG. 1E, one can see the distal opening 472A of the camera channel 472 positioned near the ventral surface 462D of the wall 462. In this embodiment, the camera channel 472 is a passage which is separated from the ETT lumen 468. The distal opening 474A of the esophageal channel 474 is positioned near the dorsal surface 462C of the wall 462. In FIG. 1E, the esophageal channel 474 has the slit 475 which runs along the length of the esophageal channel 474 and which opens the esophageal channel 474 into the ETT lumen 468. This helps in guiding a placement of the oral airway device 460 with a bougie or stylet placed in the esophageal channel 474.

As can be seen from the embodiment of FIG. 1E, the ETT lumen 468 is positioned between the channels 472 and 474. As shown in FIG. 1F, the flaps 462E and 462F can be pushed aside such that a device, such as for example an endotracheal tube, can be loaded into the ETT lumen 468 of the oral airway device 460.

As shown in FIG. 1G, the slit 475 can be also widen to a gap as the wall 462 and/or at least a portion of the channel 474 is made of a flexible material. The slit 475 facilitates a removal of a suction tube or any other tool from the esophageal channel 474.

Figure 1H:
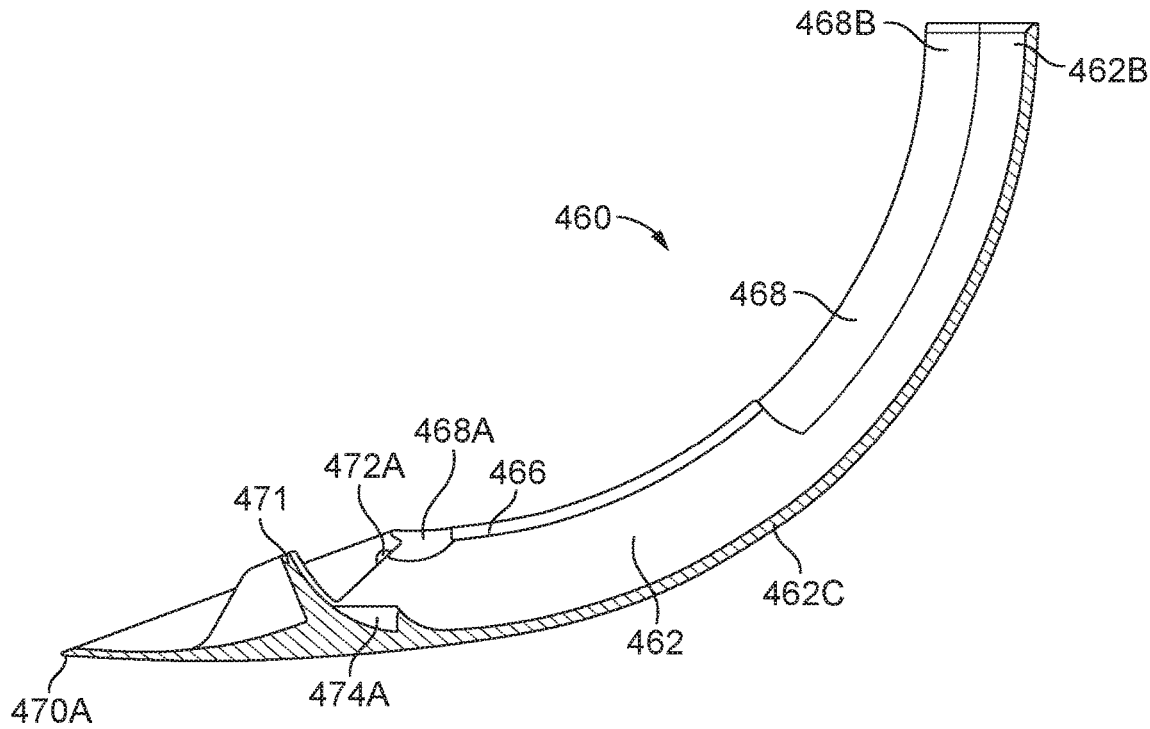
FIG. 1H is a longitudinal section through the oral airway device of FIG. 1A.

FIG. 1H is a longitudinal section through the oral airway device 460. All elements are labeled as in connection with FIGS. 1A-1G.

Figure 1I:
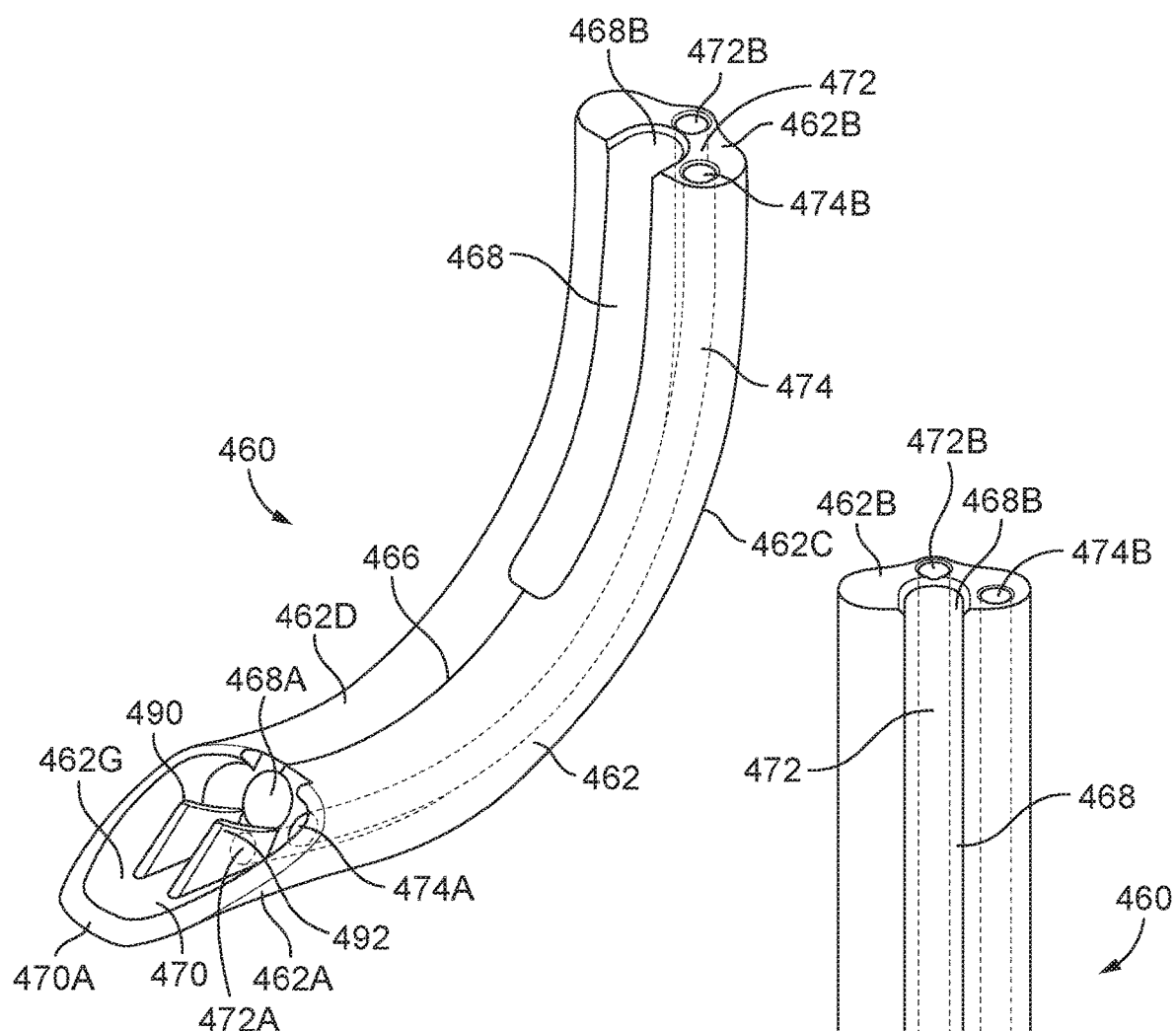
FIG. 1I depicts an oral airway device in which a camera channel is located centrally on the dorsal side of the oral airway device.

FIG. 1I depicts a further embodiment of the oral airway device 460. As was discussed in connection with FIG. 1A, the oral airway device 460 is a tubal body which is curved such that the oral airway device 460 follows the contour of the roof of a patient's mouth during insertion of the device 460 into the patient.

The curved tubal body of the oral airway device 460 is made by a wall 462 with a distal end 462A and a proximal end 462B. The wall 462 is curved along the distal-proximal 462A-462B axis such that the wall 462 follows the contour of the roof of a patient's mouth. The wall 462 creates an arch. The wall 462 has a dorsal surface 462C and a ventral surface 462D. Because of the arch curvature, a length of the wall 462 is longer on the dorsal surface, 462C, than on the ventral surface, 462D. The ventral surface 462D is in contact with the patient's tongue when the oral device 460 is placed in the patient.

The wall 462 has the slit 466 which runs along the distal-proximal 462A-462B axis on the ventral surface 462D. The wall 462 encircles the ETT lumen 468. The ETT lumen 468 is hollow and has a distal opening 468A at the distal end 462A of the wall 462. The ETT lumen 468 has a proximal opening 468B at the proximal end of the wall 462. The slit 466 opens into the ETT lumen 468.

Unlike the embodiment of the drawing of FIG. 1A, the wall 462 in the embodiment of FIG. 1I does not have flaps, but some proximal portion of the ETT lumen 468 is still not covered by the wall 462 on the ventral surface 462D. Accordingly, some portion of the ETT lumen 468 is exposed and this facilitates an insertion and removal of an endotracheal tube into the ETT lumen 468.

At the distal end 462A, the wall 462 ends with a tongue 470 on the dorsal surface 462C. The distal end 470A of the tongue 470 may be an oval or round shape. The tongue 470 is tapered at its distal end 470A. The tongue 470 is used to gently push patient's tissues apart during insertion of the device 460. The tongue 470 protrudes distally from the wall 462.

There is a ramp 490/492 which comprises two blocks, 490 and 492, each attached to the surface of the internal surface 462G of the tongue 470. The ramp 490/492 is sloped and positioned proximally to the tongue 470 and distally to the distal opening 468A of the ETT lumen 468 such that the blocks 490 and 492 flank the distal opening 468A of the ETT lumen 468.

The ramp 490/492 elevates above the surface of the internal side 462G of the wall 462. The function of the ramp 490/492 is to lift and support a distal end of a device loaded in the ETT lumen 468, such as for example an endotracheal tube, above the internal surface 462G.

The wall 462 has at least two hollow channels, 472 and 474. The esophageal channel 474 is a hollow passage with the distal opening 474A and the proximal opening 474B and is positioned in the wall 462, as was described in connection with FIG. 1A.

However, the camera channel 472 is positioned near the central line on the dorsal side 462C of the wall 462 in the embodiment of FIG. 1I. The camera channel 472 is hollow and has a proximal opening 472B at the proximal end 462B of the wall 462. The camera channel 472 runs along the distal-proximal 462A-462B axis of the wall 462. The camera channel 472 ends with a distal opening 472A at the distal end 462A of the wall 462. The distal opening 472A is preferably is not sealed such that a camera can protrude distally from the camera channel 472. In some embodiments, the distal opening 472A is sealed with a transparent material (not shown) such that a camera can capture images through the sealed window while being positioned inside the camera channel 472.

Figure 1J:
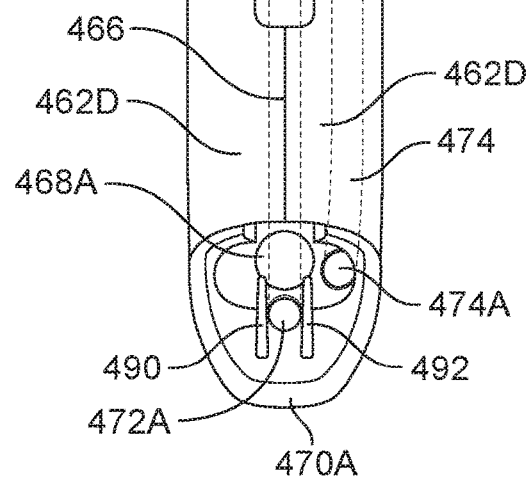
FIG. 1J depicts the oral airway device of FIG. 1I from the ventral surface.

Referring to FIG. 1J, this is a ventral surface view of the oral airway device of FIG. 1I. As can be further seen from the drawing of FIG. 1J, the distal opening 472A of the camera channel 472 is flanked by blocks 490 and 492. Accordingly, when a camera protrudes from the camera channel opening 472A, the blocks 490 and 492 flank the camera and keep it in place. Furthermore, and as can be seen in FIG. 1J, the ETT lumen 468 opens with the distal opening 468A right above the camera lumen opening 472A. Accordingly, when an endotracheal tube is loaded into the ETT lumen 468 and a camera is inserted into the camera channel 472, a distal end of the endotracheal tube protruding from the distal opening 468A of the ETT lumen can be constantly monitored by the camera from the distal opening 472A. This facilitates intubation, including intubation of patients who are difficult to intubate and/or patients with collapsed airways.

Figure 1K:
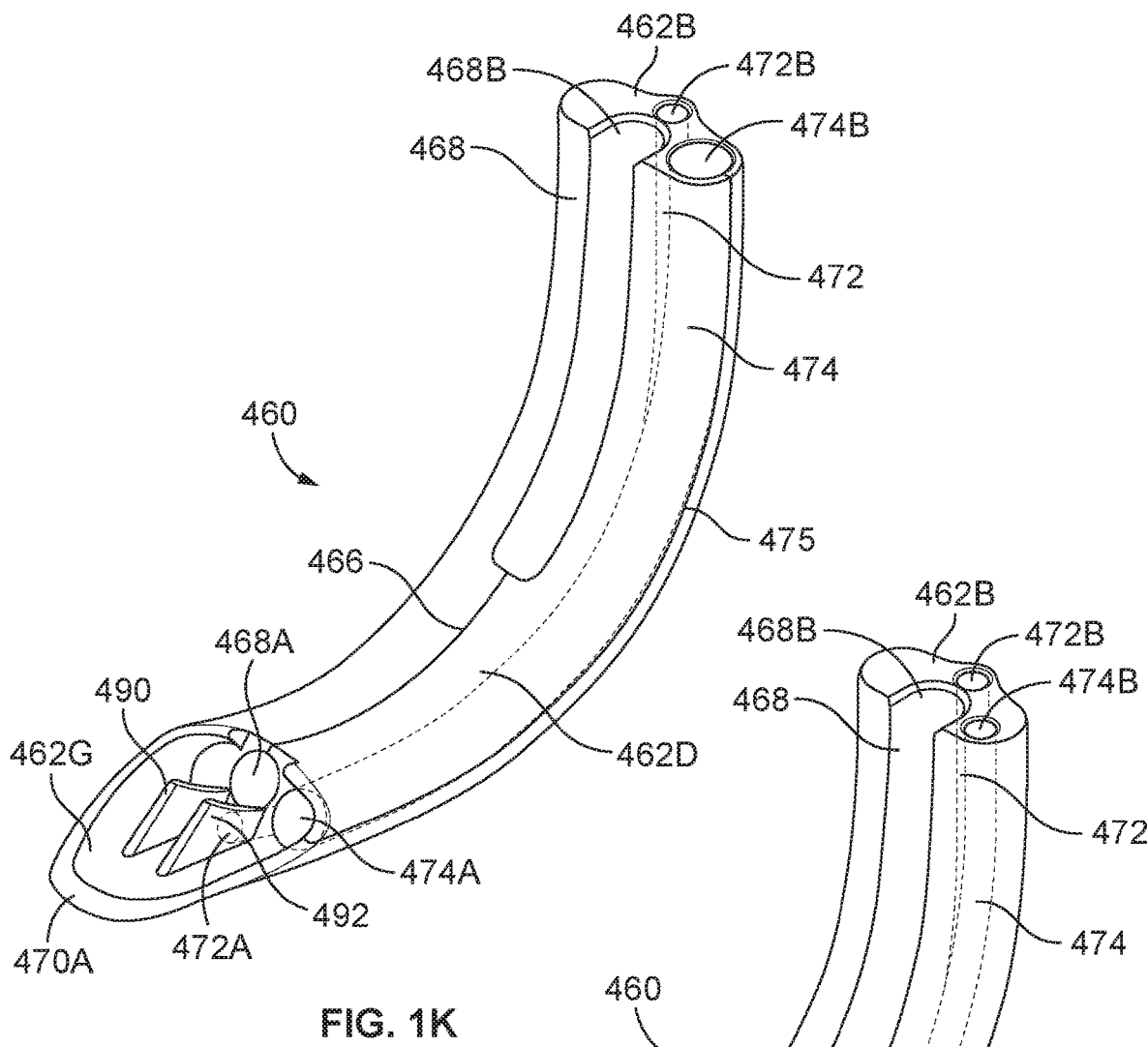
FIG. 1K depicts an oral airway device in which a camera channel is located centrally on the dorsal side of the oral airway device and an esophageal channel comprises a slit.

Referring to FIG. 1K, it depicts a further embodiment of the oral airway device 460 in which the camera channel 472 is positioned near the central line of the dorsal surface 462C of the wall 462, as was discussed in connection with FIG. 1I. In the embodiment of FIG. 1K, the ETT lumen is positioned centrally as determined by the proximity to the central axis of the oral airway device 460.

The esophageal channel 474 is positioned peripherally in one of the flanks 462L or 462R of the wall 462. The esophageal channel 474 comprises the slit 475 which runs externally along the distal-proximal axis 462A-462B in the wall 462. The edges of the wall 462 can be pushed apart along the slit 475 in order to facilitate insertion and removal of a suction tube or any other tool into the esophageal channel 474.

The diameter of the esophageal channel 474 is such that it can accommodate a scope for an upper endoscopy (EGD). Thus, the oral airway device 460 can be used to deliver a scope into the upper digestive tract, while at the same time being used for managing the patient's airways. Accordingly, the oral airway device 460 with the scope compatible esophageal channel can be used for various procedures on esophagus, stomach and/or the duodenum.

Figure 1L:
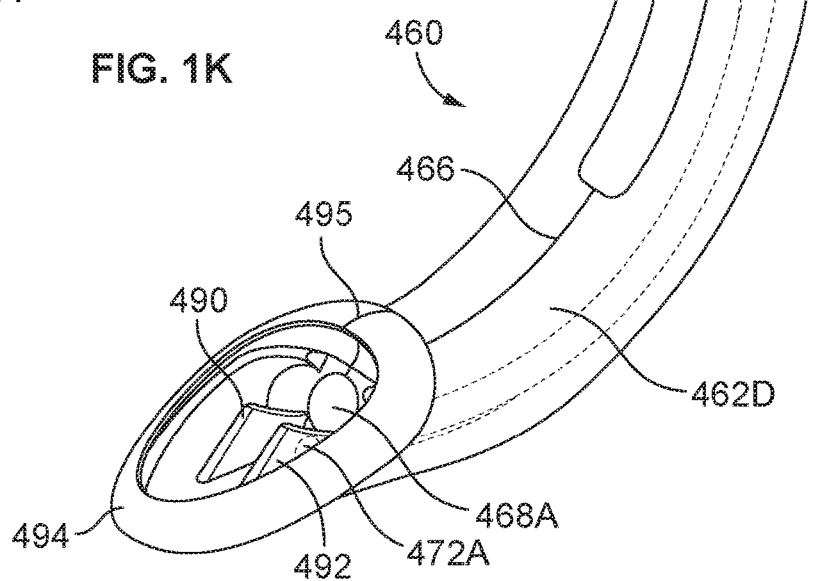
FIG. 1L depicts the oral airway device of FIG. 1I which comprises a non-inflatable cuff.

Referring to FIG. 1L, it provides a further embodiment of the oral airway device 460 in which the oral airway device 460 ends with a distal, soft and non-inflatable cuff 494.

The oral airway device 460 in this embodiment of FIG. 1L comprises the camera channel 472 located near the central line of the dorsal surface 462C of the wall 462, as was discussed in connection with FIGS. 1I and 1J. It will be appreciated, that any of the embodiments for the oral airway device 460 may end with the distal soft non-inflatable cuff 494.

In the embodiment of FIG. 1L, the soft non-inflatable distal cuff 494 is attached around the perimeter of the distal end 462 and the tongue tip 470A. Notably, the oral airway device 460 comprises the slit 466 in the wall 462 on its ventral surface 462D. The slit 466 opens into the ETT lumen 468. The cuff 494 has a slit 495 which is aligned with the slit 466. Thus, the wall 462 and the cuff 494 can be pushed apart at the slits 466 and 495 in order to insert an endotracheal tube or some other breathing tube into the ETT lumen 468.

The soft non-inflatable distal cuff 492 softens an impact of the oral airway device 460 on the patient's tissues during insertion. The soft non-inflatable cuff 492 also helps with occluding the patient's pharynx and establishing a closed system for ventilation.

Figure 1M:
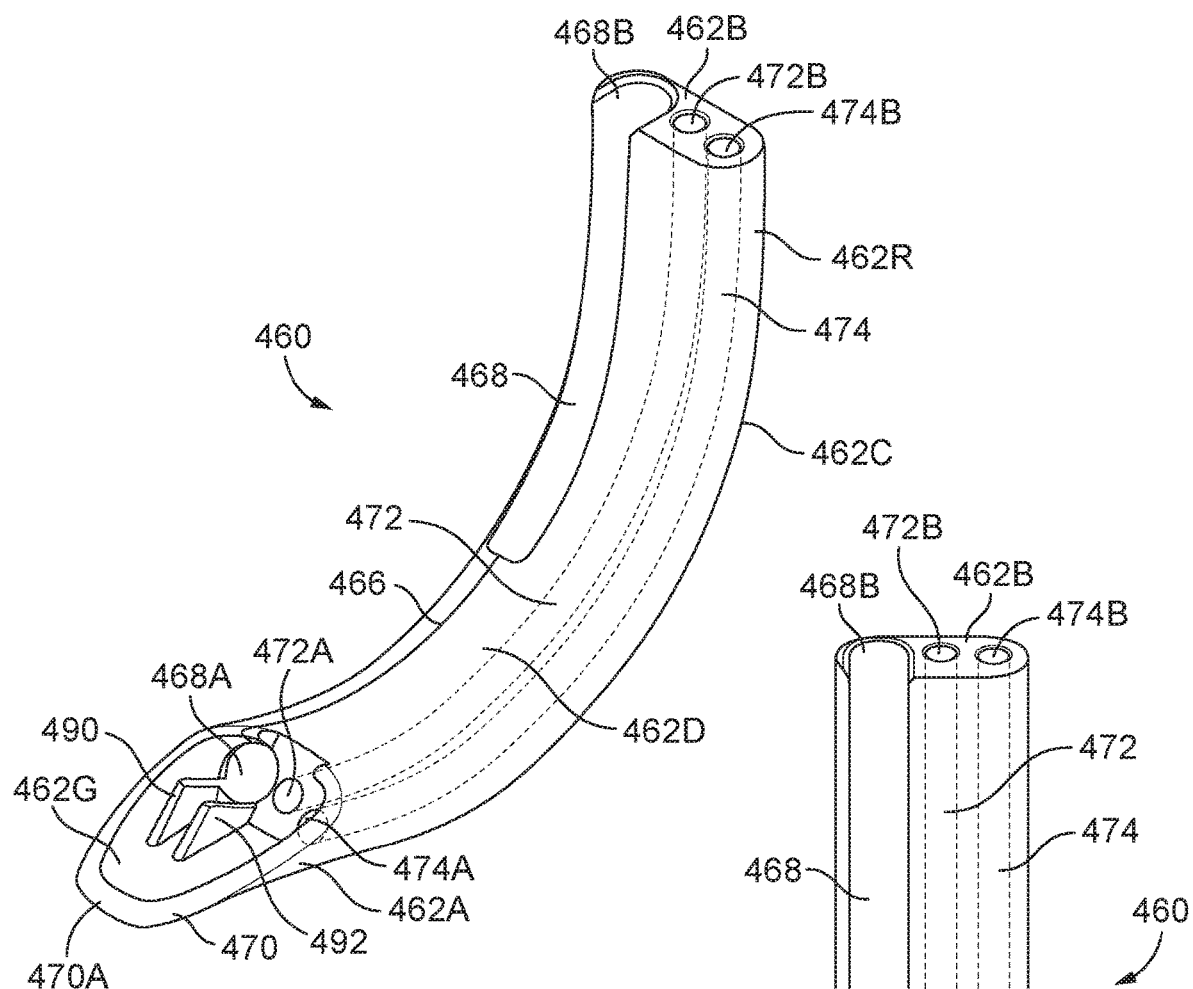
FIG. 1M depicts an oral airway device which comprises a central camera channel and peripheral ETT lumen.

Referring to FIG. 1M, it provides a further embodiment of the oral airway device 460. As was discussed in connection with FIGS. 1A-1L, the oral airway device 460 is a tubal body which is curved such that the oral airway device 460 follows the contour of the roof of a patient's mouth during insertion of the device 460 into the patient.

The curved tubal body of the oral airway device 460 is made by the wall 462 with the distal end 462A and the proximal end 462B. The wall 462 is curved along the distal-proximal 462A-462B axis such that the wall 462 follows the contour of the roof of a patient's mouth. The wall 462 creates an arch. The wall 462 has a dorsal surface 462C and a ventral surface 462D. Because of the arch curvature, a length of the wall 462 is longer on the dorsal surface, 462C, than on the ventral surface, 462D.

The ventral surface 462D is in contact with the patient's tongue when the device 460 is placed in the patient. In FIG. 1M, the ventral surface 462D and the right flank 462R are shown.

In the embodiment of FIG. 1M, the camera channel 472 is positioned centrally or near the central axis of the oral airway device 460. The camera channel 472 has the distal opening 472A and the proximal opening 472B. A camera can be inserted and slid along the camera channel 472. The camera can protrude distally from the distal opening 472A of the camera channel 472.

The wall 462 encircles the ETT lumen 468 which is positioned peripherally from the central location of the camera channel 472. Some proximal portion of the ETT lumen 468 is not covered by the wall 462 on the ventral surface 462D. Accordingly, some proximal portion of the ETT lumen 468 is exposed which facilitates insertion and removal of an endotracheal tube into the ETT lumen 468.

Just like in connection with other embodiments of the oral airway device 460, the wall 462 comprises the slit 466 which runs along the distal-proximal axis 462A-462B. The slit 466 is positioned over the ETT lumen 468 and opens into the ETT lumen 468. The edges of the wall 462 can be pushed apart along the slit 466. This facilitates a loading into and removal of an endotracheal tube from the ETT lumen 468. In the embodiment of FIG. 1M, the slit 466 is positioned on the ventral surface 462D of the wall 462. In other embodiments, the slit 466 may be positioned on a flanking surface—between the ventral surface 462D and the dorsal surface 462C or on the dorsal surface 462C.

The ETT lumen 468 is hollow and has the distal opening 468A at the distal end 462A of the wall 462. The ETT lumen 468 has the proximal opening 468B at the proximal end of the wall 462.

At the distal end 462A, the wall 462 ends with the tongue 470 on the dorsal surface 462C. The distal end 470A of the tongue 470 may be an oval or round shape. The tongue 470 is tapered at its distal end 470A. The tongue 470 is used to gently push patient's tissues apart during insertion of the oral airway device 460. The tongue 470 protrudes distally from the wall 462.

The esophageal channel 474 is positioned peripherally to the camera channel 472 and can be used with various tools, as discussed in connection with other embodiments.

There is a ramp which comprises two blocks, 490 and 492, each attached to the surface of the internal surface 462G. The ramp 490/492 is positioned proximally to the tongue 470 and distally to the distal opening 468A of the ETT lumen 468 such that the blocks 490 and 492 flank the distal opening 468A and guide an endotracheal tube when it is protruding from the distal opening 468A of the ETT lumen 468.

Figure 1N:
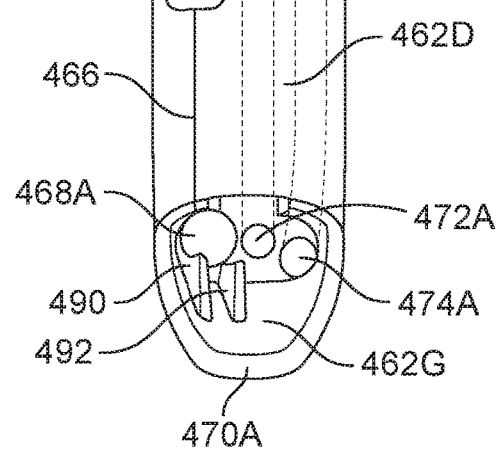
FIG. 1N depicts the oral airway device of FIG. 1M from the ventral surface.

As can be further seen from the drawing of FIG. 1N which depicts the device 460 of the drawing 1M from the ventral surface, the distal opening 468A of the ETT lumen 468 is flanked by blocks 490 and 492 which are tilted somewhat toward the center of the internal surface 462G. Accordingly, the blocks 490 and 492 guide a distal end of an endotracheal tube toward the center of the tongue 470. This brings a distal portion of the endotracheal tube under continuous visualization from a camera through the distal opening 472A of the camera channel 472.

In the embodiments of FIGS. 1M and 1N, the esophageal channel 474 is located peripherally to the camera channel 472. As can be seen from the drawing 1N, the distal end 474A of the esophageal channel 474 opens in near proximity to the distal opening 472A of the camera channel 472. Accordingly, if a tool is inserted into the esophageal channel 474, such as for example a stylet or bougie, the tool can be operated under continuous visualization from a camera inserted into the camera channel 472 and vice versa, a camera can be positioned in the esophageal channel 474 and a tool can be placed in the camera channel. If needed, two cameras can be used, on in the esophageal channel 474 and the other one in the camera channel 472.

Figure 1O:
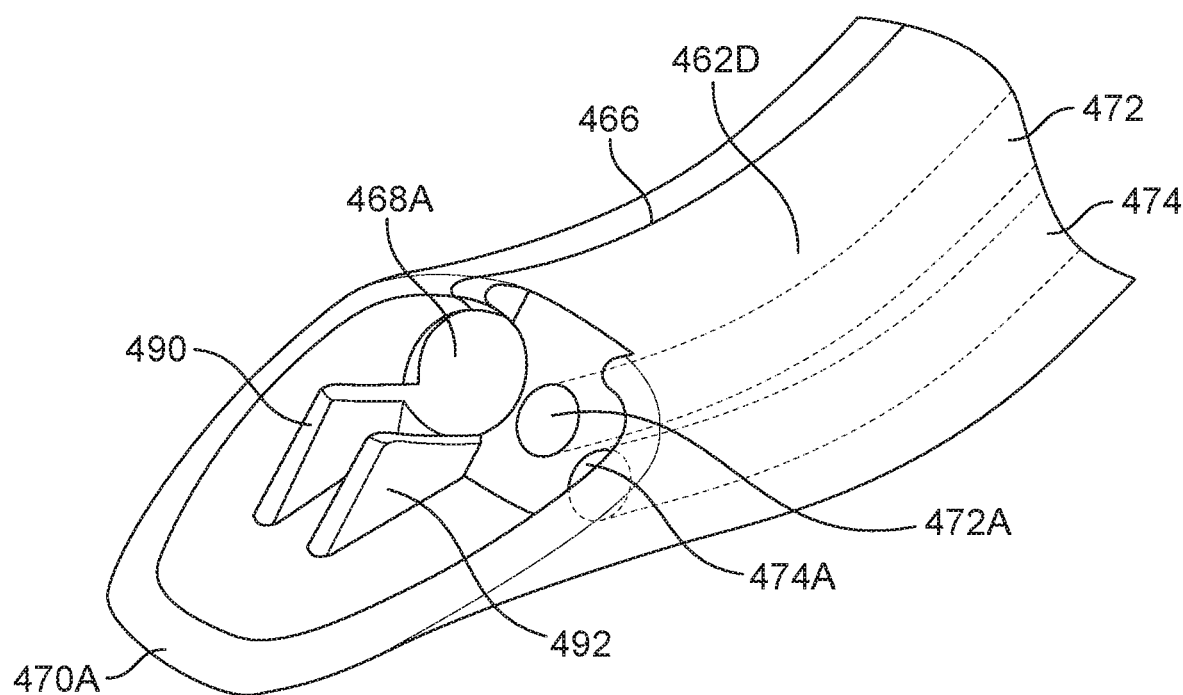
FIG. 1O depicts a distal portion of the oral airway device of FIG. 1M.

Referring to FIG. 1O, it is a zoomed view of a distal portion of the oral airway device 460 of the FIG. 1M. The distal opening 468A of the ETT lumen 468 is shown. The slit 466 provides access to the ETT lumen 468. The blocks 490 and 492 flank the distal opening 468A and elevate/guide an endotracheal tube (not shown) when loaded in the ETT lumen 468.

Figure 1P:
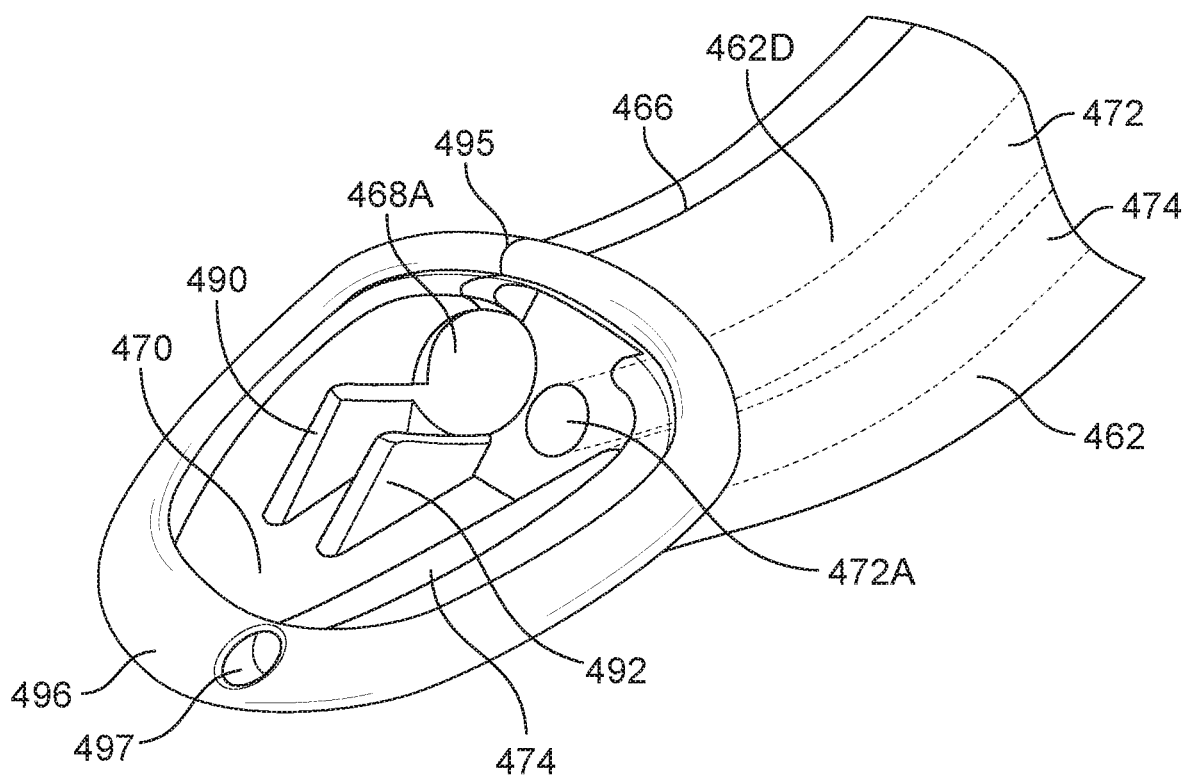
FIG. 1P depicts a distal portion of the oral airway device of FIG. 1M which further comprises a distal cuff and an extended esophageal channel.

Referring to FIG. 1P, it is a zoomed view of a distal portion of the oral airway device 460 as was discussed in connection with FIGS. 1M-1O, except the embodiment of FIG. 1P comprises a soft non-inflatable cuff 496 which is attached around the perimeter of the distal end 462A and the tongue 470 of the curved body of the oral airway device 460. The cuff 496 comprises a slit 495 which is aligned with the slit 466 in the wall 462. This allows pushing the cuff 496 and the wall 462 apart for loading an endotracheal tube into and its removal from the ETT lumen 468. In the embodiment of the FIG. 1P, the esophageal channel 474 is extended through the tongue 470 and through the cuff 496 which comprises an opening 497 which holds in place a suction tube or any other tool inserted into the esophageal channel 474. Thus, a suction tube or any other tool can protrude distally from the cuff 496 and prevent accumulation of fluids on the tongue 470 and behind the cuff 496, which otherwise may require a removal and replacement or cleaning of the oral airway device 460.

It will be appreciated that while in the embodiment of FIG. 1P, the distal cuff 496 is not inflatable, it may be inflatable in other embodiments. In further embodiments, the cuff 496 does not have the slit 495.

Figure 1Q:
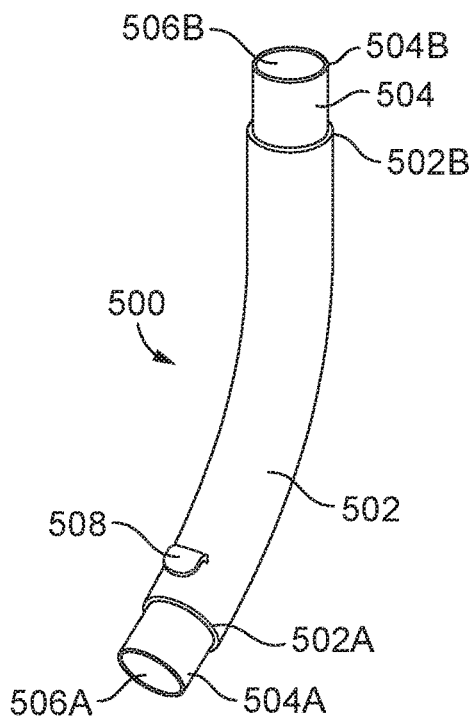
FIG. 1Q is a device insertable into the oral airway device of FIGS. 1A and 1B.

FIG. 1Q depicts an adaptor, generally 500, which can be loaded into the ETT lumen 468 of the oral airway device 460 or some other oral airway device. The adaptor 500 comprises two hollow tubes, an outer tube 502, and inner tube 504, the inner tube 504 being insertable and removable from the outer tube 502. The tubes 502 and 504 are either made curved to fit the shape of the lumen 468 of the oral airway device 460 or the tubes 502 and 504 are made of a flexible material such that they can assume the curved shape once inserted or prior to being inserted into the ETT lumen 468 of the oral airway device 460.

The inner tube 504 is longer in length than the outer tube 502. As shown in FIG. 1Q, a distal end 504A of the inner tube 504 protrudes distally from the distal end 502A of the outer tube 502. A proximal end 504B of the inner tube 504 protrudes proximally from the proximal end 502B of the outer tube 502.

The inner tube 504 is insertable into and removable from the outer tube 502. Accordingly, the length of the adaptor 500 can be adjusted as needed by having a longer or shorter portion of the inner tube 504 protruding proximally from the outer tube 502. The outer tube 502 and the inner tube 504 are hollow. The inner tube 504 has a central lumen 506 that has a proximal opening 506B and a distal opening 506A. If the inner tube 504 is removed from the outer tube 502, a central lumen of the outer tube 502 can be also used for inserting other devices.

The outer tube 502 may comprise a latch 508 located near the distal end 502A.

Figure 1R:
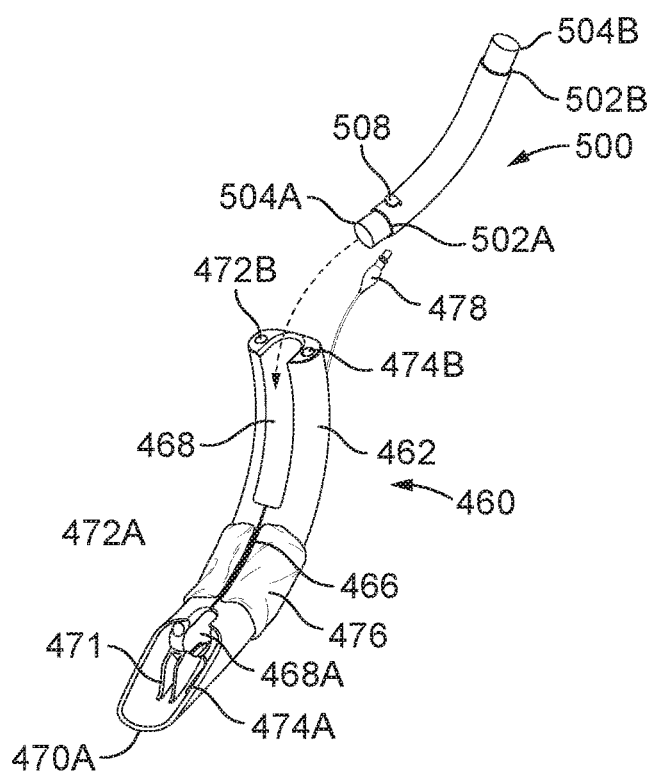
FIG. 1R depicts loading the device of FIG. 1Q onto the oral airway device of FIG. 1B.

FIG. 1R depicts loading of the adaptor 500 into the ETT lumen 468 of the oral airway device 460. All elements are labeled as in connection with drawings 1A-1Q.

Figure 1S:
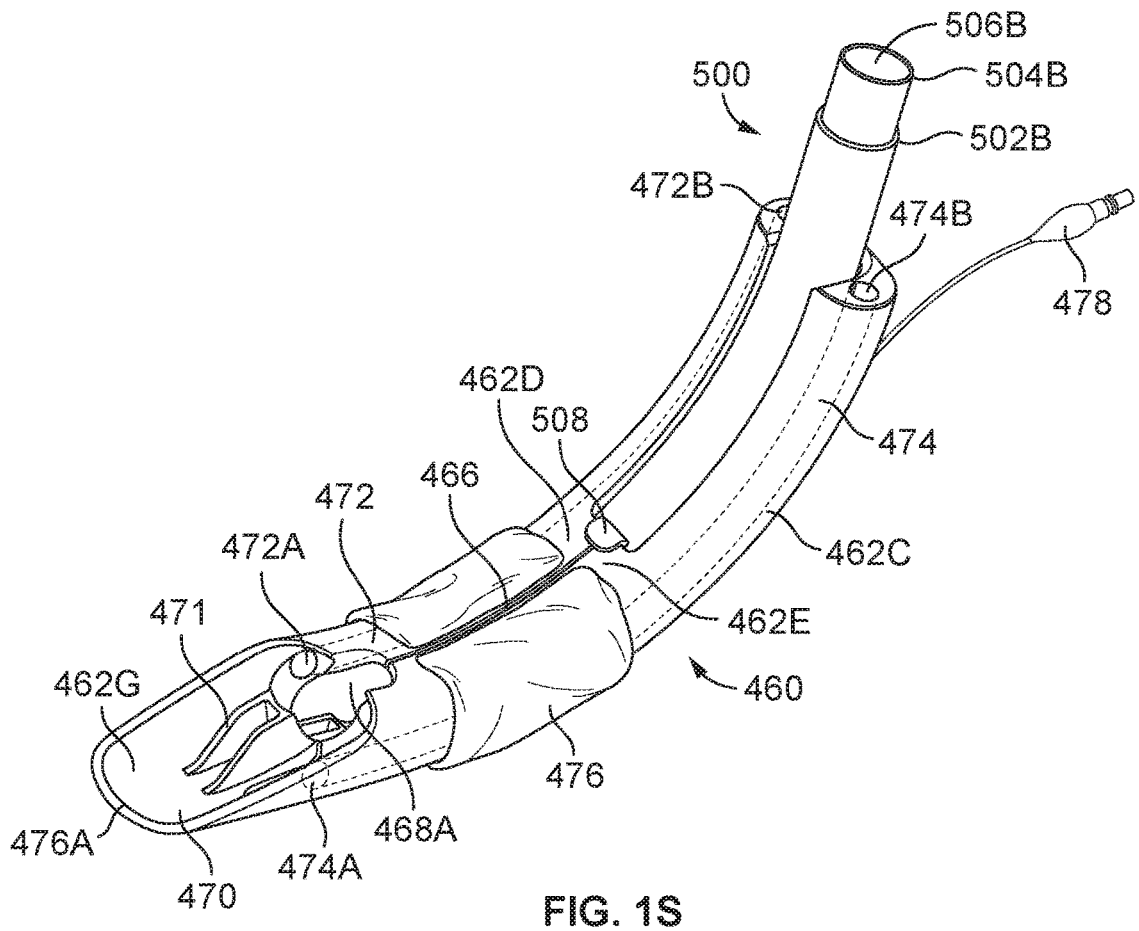
FIG. 1S depicts the device of FIG. 1Q loaded onto the oral airway device of FIG. 1B.

Referring to FIG. 1S, it depicts the adaptor 500 inserted in the ETT lumen 468 of the oral airway device 460. The latch 508 of the adaptor 500 is positioned over the proximal ends of the flaps 462F and 462E and the proximal end of the slit 466. Accordingly, the latch 508 holds the flaps 462D and 462E together and prevents the slit 466 from widening into a gap. This is helpful when the cuff 476 is to be inflated in a patient as the adaptor 500 prevents the slit 466 from widening into a gap. Accordingly, a closed system can be established with the cuff 476 and ventilation can be established.

Figures 1T, 1U, 1V:
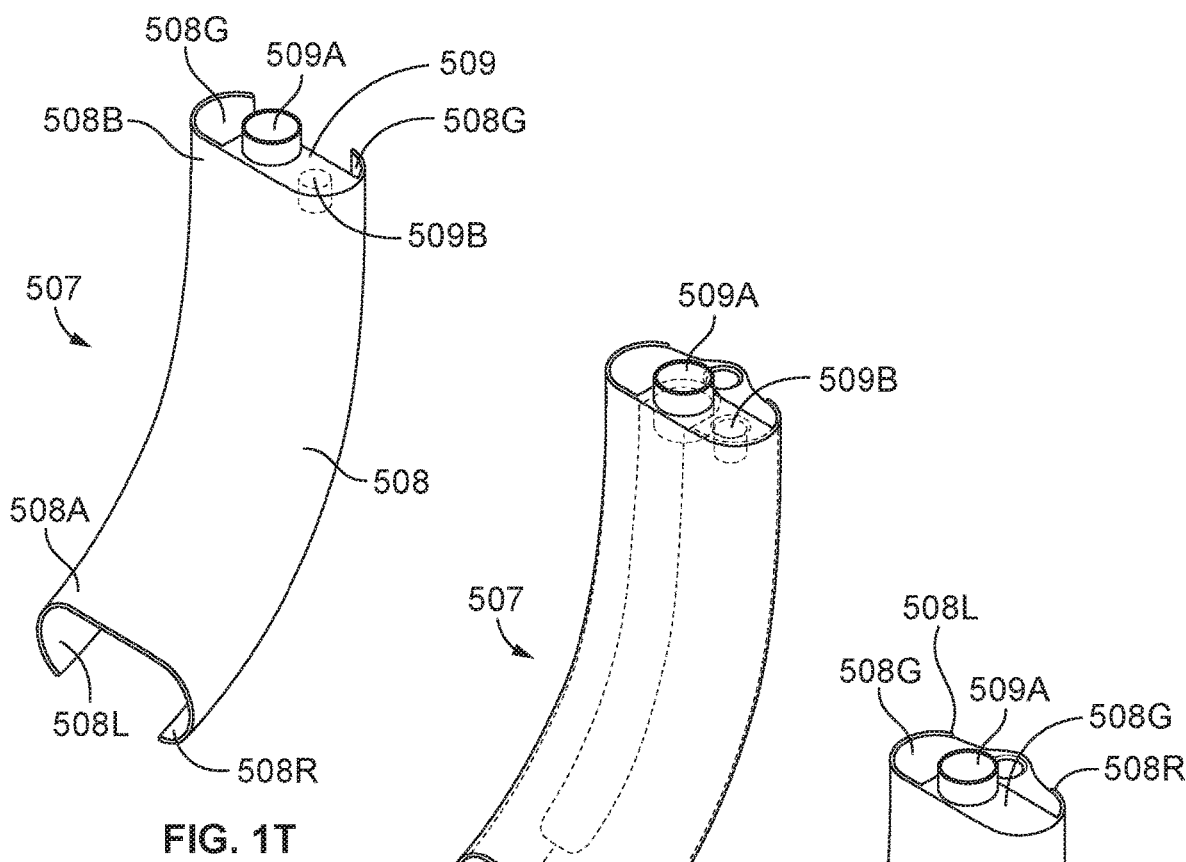
FIG. 1T depicts a ventilator adaptor for an oral airway device with a slit.
FIG. 1U depicts the ventilator adaptor of FIG. 1T placed over the oral airway device with the slit.
FIG. 1V depicts another embodiment of the ventilator adaptor for an oral airway device with a slit.

Referring to FIG. 1T, it depicts a ventilation adaptor, generally 507. The ventilation adaptor 507 is a lid which can be used in order to establish a closed system in the oral airway device 460 with a slit and in order to connect the oral airway device 460 to a ventilator.

The ventilation adaptor 507 comprises a flat panel 508 with a distal edge 508A and a proximal edge 508B opposing the distal edge 508A. The flat panel 508 has a first longitudinal edge 508L and a second longitudinal edge 508R which opposes the first longitudinal edge 508L. The flat panel 508 is curved inwards along the longitudinal edges 508L and 508R such that there is a groove 508G along the longitudinal edge 508L and also there is a matching groove 508G along the longitudinal edge 508R. At or near the distal edge 508B, the flat panel 508 is attached to a flat panel 509. The flat panel 509 is positioned generally perpendicularly to the flat panel 508. The flat panel 509 comprises a conduit 509A which can be used for connecting the ventilation adaptor 507 to a ventilator.

As can be seen from the drawings of FIGS. 1U and 1V, the ventilation adaptor 507 fits tightly over the oral airway device 460 with the conduit 509A fitting over the proximal opening 468B of the ETT lumen 468. The flanks of the oral airway device 460 fit within the grooves 508Gs. Thus, the ventilation adaptor 507 keeps the slit 466 from coming apart. The ventilation adaptor 507 seals the oral airway device 460 and establishes a closed system in the oral airway device 460. A patient can then be ventilated through the conduit 509A which is connected to the ETT lumen 468.

In some embodiments, the ventilator adaptor 507 may comprise a second conduit 509B which is aligned with the proximal opening 474B of the esophageal channel 474.

Figure 2:
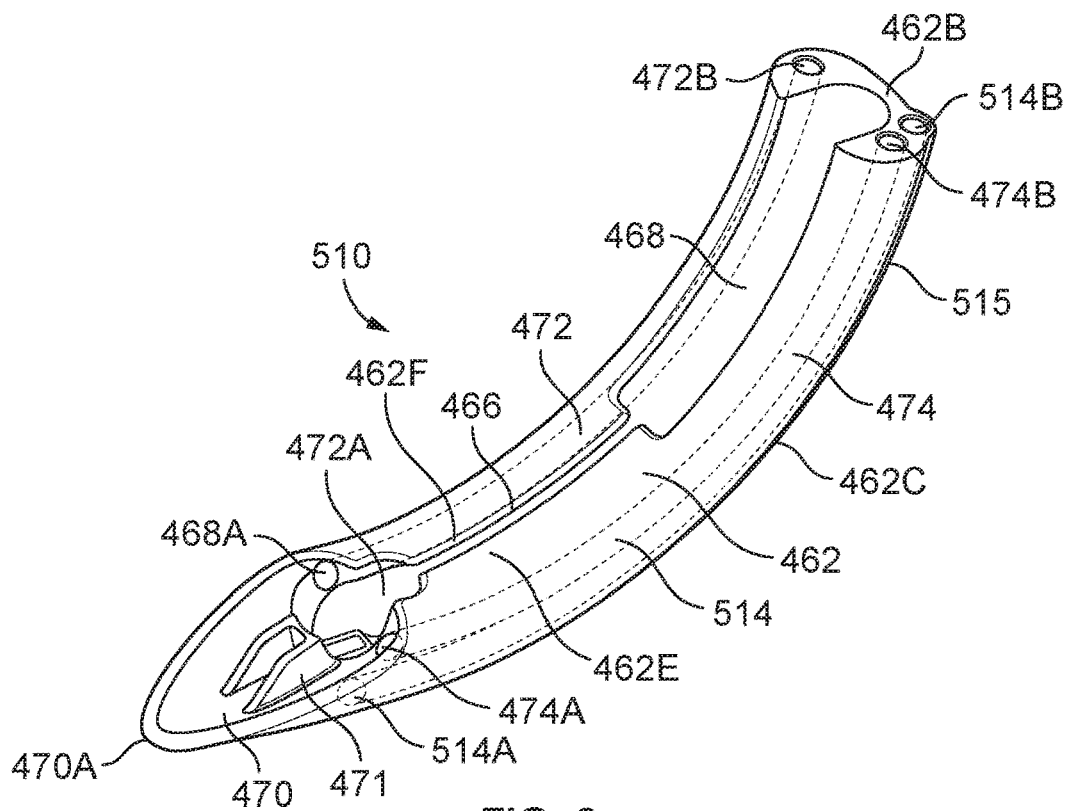
FIG. 2 depicts an oral airway device with three peripheral channels.

Referring to FIG. 2, it provides a further embodiment of an oral airway device, generally 510.

Just like the oral airway device 460, the oral airway device 510 has a tubal body created by the wall 462 which is curved as was discussed in connection with the device 460. All elements that are similar between devices 460 and 510 are labeled with the same numbers. Just like the oral airway device 460, the oral airway device 510 comprises channels 472 and 474. The camera channel 472 is located in the wall 460 peripherally to the ETT lumen 468 which is located centrally in the oral airway device 510. The camera channel 472 has the proximal opening 472B and the distal opening 472A. As discussed in connection with the device 460, a camera can be inserted and removed from the camera channel 472, as needed.

The channel 474 in the oral airway device 510 comprises the proximal opening 474B and the distal opening 474A. A tool, such as for example, a stylet or bougie can be inserted into the channel 474. The tool can be used under continuous visualization from the camera that is protruding distally from the distal opening 472A of the camera channel 472.

The camera channel 472 and the channel 474 are positioned peripherally to the ETT lumen 468.

As shown in FIG. 2, in the oral airway device 510, there is an additional peripheral channel 514 in the wall 462. The channel 514 is positioned on the dorsal surface 462C of the wall 462, but off center of the dorsal surface 462C. The channel 514 has a slit 515 which runs along the length of the channel 514. The slit 515 opens the channel 514 on the dorsal surface 462C of the wall 462. The channel 514 can be used for inserting a suction tube that can be used for aspirating stomach fluids. Other tools may be also loaded into the channel 514 as needed. The channel 514 opens up with a proximal opening 514B on the proximal end 462B of the wall 462. A suction tube or any other tool as needed may be inserted into the channel 514 through the proximal opening 514B. The length of the channel 514 may vary. The dorsal surface 460C of the wall 462 in the device 510 is arched as was described in connection with the device 460. In some embodiments, the channel 514 ends at the highest point of the arch. In other embodiment, the channel 514 may end at any other location on the dorsal surface 462C of the wall 462. As shown in FIG. 2, the channel 514 may extend dorsally into the tongue 470.

Figure 3A:
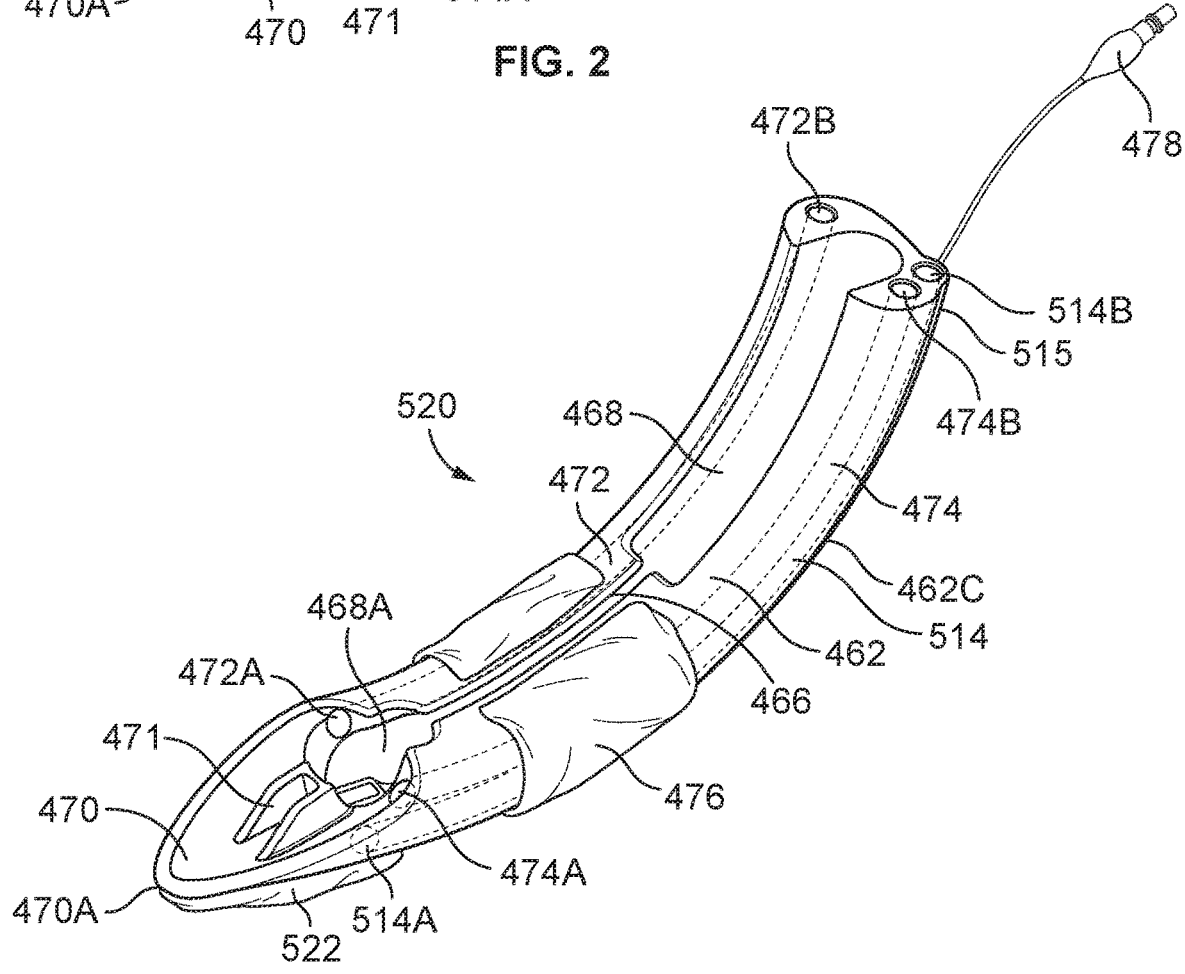
FIG. 3A depicts an oral airway device with three peripheral channels and an inflatable cuff.

Referring to FIG. 3A, it provides another embodiment of an oral airway device, generally 520. The oral airway device 520 comprises the same elements as was discussed in connection with the oral airway device 510 of FIG. 2, except the oral airway device 520 also comprises an inflatable cuff 476. The inflatable cuff 476 is the same inflatable cuff 476 as was described in connection with the device 460 in FIG. 1B. The inflatable cuff 476 can be inflated with a means 478. The oral airway device 520 also comprises a soft non-inflatable cuff 522 that covers the tongue 470 on the dorsal surface 462C of the oral airway device 520. One function of the non-inflatable cuff 522 is to cushion a contact between the tongue 470 and patient's tissues during an insertion of the oral airway device 520.

Figure 3B:
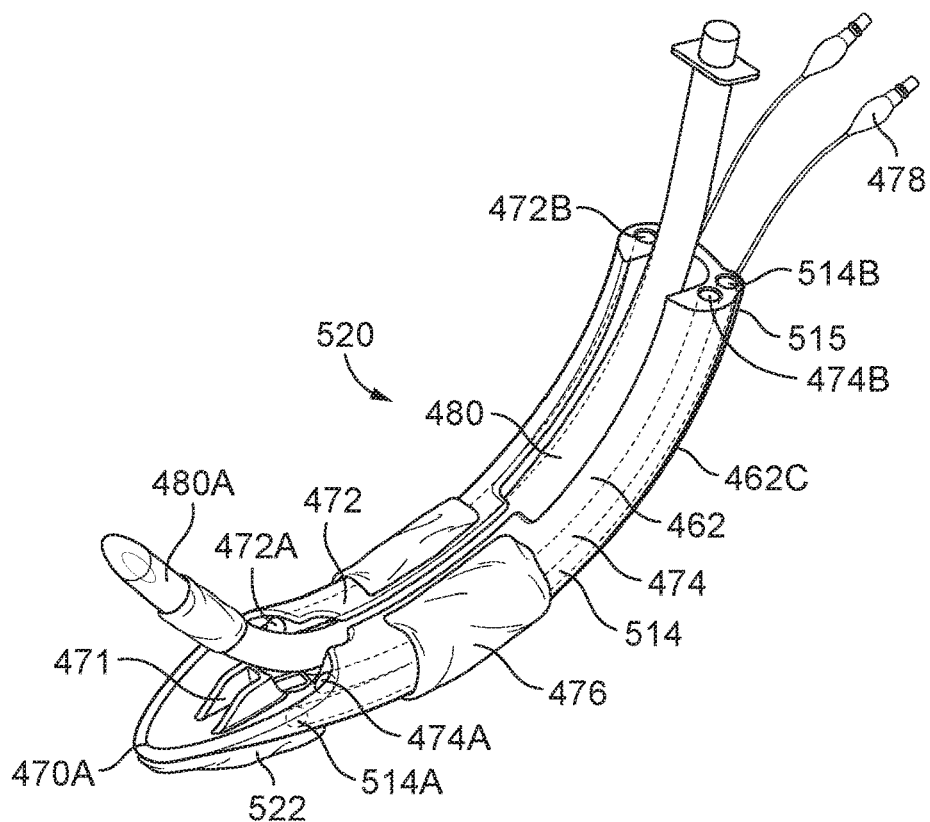
FIG. 3B depicts an endotracheal tube loaded into the oral airway device of FIG. 3A.

Referring to FIG. 3B, it depicts the endotracheal tube 480 loaded in the ETT lumen 468 of the device 520. In FIG. 3B, all elements of the oral airway device 520 as were described in connection with FIG. 3A.

Figure 3C:
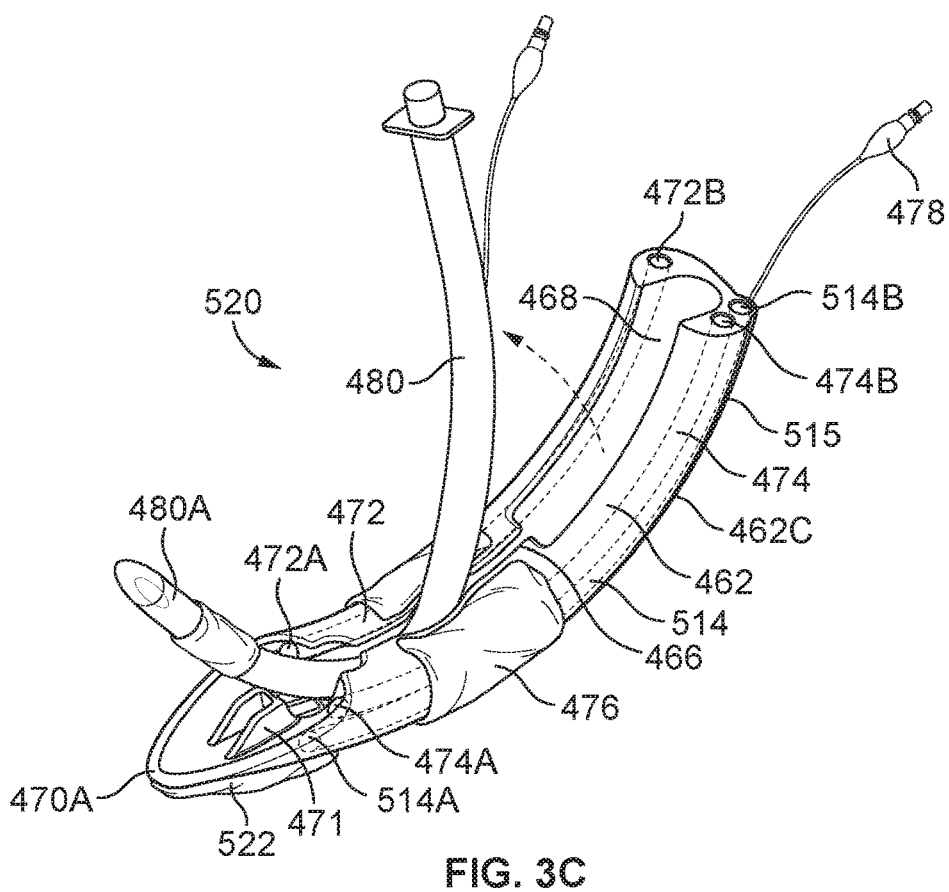
FIG. 3C depicts an endotracheal tube in a process of being removed from the oral airway device of FIG. 3A.

Referring to FIG. 3C, it depicts a removal of the endotracheal tube 480 from the oral airway device 520. The endotracheal tube 480 can be removed from the ETT lumen 468 by pulling the endotracheal tube 480 out through the slit 466. All elements are labeled as in connection with FIGS. 3A-3B.

Figure 4A:
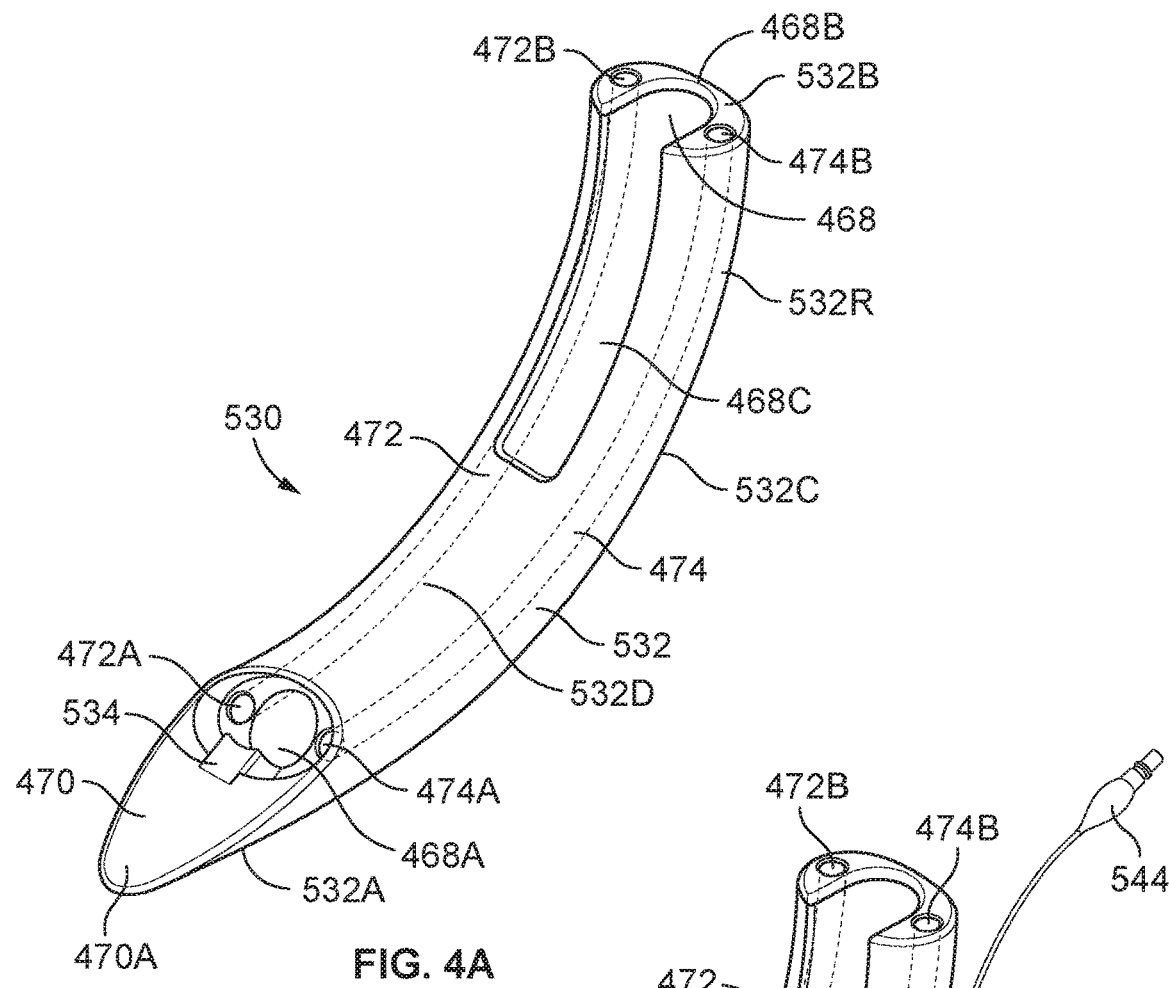
FIG. 4A depicts another embodiment of an oral airway device according to this disclosure.

Referring to FIG. 4A, it depicts another embodiment of an oral airway device provided by this disclosure, generally 530. The oral airway device 530 is a tubal body which is curved such that the oral airway device 530 follows the contour of the roof of a patient's mouth during insertion of the device 530 into the patient.

The curved tubal body of the airway device 530 is made by a wall 532 with a distal end 532A and a proximal end 532B. The wall 532 is curved along the distal-proximal 532A-532B axis such that the wall 532 follows the contour of the roof of a patient's mouth. The wall 532 creates an arch. The wall 532 has a dorsal surface 532C and a ventral surface 532D shown in FIG. 4A along with a right flank 532R. As will be appreciated by a person of skill, because of the arch curvature, a length of the wall 532 is longer on the dorsal surface, 532C, than on the ventral surface, 532D. The ventral surface 532D is in contact with the patient's tongue when the oral airway device 530 is placed in the patient.

The wall 532 encircles the ETT lumen 468. The ETT lumen 468 is hollow and has a distal opening 468A. The ETT lumen 468 has a proximal opening 468B at the proximal end of the wall 532.

The wall 532 recesses into the ETT lumen 468 on the ventral surface 532D such that some proximal portion 468C of the ETT lumen 468 is open and is not covered by the wall 532 on the ventral surface 532D. In this embodiment, there is no slit 466 along the ventral surface 532D of the wall 532. Instead, some proximal portion 468C of the ETT lumen 468 is not covered by the wall 532. This facilitates a loading and removal of a medical device, such as an endotracheal tube, into and from the ETT lumen 468.

At the distal end 532A, the wall 532 ends with a tongue 470 on the dorsal surface 532C. The distal end 470A of the tongue 470 may be an oval or round shape and is tapered at its distal end 470A. The tongue 470 is used to gently push patient's tissues apart during insertion of the oral airway device 530. The tongue 470 protrudes distally from the wall 532.

There is a ramp 534 positioned proximally to the tongue 470 and distally to the distal opening 468A. The ramp 534 elevates and supports a distal end of a device, such as for example an endotracheal tube, inserted into the ETT lumen 468.

The wall 532 has at least two hollow peripheral channels, 472 and 474. The camera channel 472 is hollow and is positioned peripherally to the ETT lumen 468. The camera channel 472 has a proximal opening 472B at the proximal end 532B of the wall 532. The camera channel 472 runs along the distal-proximal 532A-532B axis of the wall 532. The channel 472 ends with a distal opening 472A at the distal end 532A of the wall 532.

A camera (not shown) can be inserted through the proximal opening 472B in the channel 472. The camera can protrude from the distal opening 472A of the channel 472. Any camera described in this disclosure or generally known in the art can be used in the oral airway device 530. The camera is insertable and removable from the camera channel 472. A position of the camera at the distal opening 472A of the camera channel 472 can be adjusted as needed in order to monitor patient's tissues and/or insertion of the oral airway device 530.

In some embodiments, the camera channel 472 is a hollow passage in the wall 532 and the camera channel 472 is completely separated from the ETT lumen 468. In other embodiments, the camera channel 472 is a semi-lumen which is connected to the ETT lumen 468. In further embodiments, there is a slit (not shown in the drawing) that runs along the length of the camera channel 472. The slit of the channel 472 may run along the wall 532 and open externally on the wall 532. A camera can be easily inserted and removed from the camera channel 472 by being pulled through the slit.

The structure of the second channel, 474, is similar to the structure of the first channel 472. The channel 474 is a peripheral hollow channel. The channel 474 runs along the distal-proximal 532A-532B axis of the wall 532. The channel 474 is located peripherally to the ETT lumen 468. As can be seen in FIG. 4A, the channels 472 and 474 flank the ETT lumen 468 which is positioned between the channels 472 and 474.

The channels 472 and 474 may have the same diameter or they may be of a different diameter.

The esophageal channel 474 ends with a distal opening 474A at the distal end 532A of the wall 532. A tool, such as for example a suction tube, (not shown) can be inserted through the proximal opening 474B in the esophageal channel 474. The suction tube (or any other tool inserted in the esophageal channel 474) can protrude from the distal opening 474A of the esophageal channel 474. Any tools described in connection with other embodiments of this disclosure can be used in the oral airway device 530.

The tools are insertable and removable from the esophageal channel 474. A position of the tool at the distal opening 474A can be adjusted as needed in order to manipulate patient's tissues or provide suction. In some embodiments, the esophageal channel 474 is a passage in the wall 432 and the esophageal channel 474 is completely separated from the ETT lumen 468. In other embodiments, the esophageal channel 474 is a semi-lumen which is connected to the ETT lumen 468. In further embodiments, there is a slit that runs along the length of the esophageal channel 474. The slit opens into the ETT lumen 468 or the slit opens the esophageal channel 474 externally on the wall 532.

A relative positioning of the channels 472 and 474 is such that when a camera is inserted in the camera channel 472 and protrudes from the distal opening 472A of the camera channel 472, the camera can visualize a distal end of a tool inserted into the esophageal channel 474 and protruding from the distal opening 474A of the esophageal channel 474. Accordingly, manipulations of the tool are visualized with the camera.

As can be appreciated by a person of skill, in some embodiments, the channels 472 and 474 may be interchangeable, i.e. a camera can be inserted into either of the two channels, as needed, or two cameras can be used simultaneously. In further embodiments, the oral airway device 530 may have more than two channels in the wall 532. These additional channels may be located peripherally to the ETT lumen 468.

Figure 4B:
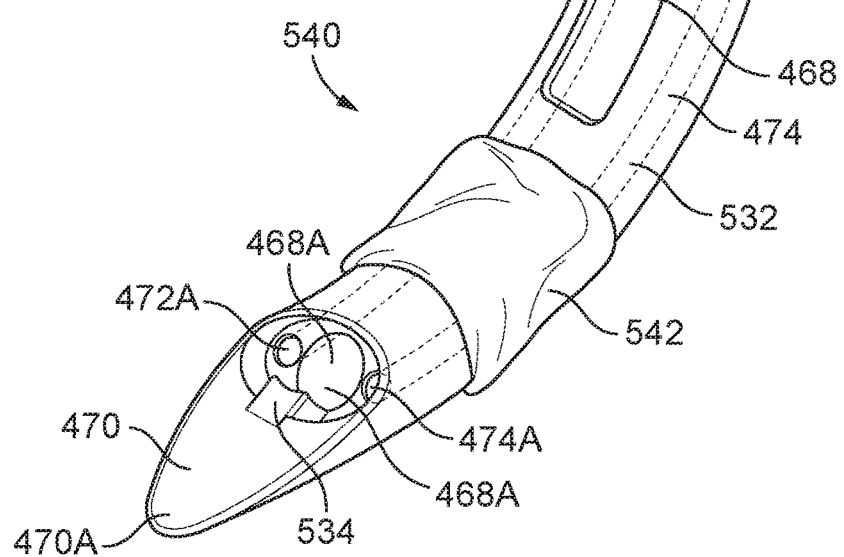
FIG. 4B depicts the oral airway device of FIG. 4A and comprising an inflatable cuff.

Referring to FIG. 4B, it depicts another embodiment of an oral airway device accordingly to this disclosure, generally 540. All of the elements in the device 540 are the same as were described in connection with the oral airway device 530, except the oral airway device comprises an inflatable cuff 542 which is located at the distal portion of wall 532. The inflatable cuff 542 can be inflated with a means 544.

Referring to FIG. 4C, it depicts a loading of the endotracheal tube 480 into the ETT lumen 468 of the oral airway device 530. The FIG. 4C also depicts inserting a camera 12 into the camera channel 472. All other elements are numbered as in connection with FIG. 4A.

FIG. 4D depicts the endotracheal tube 480 loaded in the ETT lumen 468 of the oral airway device 530 and camera 12 being inserted in the camera channel 472. All other elements are numbered as in connection with FIGS. 4A-4C.

Figure 4E:
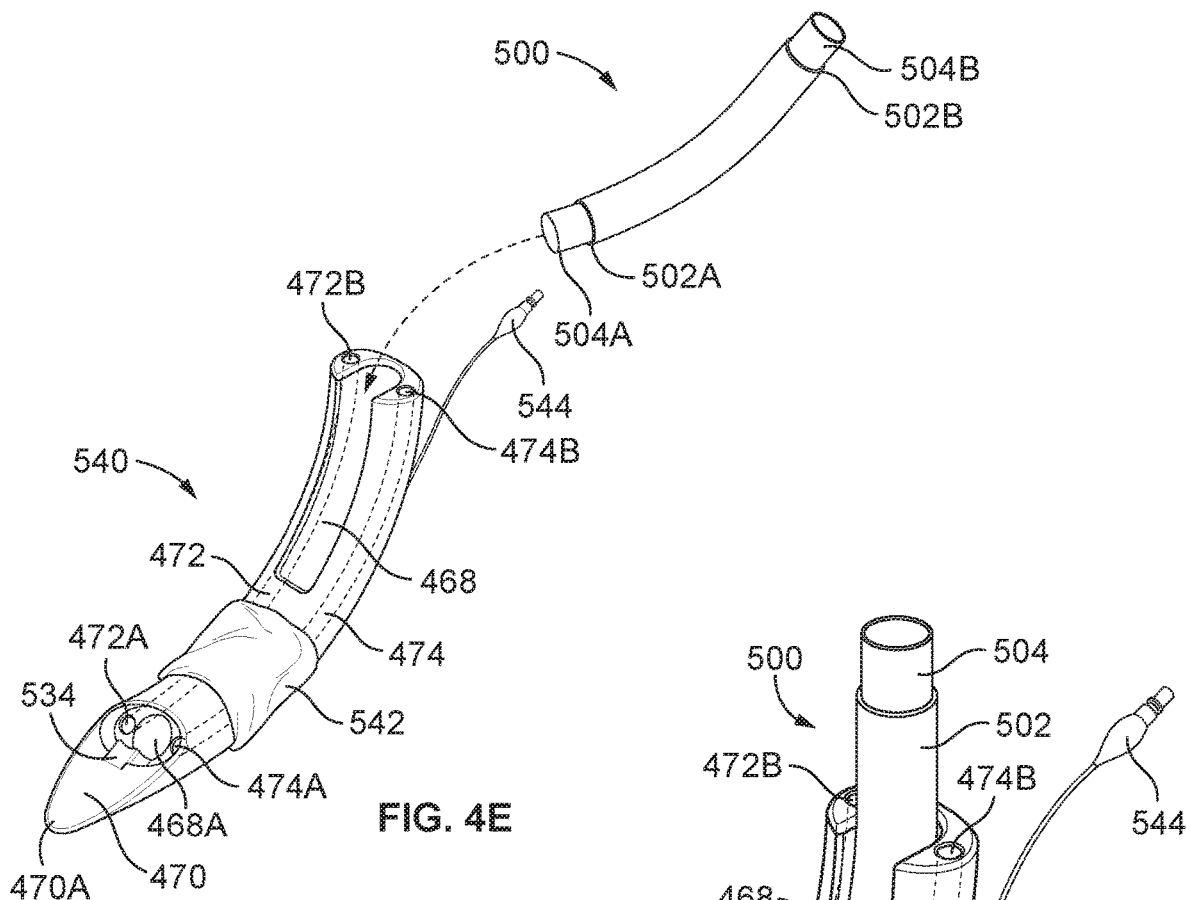
FIG. 4E depicts loading the device of FIG. 1Q into the oral airway device of FIG. 4B.

Referring to FIG. 4E, it depicts an insertion of the device 500 into the ETT lumen 468 of the oral airway device 540 which comprises the inflatable cuff 542. All other elements are numbered as in connection with FIGS. 4A-4D.

Figure 4F:
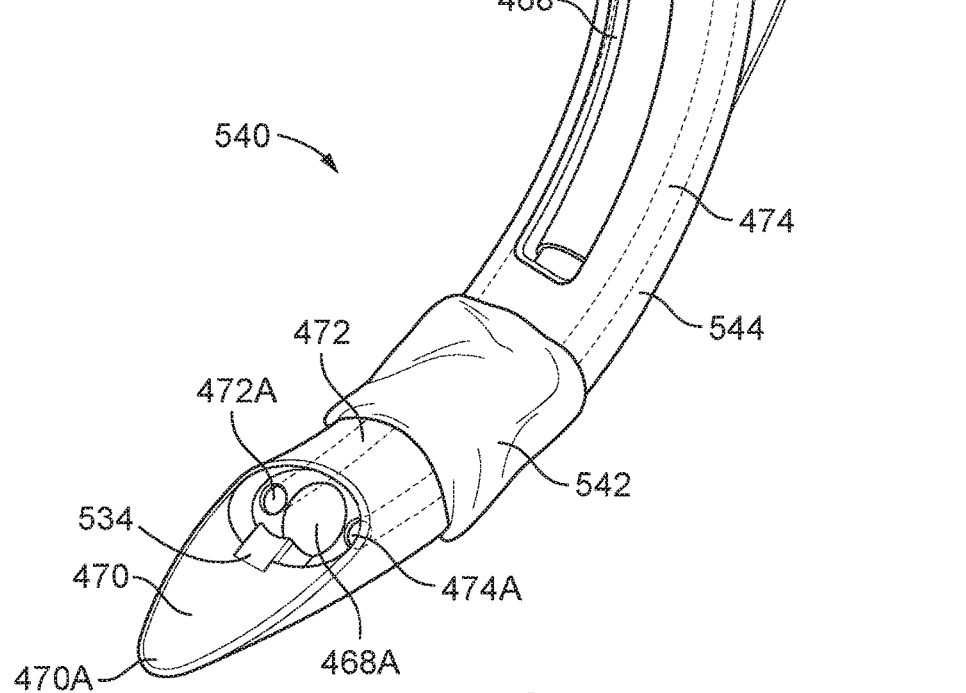
FIG. 4F depicts the device of FIG. 1Q being inserted into the oral airway device of FIG. 4B.

Referring to FIG. 4F, it depicts the device 500 inserted into the ETT lumen 468 of the oral airway device 540 of FIG. 4B. All other elements are numbered as in connection with FIGS. 4A-4E.

Referring to FIG. 4G, it depicts the oral airway device 540 shown from the dorsal surface 532C. All elements are numbered as in connection with FIGS. 4A-4F. A plug 546 is inserted into the proximal opening 472B of the camera channel 472. The plug 546 caps the camera channel 472 and can be used when a closed system needs to be established for ventilation. In the drawing of FIG. 4G, the plug 546 is used in the camera channel 472. In other embodiments, the esophageal channel 474 may be also capped with the plug 546.

Referring to FIGS. 4H and 4I, the plug 456 comprises a hollow cylindrical body 548 and a cap 550 which is attached to the hollow cylindrical body 548 with a bendable string 552. As is shown in FIG. 4H, the cap 550 may cap over the proximal end 548B of the hollow cylindrical body 548. As is shown in FIG. 4I, the cap 550 may be removed from the hollow cylindrical body 548. This allows for air to pass through the hollow cylindrical body 548. The hollow cylindrical body 548 is designed for a tight fit into a channel such as for example, the channel 472 and/or channel 474. Accordingly, the hollow cylindrical body 546 may have a shape of a bottle cork. A diameter of a distal end 548A may be smaller than a diameter of the proximal end 548B. The hollow cylindrical body 548 may comprise ridges 554s.

Figure 4J:
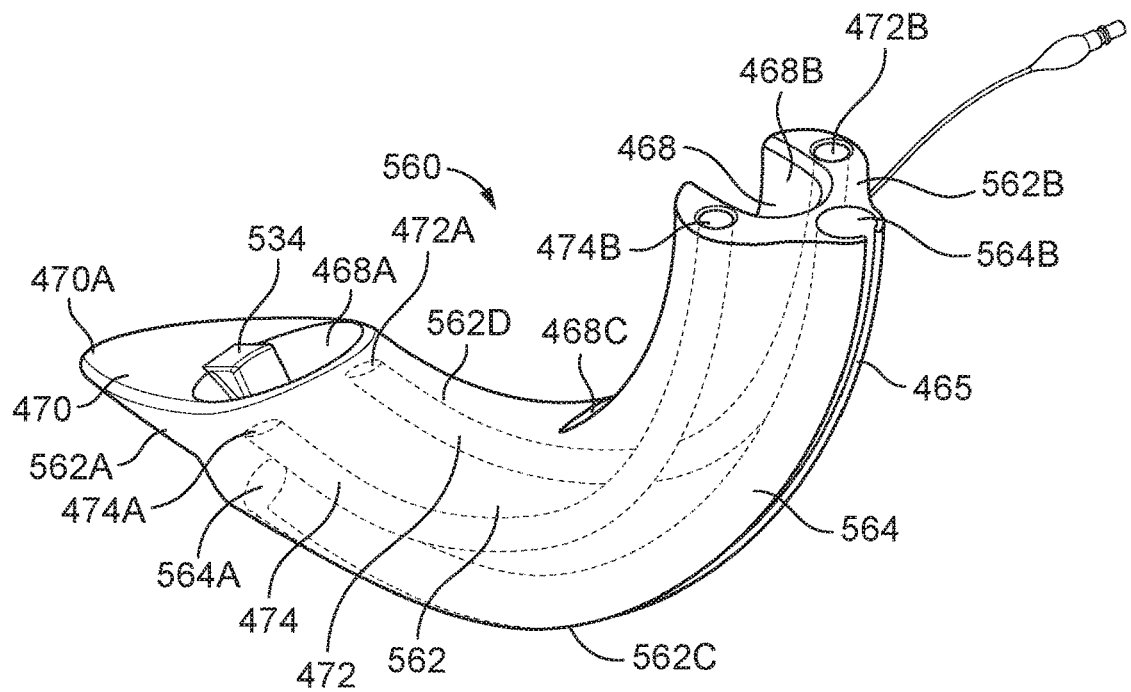
FIG. 4J depicts an oral airway device with a third peripheral channel.

Referring to FIG. 4J, it provides another embodiment of an oral airway device according to this disclosure, generally 560. Just like the oral airway device 530 shown in FIG. 4A, the oral airway device 560 is a tubal body which is curved such that the oral airway device 560 follows the contour of the roof of a patient's mouth during insertion of the device 560 into the patient.

The curved tubal body of the airway device 560 is made by a wall 562 with a distal end 562A and a proximal end 562B. The wall 562 is curved along the distal-proximal 562A-562B axis such that the wall 562 follows the contour of the roof of a patient's mouth. The wall 562 creates an arch. The wall 562 has a dorsal surface 562C and a ventral surface 562D. As will be appreciated by a person of skill because of the arch curvature, a length of the wall 562 is longer on the dorsal surface, 562C, than on the ventral surface, 562D. The ventral surface 562D is in contact with the patient's tongue when the device 560 is placed in the patient.

The wall 562 encircles an ETT lumen 468. The ETT lumen 468 is hollow and has a distal opening 468A. The ETT lumen 468 has a proximal opening 468B at the proximal end of the wall 562. Thus, the ETT lumen 468 runs along the distal-proximal axis 562A-562B.

The wall 562 recesses into the ETT lumen 468 on the ventral surface 562D such that some proximal portion 468C of the ETT lumen 468 is open and is not covered by the wall 562 on the ventral surface 562D. Accordingly, some proximal portion 468C of the ETT lumen 468 is not covered by the wall 562. Keeping the portion 468C of the ETT lumen 468 not enclosed with the wall 564 on the ventral surface 462D helps with loading into and removing from the central lumen 468 a medical device, such as an endotracheal tube.

At the distal end 562A, the wall 562 ends with a tongue 470 on the dorsal surface 562C. The distal end 470A of the tongue 470 may be of an oval or round shape. The tongue 470 is tapered at its distal end 470A. The tongue 470 is used to gently push patient's tissues apart during insertion of the device 560. The tongue 470 protrudes distally from the wall 562.

There is a ramp 534 positioned proximally to the tongue 470 and distally to the distal opening 468A. The ramp 534 elevates and supports a distal end of a device, such as for example an endotracheal tube, inserted into the ETT lumen 468.

The wall 562 has at least two hollow peripheral channels, 472 and 474. The camera channel 472 is hollow and is positioned peripherally to the ETT lumen 468. The camera channel 472 has a proximal opening 472B at the proximal end 562B of the wall 562. The camera channel 472 runs along the distal-proximal 562A-562B axis of the wall 562. The camera channel 472 ends with a distal opening 472A at the distal end 562A of the wall 562.

A camera (not shown) can be inserted through the proximal opening 472B in the camera channel 472. The camera can protrude from the distal opening 472A of the camera channel 472. Any camera described in this disclosure or generally known in the art can be used in the oral airway device 560. The camera is insertable and removable from the channel 472. A position of the camera at the distal opening 472A of the channel 472 can be adjusted as needed in order to monitor patient's tissues and/or insertion of the device 530.

In some embodiments, the camera channel 472 is a passage in the wall 562 and the camera channel 472 is completely separated from the ETT lumen 468. In other embodiments, the camera channel 472 is a semi-lumen which is connected to the ETT lumen 468. In further embodiments, there is a slit (not shown in the drawing) that runs along the length of the camera channel 472. The slit of the camera channel 472 may run along the wall 562 externally.

The structure of the second channel, 474, is similar to the structure of the first channel 472. The channel 472 is a peripheral hollow channel. The channel 474 runs along the distal-proximal 462A-462B axis of the wall 462. The channel 474 is located peripherally to the ETT lumen 468. As can be seen in FIG. 4J, the channels 472 and 474 flank the ETT lumen 468 which is positioned between the channels 472 and 474.

The channels 472 and 474 may be of the same diameter or they may be of a different diameter.

The channel 474 ends with a distal opening 474A at the distal end 562A of the wall 562.

The tools are insertable and removable from the channel 474. A position of the tool at the distal opening 474A can be adjusted as needed in order to manipulate patient's tissues or to provide suction. In some embodiments, the channel 474 is a passage in the wall 564 and the channel 474 is completely separated from the ETT lumen 468. In other embodiments, the channel 474 is a semi-lumen which is connected to the ETT lumen 468. In further embodiments, there is a slit that runs along the length of the channel 474. The slit opens into the ETT lumen 468.

A relative positioning of the channels 472 and 474 is such that when a camera is inserted in the channel 472 and protrudes from the distal opening 472A of the channel 472, the camera can visualize a distal end of a tool inserted into the channel 474 and protruding from the distal opening 474A of the channel 474. Accordingly, manipulations of the tool are visualized with the camera.

As can be appreciated by a person of skill, in some embodiments, the channels 472 and 474 may be interchangeable, i.e. a camera can be inserted into either of the two channels, as needed. In some embodiments, two cameras can be used at the same time.

As can be seen in FIG. 4J, the oral airway device 560 comprises a third channel, 564, which runs along the dorsal-ventral axis 562A-562B on the dorsal surface 562C. In the embodiment of FIG. 4J, the channel 564 is a semi-lumen which opens to the dorsal surface 562C. The channel 564 also has a proximal opening 564B. The channel 564 can be used for loading a stomach suction tube or a scope for the EGD procedure which can be placed in a patient in one step and together with an endotracheal tube when both devices are loaded into the oral airway device 560.

The stomach suction tube or scope can be then easily removed from the channel 564 while the oral airway device 560 still remains inserted into a patient. Because the channel 564 has a groove-like shape it holds the stomach suction tube or scope in place and prevents it from sliding and slipping. The length of the channel 564 may vary. In some embodiments the channel 564 runs along all or most all of the dorsal surface 562C of the wall 562. In these embodiments, the channel 564 ends at or near the distal end 562A of the wall 562. In other embodiments, the channel 564 runs only along a portion of the wall 562 and it ends at any place proximally to the distal end 562A of the wall 562.

Figure 4K:
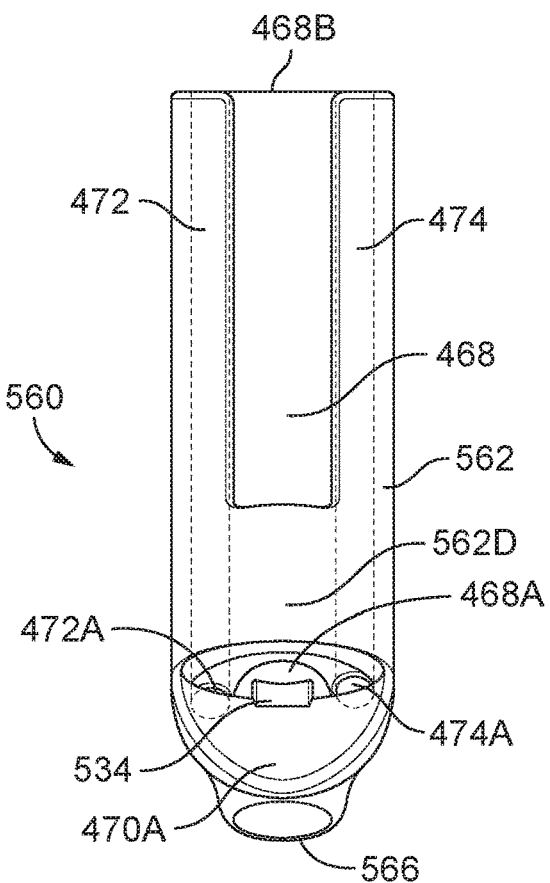
FIG. 4K depicts a ventral surface of the oral airway device of FIG. 4J.

Referring to FIG. 4K, it is a ventral view of the oral airway device 560 from the ventral surface 562D. All elements are numbered as in connection with FIG. 4J

The distal opening 472A to the camera channel 472 is shown. The distal opening 474A to the esophageal channel 474 is also shown. The proximal portion 468C of the ETT lumen 468 is not covered by the wall 562 on the ventral surface 562D. The ramp 534 is shown. The distal portion 470A of the tongue 470 is also shown.

As shown in the drawing of FIG. 4K, the oral airway device 560 may comprise a loop 566 attached externally near the distal end 562A of the wall 562. One of the functions for the loop 566 is to hold in place a stomach suction tube or scope loaded into the channel 564. The stomach suction tube or any other tube or tool may be pulled through the loop 566. Accordingly, the loop 566 secures the positioning of the stomach suction tube or any other tube or tool on the oral airway device 560 and prevents the stomach suction tube or any other tube or tool from separating from the oral airway device 560. A person of skill will appreciate that the loop 566 may be attached to the oral airway device 560 or any other of the oral airway devices provided in this disclosure, including the oral airway device 460, 510, 520, 530 or 540.

In another aspect, the present disclosure provides oral airway devices which comprise channels, but do not comprise the endotracheal tube (ETT) lumen 468. These oral airway devices will be now described with reference to FIGS. 5A-5F, FIG. 6 and FIGS. 10A-10 D.

Figures 5A, 5B, 5C:
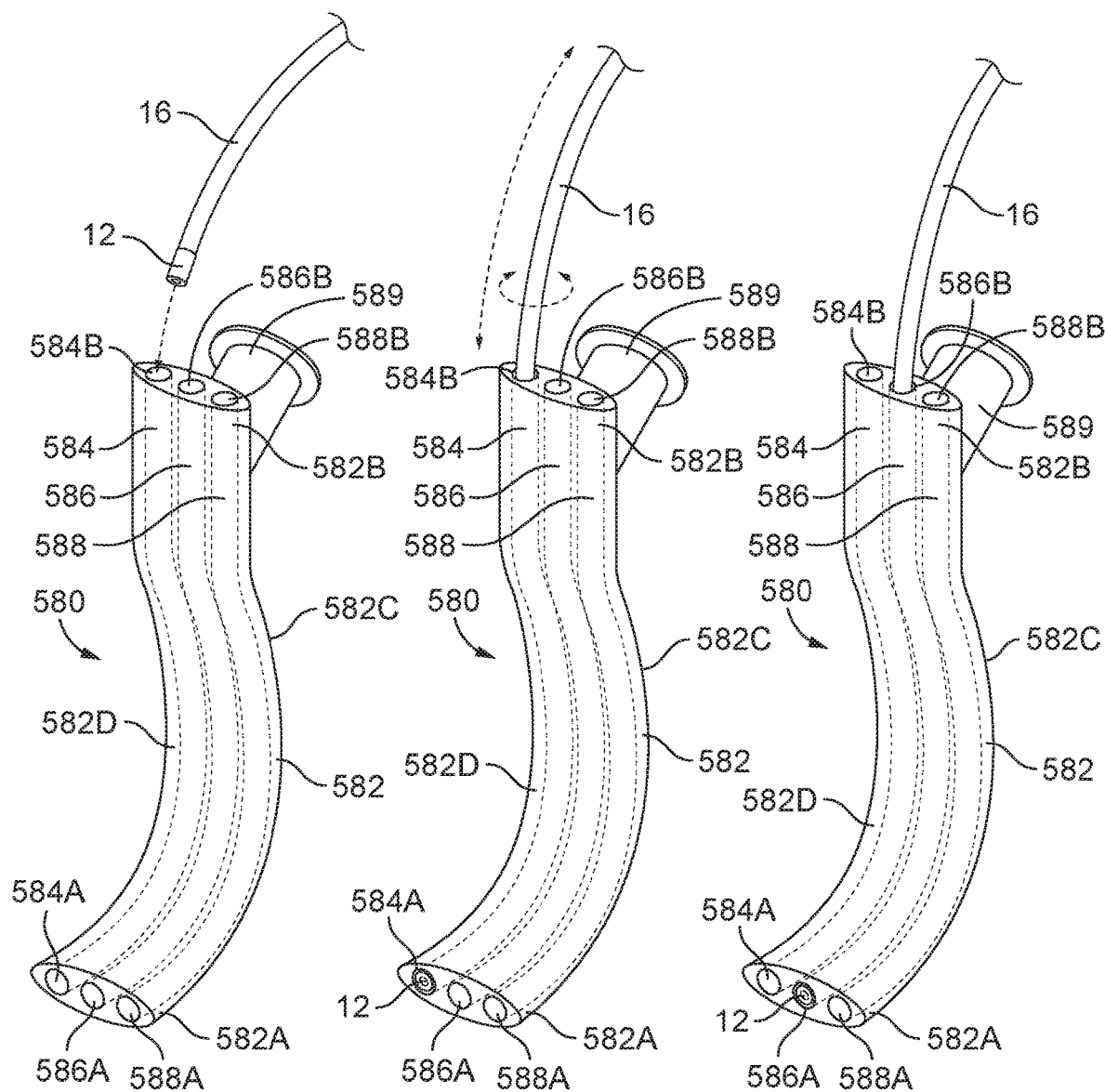
FIG. 5A depicts another embodiment of an oral airway device according to this disclosure.
FIG. 5B depicts a camera being inserted into one of the channels of the oral airway of FIG. 5A.
FIG. 5C depicts a camera being inserted into another channel of the oral airway of FIG. 5A.

Referring to FIG. 5A, it provides another embodiment of an oral airway device, generally 580. The oral airway device 580 comprises a tubal body created by a wall 582 with a distal end 582A and a proximal end 582B. The oral airway device 580 may comprise a handle 589 located near the proximal end 582B which may aid a practitioner in manipulating the oral airway device 580 during insertion or removal. The handle 589 may be adhered to the wall 582 or the handle 589 may be attached to the wall 582 removably such that the handle 589 is removed after the insertion of the oral airway device 580 has been completed.

The wall 582 is curved along the distal-proximal axis 582A-582B and follows the contour of the roof of a patient's mouth during insertion of the oral airway device 580 into the patient. The wall 582 has a dorsal surface, 582C, and a ventral surface, 582D. The wall 582 creates an arch which follows the contour of the roof of a patient's mouth such that the ventral surface 582D is in contact with the patient's tongue when the device 580 is inserted in the patient.

The oral airway device 580 has several hollow channels, 584, 586 and 588 which run through the tubal body 582. In other embodiments, the oral airway device 580 may have more or fewer than 3 channels.

Each of the channels, 584, 586 and 588, opens with a proximal opening 584B, 586B, and 588B, respectively, at or near the proximal end 582B of the wall 582. Each of the channels, 584, 586 and 588, opens with a distal opening 584A, 586A, and 588A, respectively, at or near the distal end 582A of the wall 582. In some other embodiments, a cuff (not shown), either inflatable or non-inflatable, is attached around the perimeter of the wall 582 in the near proximity to the distal end 582A of the wall 582.

In the embodiment of FIG. 5A, the oral airway device 580 comprises three channels. In other embodiments, the oral airway device 580 may comprise more than three, i.e. 4 or 5, or fewer than 3 channels, i.e. 2 or 1. The channels 584, 586 and 588 are passages in the tubal body 582. The channels 584, 586 and 588 can be used for hosting various devices. As shown in FIG. 5A, a camera 12 can be inserted into one of the channels, 584, 586 and/or 588.

FIG. 5B depicts the camera 12 being inserted into the channel 584 of the oral airway device 580. All elements are numbered as in connection with FIG. 5A.

FIG. 5C depicts the camera 12 being inserted into the channel 586. Accordingly, the oral airway device 580 is compatible with a camera and more than one camera can be used. At least one of the distal openings 584A, 586A and/or 588A is not sealed. This allows for a tool or the camera 12 to protrude distally from the oral airway device 580. The camera 12 is attached to a cable 16. The cable 16 can be used to move the camera 12 further distally or to remove the camera 12 from the oral airway device 580 while the oral airway device 580 remains inserted in a patient. The oral airway device 580 may be used for hosting a number of various tools, for example a bougie and a suction tube, which can be manipulated under continuation visualization by a camera.

In addition to embodiments in which a camera is insertable to one or more channels, a camera can be built-in the wall 582 in other embodiments. The oral airway device 580 can be used in combination with several cameras which would provide visualization of the patient's tissues from different positions.

Figure 5D:
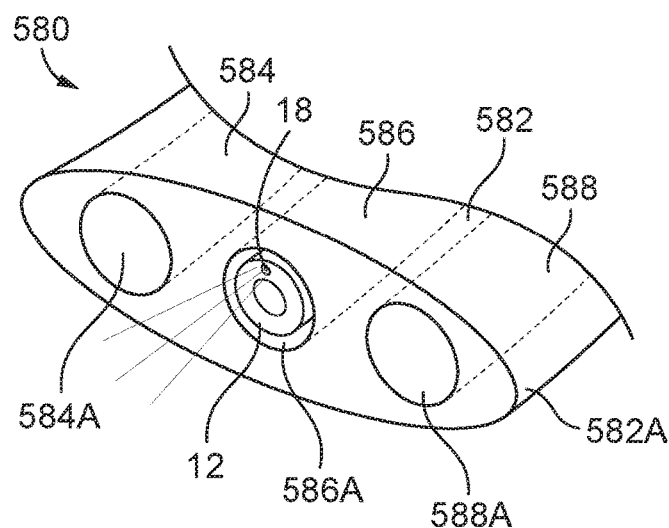
FIG. 5D depicts the distal end of the oral airway device of FIG. 5A with a camera being inserted into one of the channels.
Figure 5F:
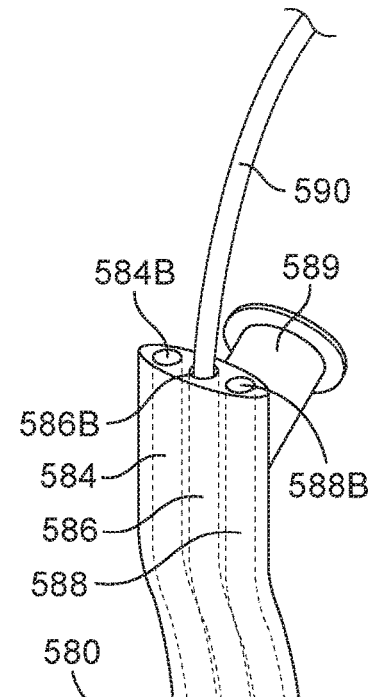
FIG. 5F depicts a bougie being inserted into one of the channels of the oral airway device of FIG. 5A.
Figure 5E:
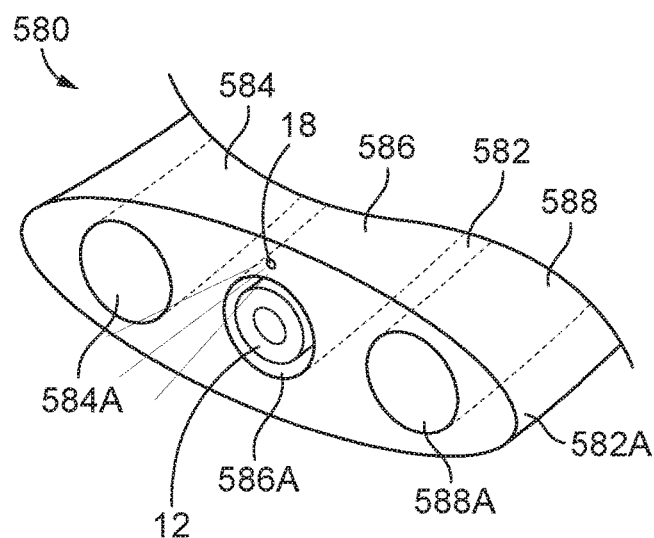
FIG. 5E depicts the distal end of the oral airway device of FIG. 5A which comprises a light source, with a camera being inserted into one of the channels.

FIGS. 5D and 5E are zoom-in views of the distal end 582A of the oral airway device 580. The distal opening 584A of the channel 584 and the distal opening 588A of the channel 588 are shown. The camera 12 is inserted in the channel 586 and can be seen at the distal opening 586A of the channel 586. In the embodiment of FIG. 5D, the camera 12 comprises a light source 18. In the embodiment of FIG. 5E, the light source 18 is incorporated into the wall 582.

FIG. 5F depicts a bougie 590 inserted into the channel 586 of the oral airway device 580. A distal end 590A of the bougie 590 protrudes distally from the distal end 586A of the channel 586. The bougie 590 or any other tool inserted into one of the channels 584, 586 and/or 588 can be manipulated under a continuous visualization from the camera 12 as shown in FIGS. 5A-5E.

Figure 6:
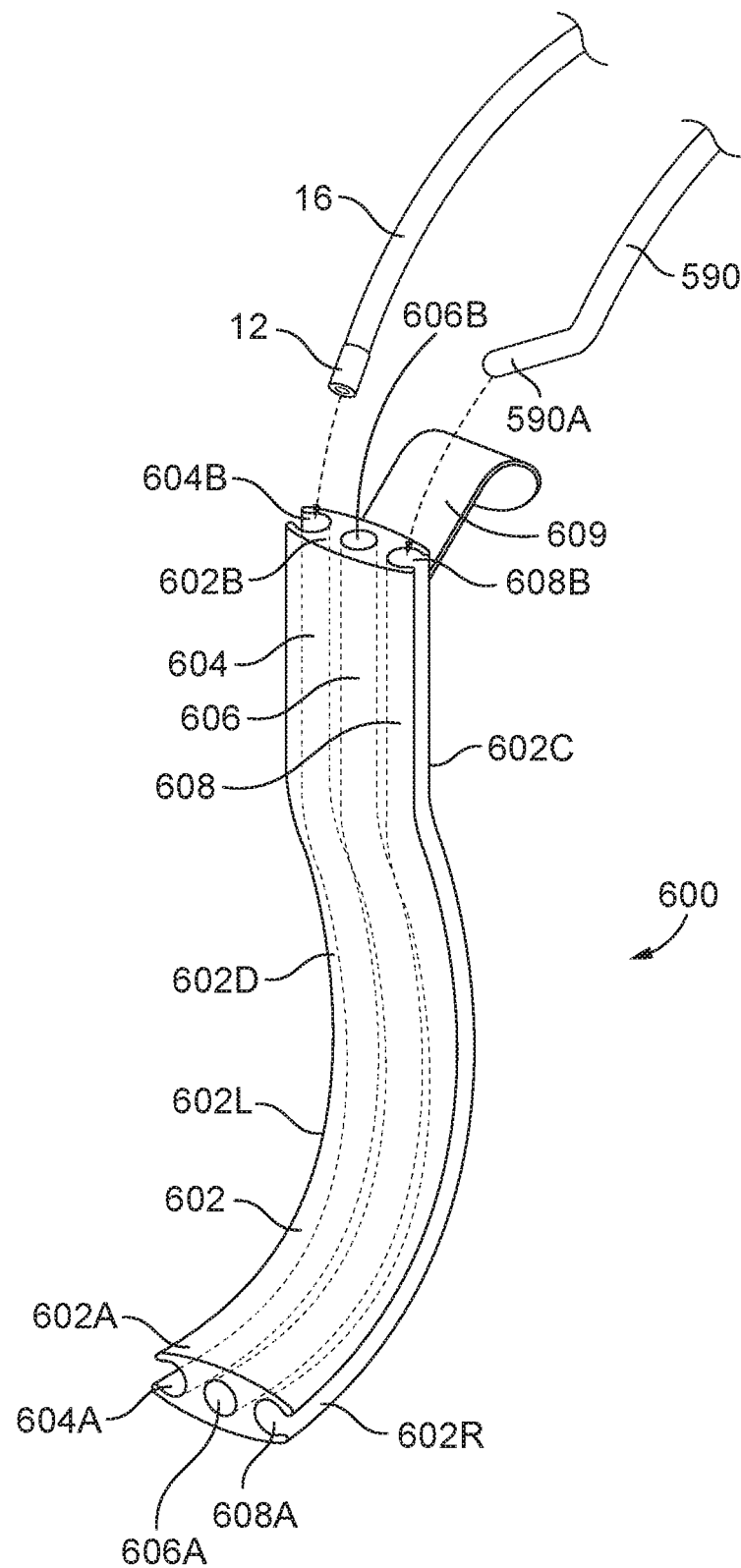
FIG. 6 depicts an oral airway device with peripheral channels opening externally along the oral airway device body.

FIG. 6 depicts another embodiment of an oral airway device with channels, generally 600. The oral airway device 600 comprises a tubal body created by a wall 602 with a distal end 602A and a proximal end 602B. The wall 602 is curved along the distal-proximal axis 602A-602B and follows the contour of the roof of a patient's mouth during insertion of the device 600 into the patient. The wall 602 has a dorsal surface, 602C, and a ventral surface, 602D. In some embodiments, the oral airway device 600 may comprise a handle 609 attached to the wall 602 on the dorsal surface 602C in proximity to the proximal end 602B. The handle 609 aids a practitioner in manipulating the device 600 during insertion and removal. The handle 609 may be attached removably such that the handle 609 can be separated from the wall 602 after the oral airway device 600 has been placed.

The wall 602 creates an arch which follows the contour of the rood of a patient's mouth such that the ventral surface 602D is in contact with a patient's tongue when the device 580 is inserted in the patient. The oral airway device 600 has several channels, 604, 606 and 608 which run through the wall 602 along the distal-proximal 602A-602B axis.

Each of the channels, 604, 606 and 608, opens with a proximal opening 604B, 606B, and 608B, respectively, at the proximal end 602B of the wall 602. Each of the channels, 604, 606 and 608, opens with a distal opening 604A, 606A, and 608A, respectively, at the distal end 602A of the wall 602. In the embodiment of FIG. 6, the oral airway device 600 comprises three channels. In other embodiments, this oral airway device 600 may comprise more than three, for example, 4 or 5, or fewer than 3 channels, for example, 2 or 1.

The channel 608 is a peripheral channel. It is a semi-lumen which opens externally on the wall 602. Accordingly, the channel 608 can be described as a recess in the wall 602 which runs along the distal-proximal axis 602A-602B. The channel 608 creates a groove into which a camera, tool or a tube can be placed. Because of its groove-like shape, the channel 608 keeps the camera, tool or tube in place and prevents it from jamming. However, as the channel 608 is open along the distal-proximal axis 602A-602B, it is easy to remove the camera, tool or tube from the channel 608 while the oral airway device 600 still remains inserted and in place in a patient. In the drawing of FIG. 6, the channel 608 opens externally to the right flank 602R of the wall 602. In other embodiments, the channel 604 may open to the dorsal surface 602C or ventral surface 602D of the wall 602.

The channel 606 is a hollow passage in the wall 602. The channel 604 has the same structure as the channel 608 in the embodiment of FIG. 6.

The channel 604 is located peripherally to the channel 606. The channel 604 is a semi-lumen which opens externally from the wall 602. In the drawing of FIG. 6, the channel 604 opens eternally to the left flank 602L of the wall 602. In other embodiments, the channel 604 may open to the dorsal surface 602C or ventral surface 602D of the wall 602.

Accordingly, the channel 604 can be viewed as a recess in the wall 602 which runs along the distal-proximal axis 602A-602B. The channel 604 creates a groove into which a camera, tool or a tube can be placed. Because of its groove-like shape, the channel 604 keeps the camera, tool or tube in place and prevents it from jamming. However, as the channel 604 is open along the distal-proximal axis 602A-602B, it is easy to remove the camera, tool or tube from the channel 608 while the oral airway device 600 still remains inserted and in place in a patient.

As is shown in FIG. 6, the camera 12 attached to the cable 16 can be placed in the channel 604 while a bougie 590 can be placed in the channel 608. Because the channel 608 is a groove, the bougie 590 with the distal end 590A being bended can still be placed in the channel 608. The distal end 590A of the bougie 590 is placed distally to the distal opening 608A of the channel 608. The rest of the bougie 590 is then placed inside of the channel 608.

It will be appreciated that while in the embodiment of FIG. 6, both peripheral channels 604 and 608 are semi-lumens which are open externally along the distal-proximal 602A-602B axis of the wall 602, in other embodiments the oral airway device 600 may comprise only one peripheral channel and/or only one of the two peripheral channels may be opening externally along the distal-proximal 602A-602B axis of the wall 602. In the embodiment of FIG. 6, the opening is a gap-like. In further embodiments, the opening may be a slit.

As it was already described in connection with drawings of FIGS. 5A-5F, any of the three channels, 604, 606 and/or 608, may be used for inserting a camera or a tool including for example, forceps, a suction tube, a stethoscope, a temperature probe, a bougie or a stylet.

In some embodiments, the oral airway device 600 may comprise an inflatable or non-inflatable cuff (not shown) attached around the perimeter of the wall 602 in the near proximity to the distal end 602A. In the embodiments where peripheral channels open with grooves to the wall 602, the cuff may also have slits that align with the grooves such that the cuff does not run over the grooves.

Further embodiments of this disclosure provide an adaptor which converts a medical tool or tube, such as for example an endotracheal tube, into a medical tool or tube which is compatible with a camera.

Figure 7A:
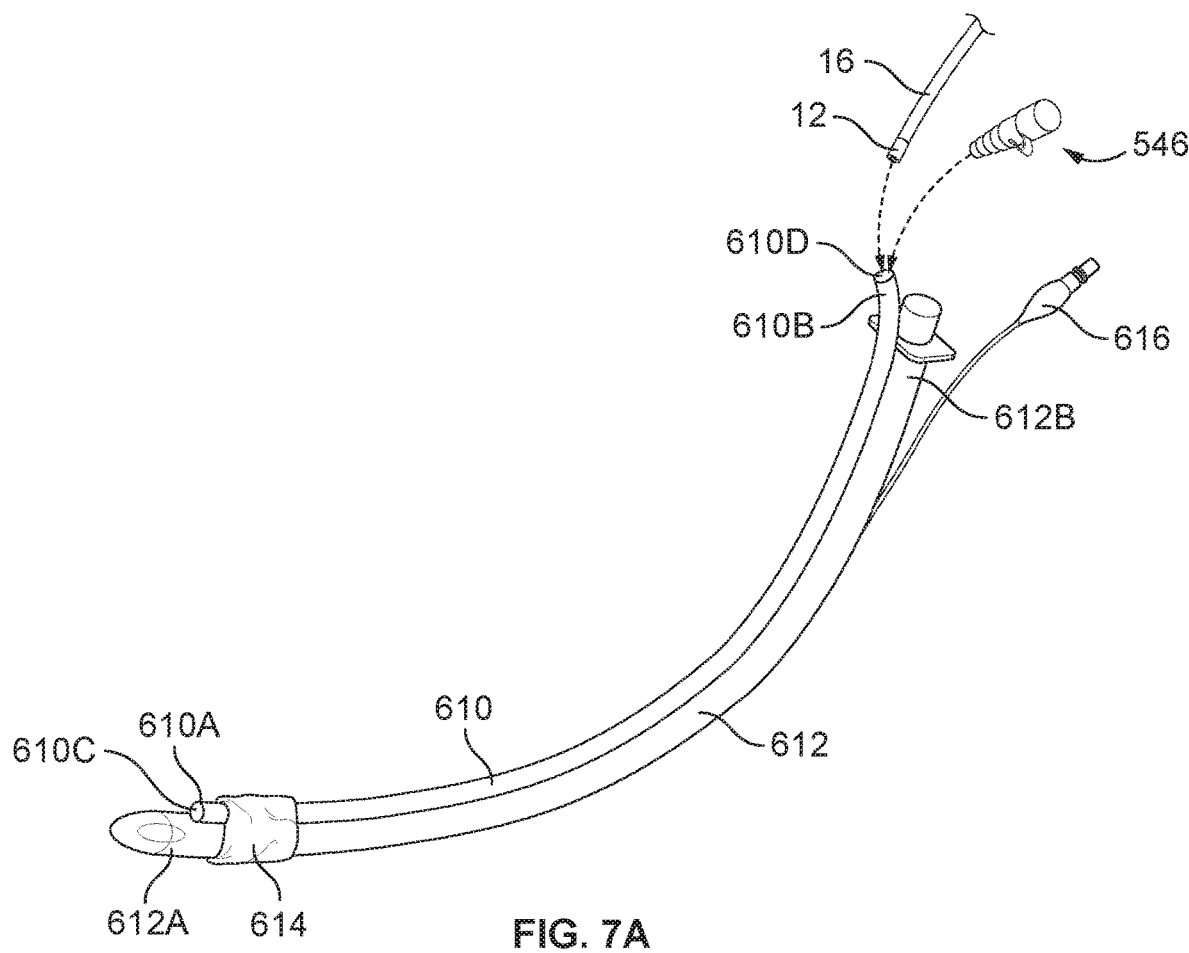
FIG. 7A depicts one embodiment of an adaptor being combined with an endotracheal tube.

One embodiment of the adaptor is shown in FIG. 7A. In this embodiment, the adaptor 610 is a plastic tube with a distal end 610A and a proximal end 610B which is combined with an endotracheal tube 612. The adaptor 610 may have a slit which runs along the tube from the proximal end 610B to the distal end 610A.

The endotracheal tube has a distal end 612A and a proximal end 612B. There is an inflatable cuff 614 which wraps around the endotracheal tube 612 in a proximity to the distal end 612A. The distal end 610A of the adaptor 610 is located distally to the cuff 614. The adaptor 610 runs along the distal-proximal axis 612A-612B. The adaptor 610 may be attached, such as for example by being adhered to the endotracheal tube 612 along the distal-proximal axis 612A-612B. In alternative, the adaptor 610 may be placed under the cuff 614 such that the adaptor 610 may glide along the endotracheal tube 612.

The proximal end 610B of the adaptor 610 protrudes proximally from the proximal end 612B of the endotracheal tube 612. The cuff 614 can be inflated with a means 616 once the endotracheal tube 612 is placed in a patient.

The adaptor 610 is a hollow tube which may or may not have a slit and which has an opening 610C at the distal end 610A and an opening 610D at the proximal end 610B.

A camera 12 with cable 16 can be placed inside the adaptor 610 through the proximal opening 610D. When not in use, the camera 12 can be removed from the adaptor 610. The proximal opening 610D can be plugged with the plug 546 if a closed system needs to be established for ventilating a patient. The distal end 610C of the adaptor 610 is not sealed. Accordingly, the camera 12 can protrude distally from the adaptor 610. In the embodiment of FIG. 7A, the adaptor 610 is placed under the cuff 614 which may be used for holding the adaptor 610 together with the endotracheal tube 612. At least in some embodiments, the adaptor 610 can slide distally and proximally along the endotracheal tube 612.

Figure 7B:
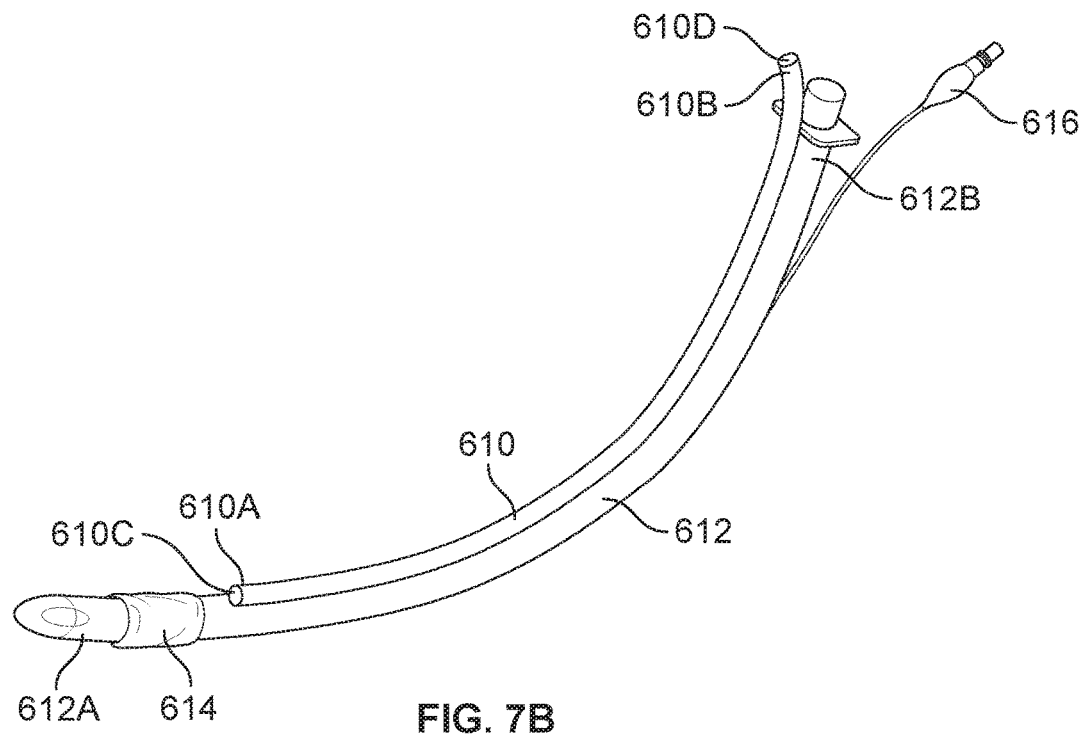
FIG. 7B depicts another embodiment of an adaptor being combined with an endotracheal tube.

Referring to FIG. 7B, the distal end 610A of the adaptor 610 is positioned proximally to the cuff 614. All other elements are numbered as was discussed in connection with FIG. 7A. In the embodiment of FIG. 7B, the adaptor 610 may be attached to the endotracheal tube 612 such that the adaptor 610 can still slide along the distal-proximal axis 612A-612B. In alternative, the adaptor 610 may be adhered to the endotracheal tube 612 and it does not slide.

Figure 8A:
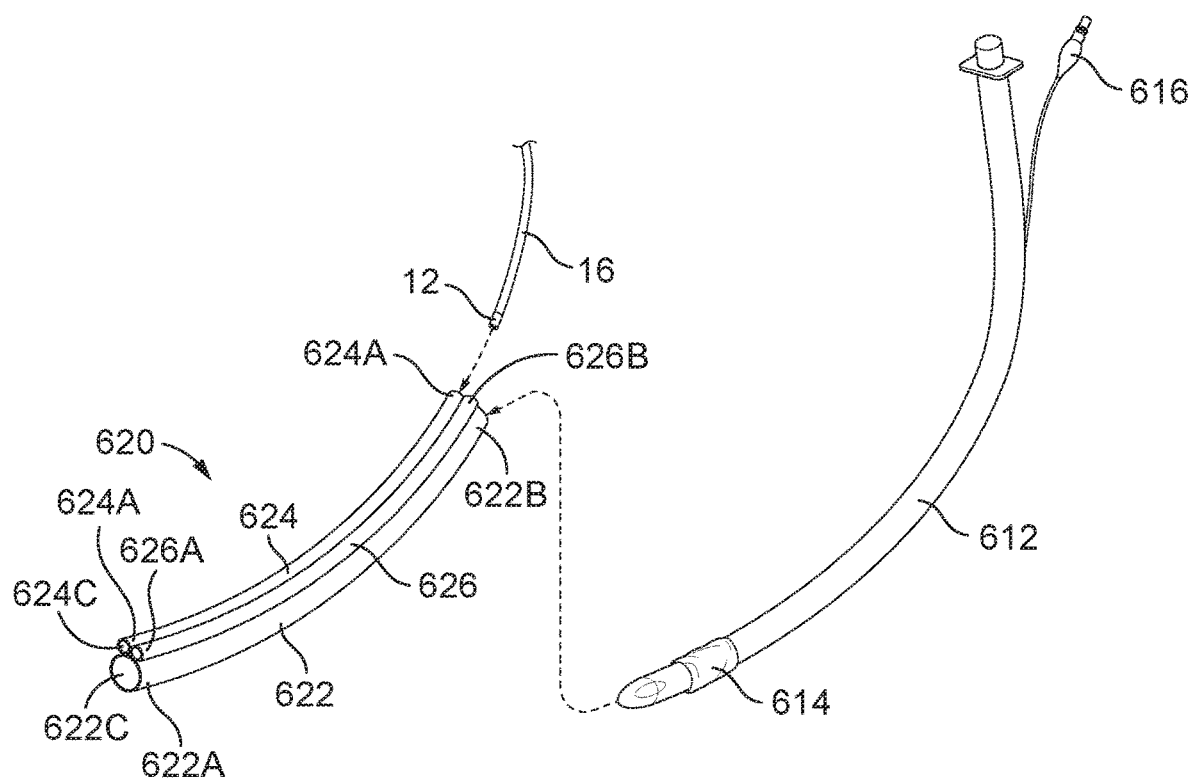
FIG. 8A is a further embodiment of an adaptor according to this disclosure.

Referring to FIG. 8A, it provides a further embodiment of an adaptor according to this disclosure, generally 620. The adaptor 620 comprises a hollow tube 622 with a distal end 622A and a proximal end 622B. The hollow tube 622 may have a slit (not shown) which runs the distal/proximal axis 622A/622B.

The hollow tube 622 has an opening 622C at the distal end 622A and an opening 622D (not shown in the drawing of FIG. 8A) at the proximal end 622B. The diameter of the hollow tube 622 is compatible with a diameter of an endotracheal tube 612. Accordingly, the endotracheal tube 612 can be inserted into the hollow tube 622. If a slit is present, it helps with insertion and removal of the endotracheal tube 612 from the hollow tube 622.

At least one second hollow tube 624 is attached to the hollow tube 622. The second hollow tube 624 has a distal end 624A and a proximal end 624B. The second hollow tube 624 has an opening 624C at the distal end 624A. The second hollow tube 624 has an opening 624D at the proximal end 624B. The distal end 624A of the second hollow tube 624 is aligned with the distal end 622A of the hollow tube 622. The proximal end 624B of the second hollow tube 624 is aligned with the proximal end 622B of the hollow tube 622.

A diameter of the second hollow tube 624 is compatible with a camera 12 such that the camera 12 connected to the cable 16 can be inserted through the proximal opening 624D into the second hollow tube 624. Since the distal end 624C is not sealed, the camera 12 can protrude distally from the second hollow tube 624. At least in some embodiments, the distal end 624A of the tube 624 may be sealed with a transparent window which prevents the camera 12 from coming in contact with bodily fluids.

The adaptor 620 may comprise one or more additional hollow tubes. In FIG. 8A, a third hollow tube 626 is shown. In other embodiments, the third hollow tube may be absent or the adaptor 620 may comprise a plurality of hollow tubes 626. The hollow tube 626 is attached to the hollow tube 620. The hollow tube 626 has a distal end 626A and a proximal end 626B. The hollow tube 626 has an opening 626C at the distal end 626A. The hollow tube 626 has an opening 626D at the proximal end 626B.

The distal end 626A of the hollow tube 626 is aligned with the distal end 622A of the hollow tube 622. The proximal end 626B of the hollow tube 626 is aligned with the proximal end 622B of the hollow tube 622. A diameter of the hollow tube 626 is compatible with a camera 12 such that the camera 12 connected to the cable 16 can be inserted through the proximal opening 626D into the hollow tube 626. Since the distal end 626C is not sealed, the camera 12 can protrude distally from the hollow tube 626. The hollow tubes 624 and 626 can be used interchangeable for hosting a camera and a tool, such as for example a bougie and/or stylet. A camera can be inserted into one of the hollow tubes 624 or 626, while a tool can be inserted into the other. An endotracheal tube is loaded into the hollow tube 622.

Figure 8B:
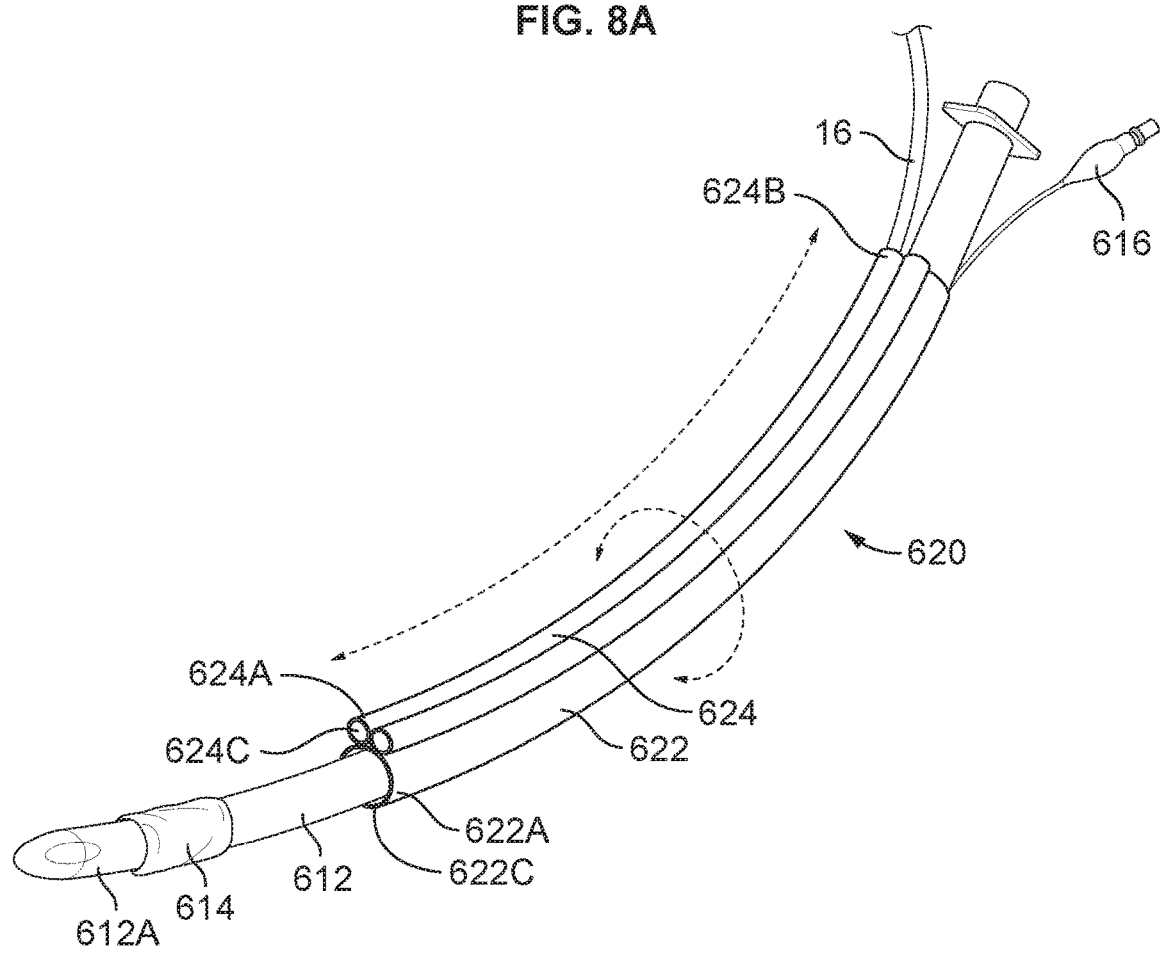
FIG. 8B depicts the adaptor of FIG. 8A being combined with an endotracheal tube and camera.

Referring to FIG. 8B, it depicts the endotracheal tube 612 and the camera 12 loaded into the adaptor 620. As can be seen from the assembly in FIG. 8B, the camera 12 placed in the tube 624 can provide a continuous visualization during placement of the endotracheal tube 12. If placement of the endotracheal tube 12 needs to be guided with a tool, the tool can be inserted into the third hollow channel, 626.

As shown in FIG. 8B, the adaptor 620 can rotate around the endotracheal tube 12 clock-wise and/or counter-clockwise. This allows to move the camera 12 and/or tools as needed. The adaptor 620 can also slide along the distal-proximal 612A-612B axis of the endotracheal tube 612. This allows additional flexibility in combining the camera and/or tools closer or further away from the distal end 612A of the endotracheal tube 612.

The adaptor 620 can be used with a variety of endotracheal tubes and/or other devices as a diameter of the hollow tube 622 and the diameters of the hollow tubes 624 and 626 can be designed to accommodate various devices.

Figure 8C:
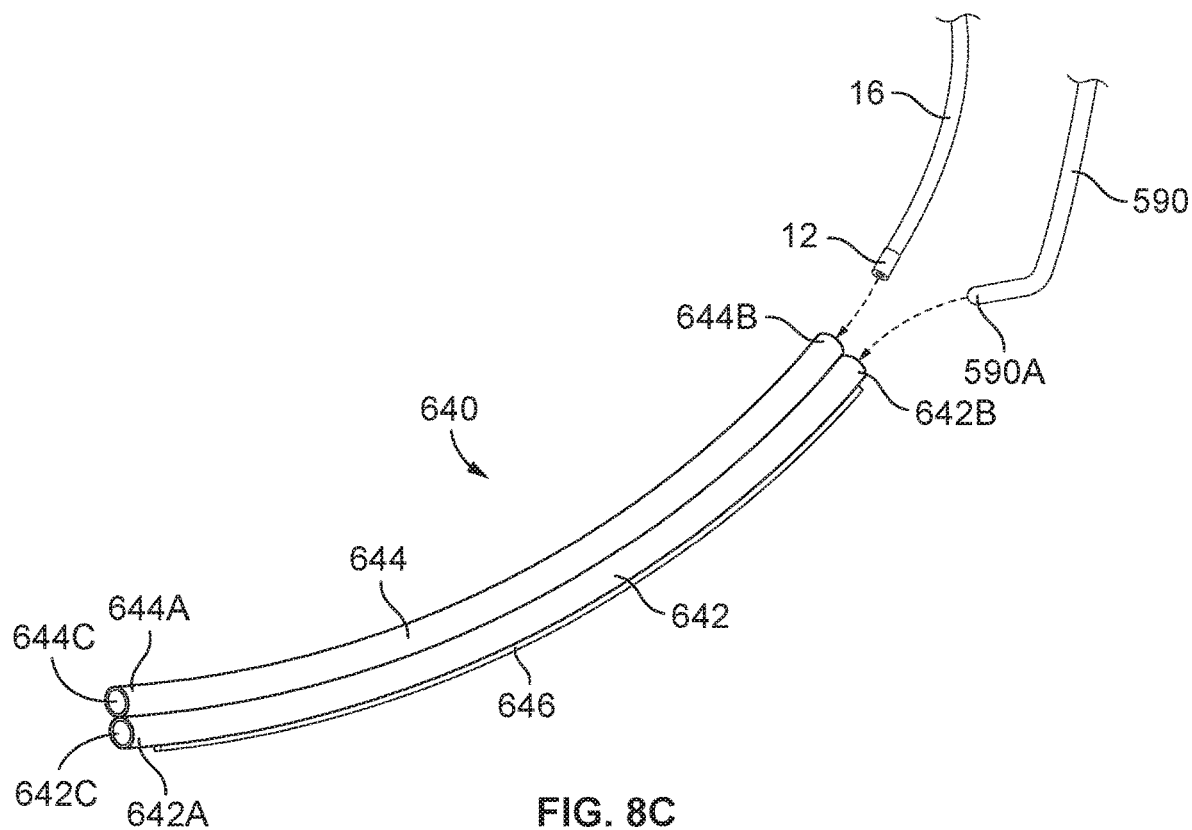
FIG. 8C depicts another embodiment of an adaptor comprising two hollow tubes and a backbone rod.

Referring to FIG. 8C, it depicts a further embodiment of an adaptor according to this disclosure, generally 640. The adaptor 640 comprises a hollow tube 642 with a distal end 642A and a proximal end 642B. The hollow tube 642 has an opening 642C at the distal end 642A and an opening 642D (not shown in the drawing of FIG. 8C) at the proximal end 642B.

At least one second hollow tube 644 is attached to the hollow tube 642. The second hollow tube 644 has a distal end 644A and a proximal end 644B. In other embodiments, the adaptor 640 may comprise a plurality of second hollow tubes 644, for example, 2 or 3 or 4 of the second hollow tubes 644.

The second hollow tube 644 has an opening 644C at the distal end 644A. The second hollow tube 644 has an opening 644D at the proximal end 644B. The distal end 644A of the second hollow tube 644 is aligned with the distal end 642A of the hollow tube 642. The proximal end 644B of the second hollow tube 644 is aligned with the proximal end 642B of the hollow tube 642. A diameter of the second hollow tube 624 is compatible with a camera 12 such that the camera 12 connected to the cable 16 can be inserted through the proximal opening 644D into the second hollow tube 644. Since the distal end 644C is not sealed, the camera 12 can protrude distally from the second hollow tube 644. A bougie 590 or any other tool or tube, i.e. an endotracheal tube, can be placed in the hollow tube 642.

The adaptor 640 may further comprise a stylet or rod 646 which runs along the hollow tube 642 for at least some of the length of the hollow tube 642 and provides a support and backbone to the adaptor 640. In further embodiments, the rod 646 is not present. In other embodiments, the adaptor 640 does not comprise the stylet or rod 646.

Figure 8D:
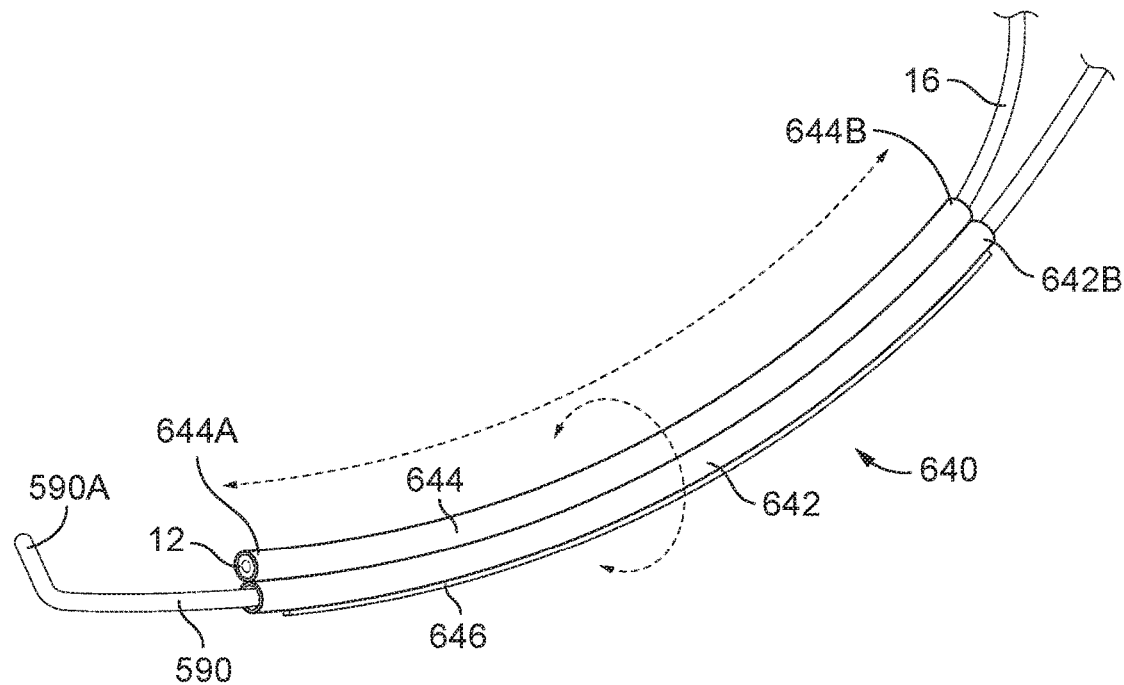
FIG. 8D depicts a bougie and camera being inserted into the adaptor of FIG. 8C.

As shown in FIG. 8D, the camera 12 is loaded into the second hollow tube 644, while the bougie 590 is loaded into the hollow tube 642 of the adaptor 640. The adaptor 640 can rotate clock-wise and counter-clockwise around the bougie. The adaptor 640 can slide distally and proximally along the bougie. This allow visualization of different tissue areas as needed.

Figure 8E:
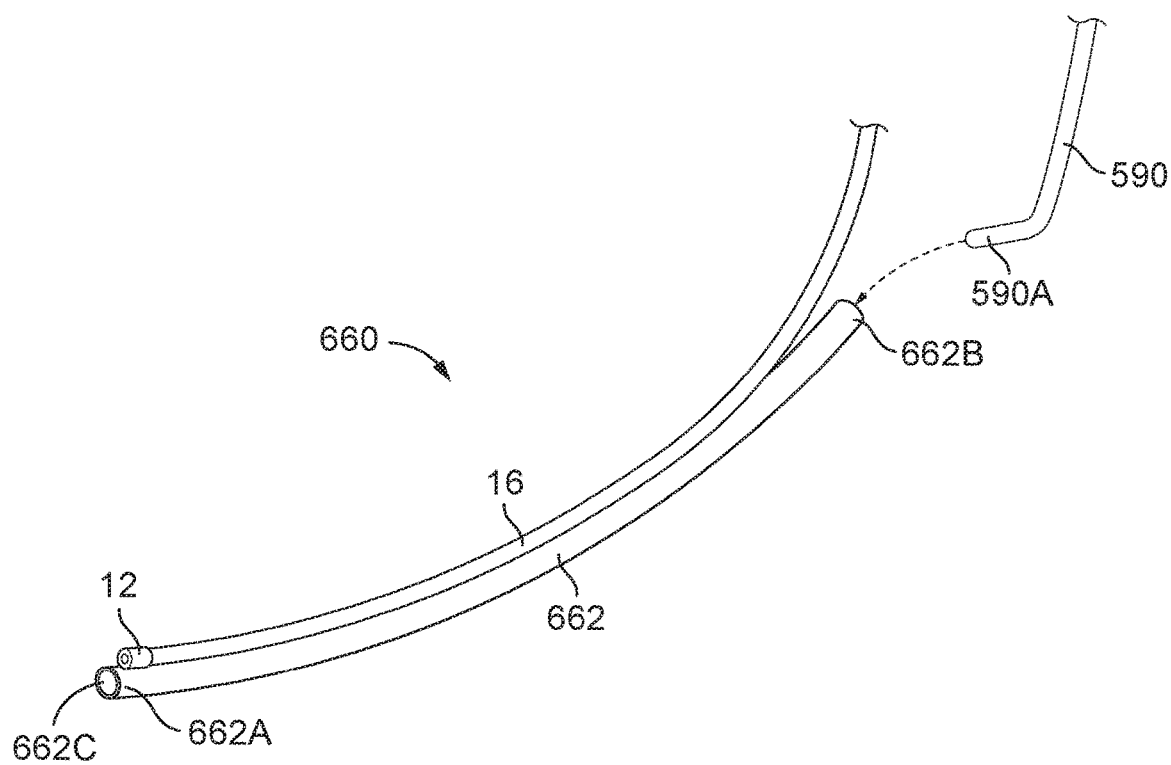
FIG. 8E depicts another embodiment of an adaptor comprising a hollow tube attached to a camera.

Referring to FIG. 8E, it provides a further embodiment of an adaptor according to this disclosure, generally 660. The adaptor 660 comprises a hollow tube 662 attached to the camera 12. The hollow tube 662 comprises a distal end 662A and a proximal end 662B. The camera 12 is attached to the hollow tube 662 externally and in proximity with the distal end 662A. The cable 16 runs along the length of the hollow tube 662.

Figure 8F:
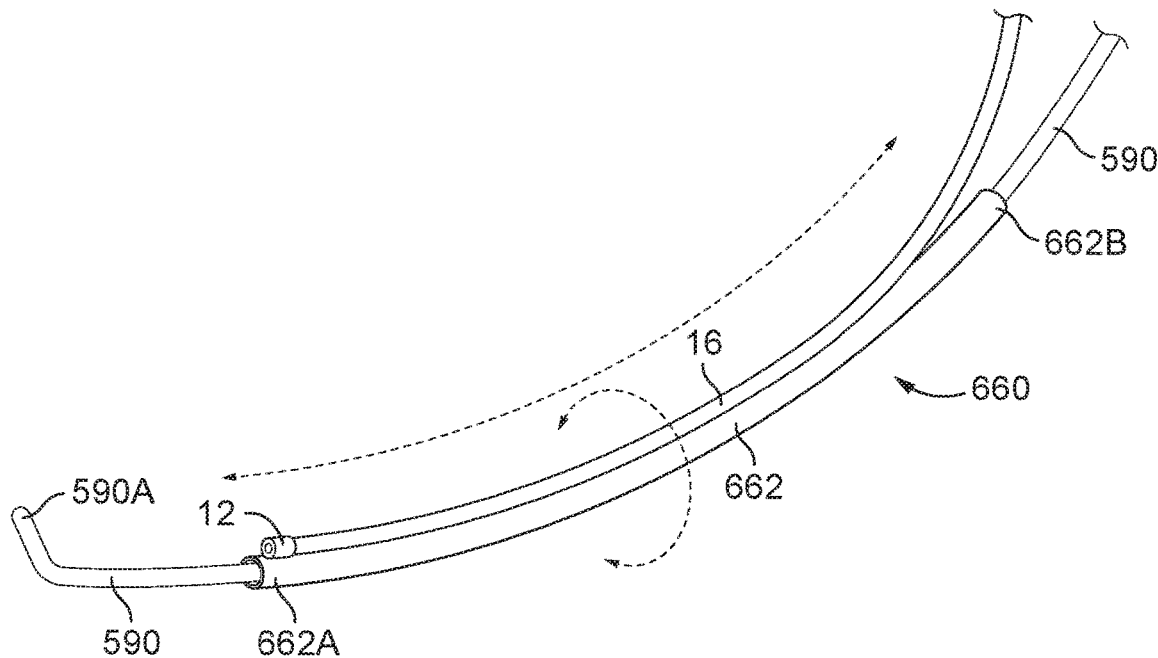
FIG. 8F depicts a bougie being inserted into the adaptor of FIG. 8E.

A bougie 590, or some other tool, can be placed into the hollow tube 662 as shown in FIG. 8F. The adaptor 660 can rotate clockwise and counter-clockwise around the bougie 590. The adaptor 660 can also slide distally and proximally along the length of the bougie 590. The adaptor 660 may comprise additional hollow tubes as was described in connection with adaptors 620 and 640.

Figure 8G:
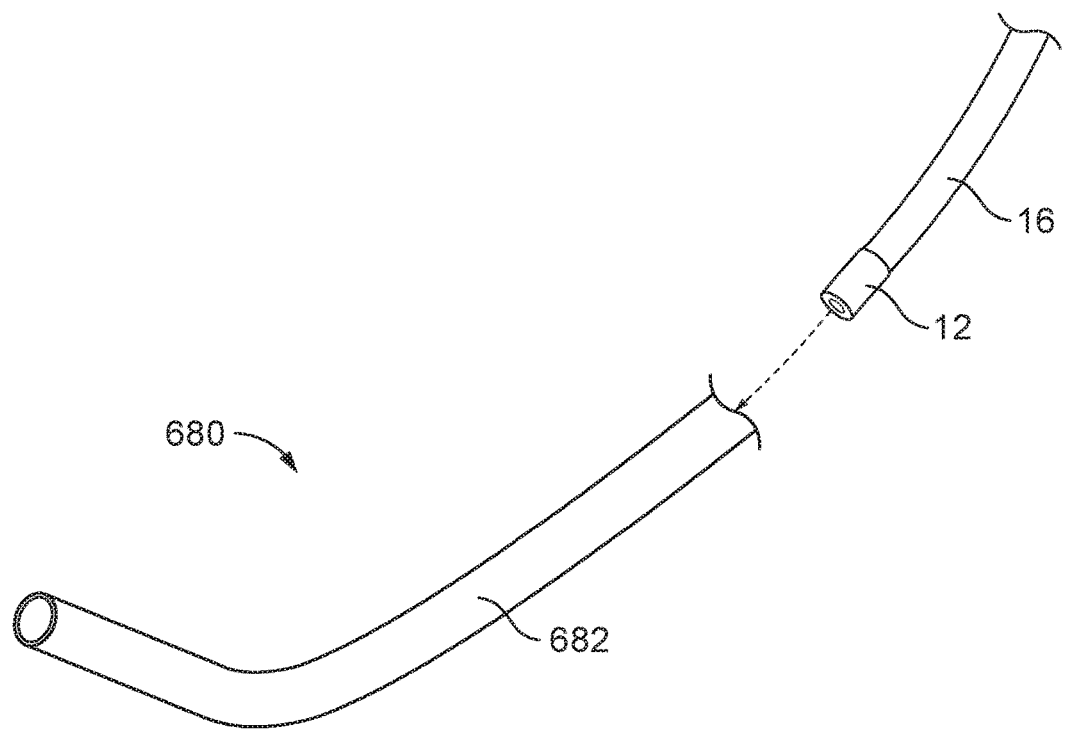
FIG. 8G depicts another embodiment of an adaptor according to this disclosure.
Figure 8H:
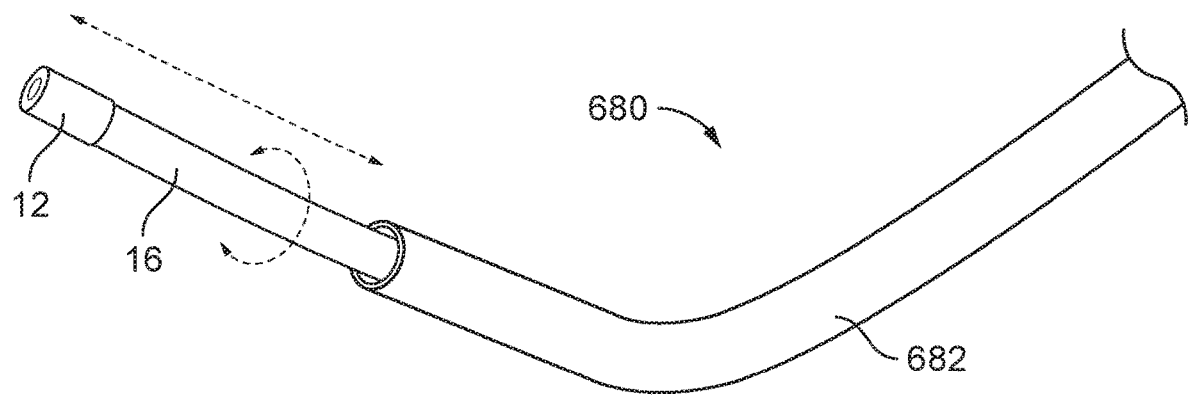
FIG. 8H depicts a camera being inserted and rotated in the adaptor of FIG. 8G.

Referring to FIG. 8G, it provides a further embodiment of an adaptor according to this disclosure, generally 680. The adaptor 680 comprises a hollow tube 682, a portion of which is shown in FIG. 8G. The camera 12 with cable 16 can be inserted into the hollow tube 682. The hollow tube 682 is made of a plastic material which flexible enough to be curved into a shape needed for insertion. However, once curved, the hollow tube 682 will retain the shape. Any of the adaptors provided in this disclosure can be made of this material and have the property of retaining a shape they have been placed into. In alternative, an adaptor according to this disclosure can be made of a flexible material. FIG. 8H depicts the camera 12 inserted into the adaptor 680.

Figure 8I:
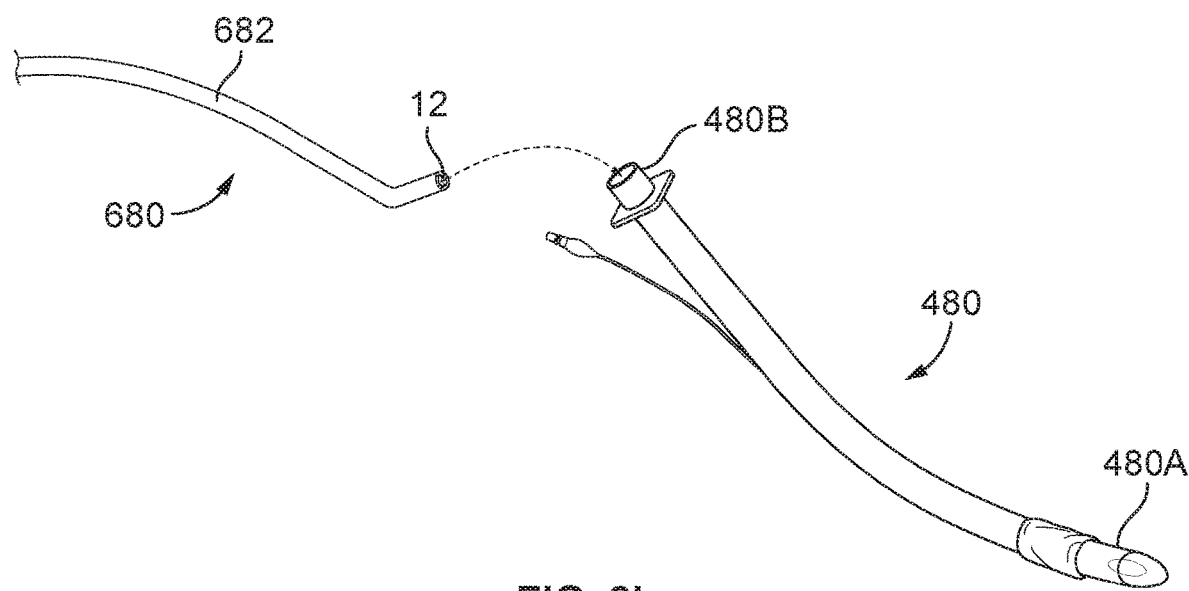
FIG. 8I depicts the assembly of the camera with the adaptor of FIG. 8G being inserted into an endotracheal tube.

FIG. 8I depicts how the assembly of FIG. 8H can be inserted into the endotracheal tube 480.

Figure 8J:
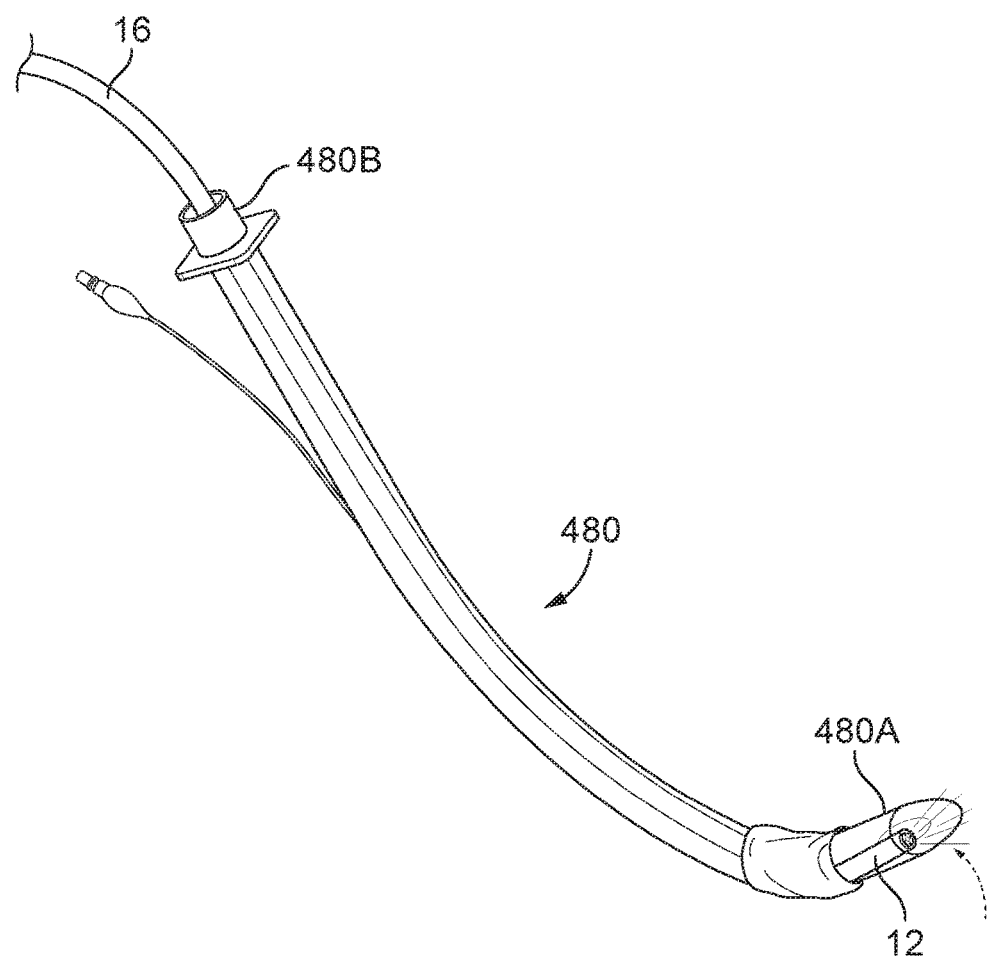
FIG. 8J depicts the endotracheal tube of FIG. 8I into which the adaptor hosting the camera is inserted.

FIG. 8J depicts the endotracheal tube 480 into which the adaptor 680 is inserted. The adaptor 680 is hosting the camera which is now positioned at the distal end 480A of the endotracheal tube 480. The camera cable 16 can protrude proximally to the proximal end 480B of the endotracheal tube 480. The camera 12 can also include a light source and shed light as shown in the drawing of FIG. 8J.

FIG. 8K depicts the adaptor 640 of FIG. 8C being combined with the camera 12 with cable 16 and a bronchoscope 648.

As was discussed in connection with FIG. 8C, the adaptor 640 comprises a hollow tube 642 with a distal end 642A and a proximal end 642B. The hollow tube 642 has an opening 642C at the distal end 642A and an opening 642D at the proximal end 642B.

At least one second hollow tube 644 is attached along the length of the hollow tube 642. The second hollow tube 644 has a distal end 644A and a proximal end 644B. In other embodiments, the adaptor 640 may comprise a plurality of second hollow tubes 644, for example, 2 or 3 or 4 of the second hollow tubes 644.

The second hollow tube 644 has an opening 644C at the distal end 644A. The second hollow tube 644 has an opening 644D at the proximal end 644B. The distal end 644A of the second hollow tube 644 is aligned with the distal end 642A of the hollow tube 642. The proximal end 644B of the second hollow tube 644 is aligned with the proximal end 642B of the hollow tube 642. A diameter of the second hollow tube 624 is compatible with a camera 12 such that the camera 12 connected to the cable 16 can be inserted through the proximal opening 644D into the second hollow tube 644. Since the distal end 644C is not sealed, the camera 12 can protrude distally from the second hollow tube 644.

In FIG. 8K, the bronchoscope 648 is being placed into the hollow tube 642 through the proximal opening 642D. The bronchoscope 648 comprises a plastic rod 650 attached to a mechanism 652 with a handle 654. The plastic rod 650 can be manipulated, e.g. curved in various directions, by toggling the handle 654 of the mechanism 652. Many prior art bronchoscopes comprise light and lens for viewing patient's tissues. With help of the adaptor 640, any bronchoscope, including those which do not comprise light and lenses, can be used with the camera 12 which provides continuous visualization. In order to combine the bronchoscope 648 with the adaptor 640, a distal end 650A of the rod 650 is inserted through the opening 642D into the hollow tube 642. The distal end 650A is then positioned near the distal end 642A inside the hollow tube 642. The distal end 650A of the rod 650 may protrude distally from the opening 642C of the hollow tube 642 of the adaptor 640.

The adaptor 640 may further comprise a stylet or rod 646 (not shown in the drawing of FIG. 8K) which runs along the hollow tube 642 for at least some of the length of the hollow tube 642 and provides a support and backbone to the adaptor 640 if needed.

Referring to FIG. 8L, it depicts the adaptor 640 hosting the rod 650 of the bronchoscope 648 in the hollow tube 642, while the camera is hosted in the hollow tube 644. Accordingly, the bronchoscope 648 can be manipulated under the continuous visualization by the camera 12.

Referring to FIGS. 8M and 8N, while the adaptor 640 is inserted into a patient, the rod 650 of the bronchoscope 648 can be manipulated and curved in different directions by toggling the handle 654. These manipulations are conducted under the continuous visualization by the camera 12.

Figure 9A:
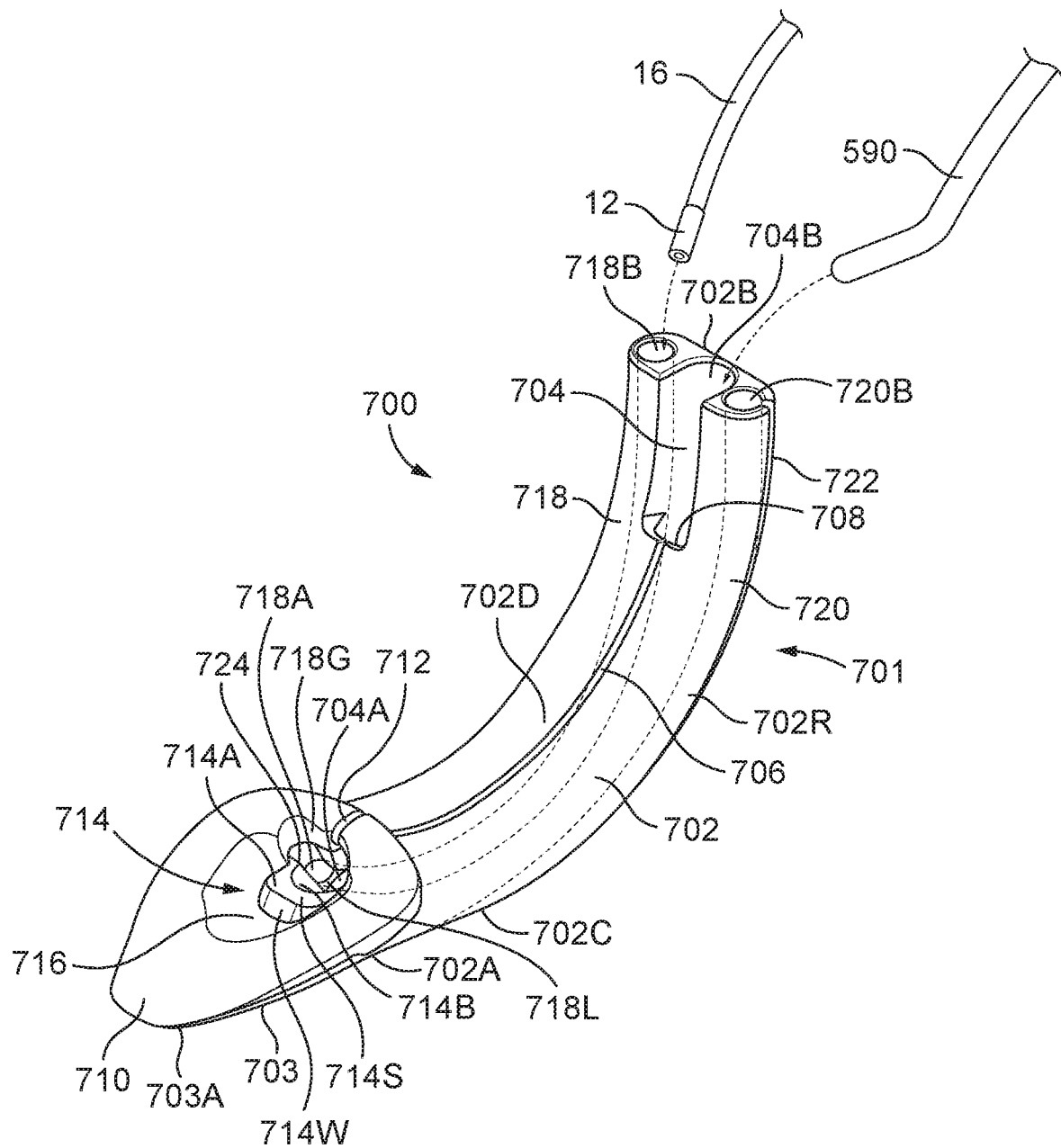
FIG. 9A depicts an oral airway device comprising a laryngeal cuff.

Referring to FIG. 9A, it provides a further embodiment of an oral airway device according to this disclosure, generally 700. The oral airway device 700 comprises a tubal body 701 which is curved (arched) anteriorly such that the oral airway device 700 follows the contour of the roof of a patient's mouth during insertion of the oral airway device 700. In this disclosure "anteriorly" is used in its standard anatomic meaning, e.g., the distal portion of the device 700 is curved toward subject's front.

The curved tubal body 701 of the oral airway device 700 is made by a wall 702 which has a length between a distal end 702A and a proximal end 702B. The wall 702 has a ventral surface 702D and its opposite dorsal surface 702C (not seen in the drawing of FIG. 9A). See also FIG. 9W, depicting a cross-sectional view of the tubal body 701.

Figure 9B:
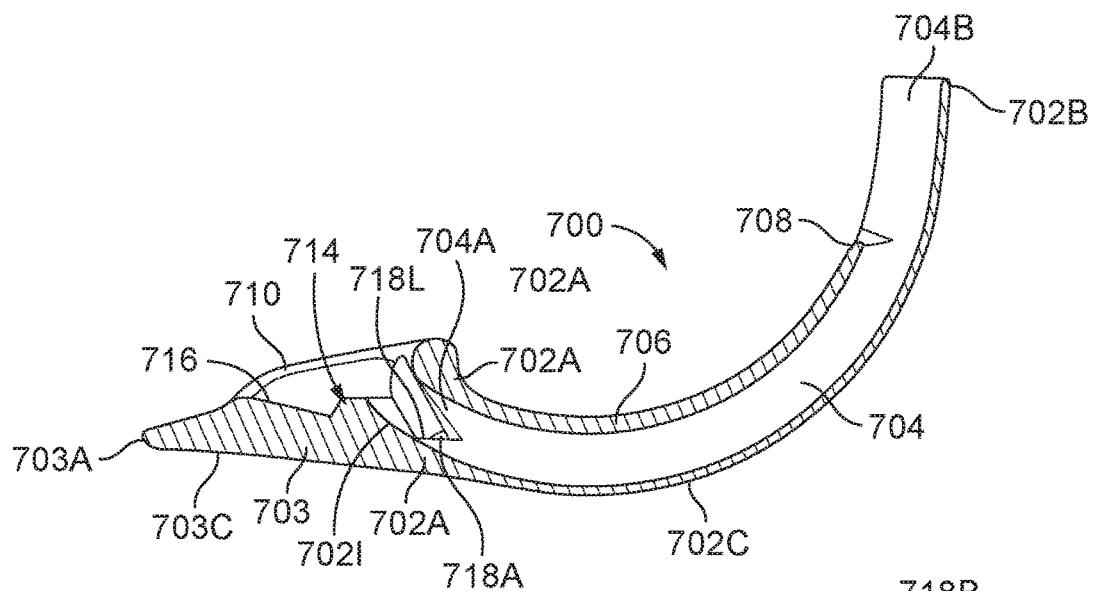
FIG. 9B is a longitudinal cross-sectional view through the central lumen of the oral airway device of FIG. 9A.
Figure 9C:
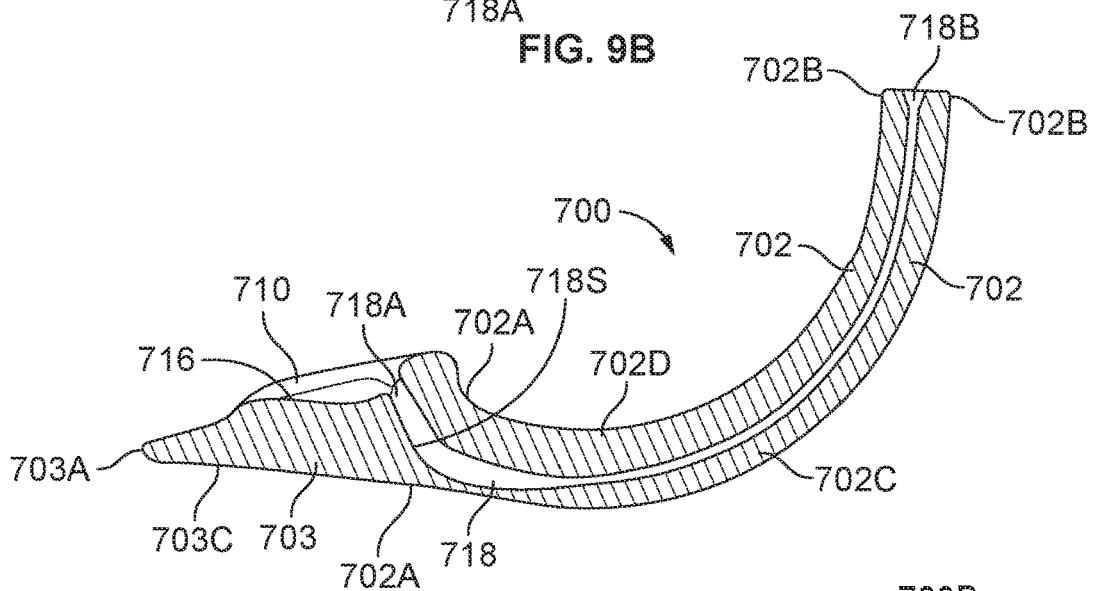
FIG. 9C is a longitudinal cross-sectional view through the camera channel of the oral airway device of FIG. 9A.
Figure 9D:
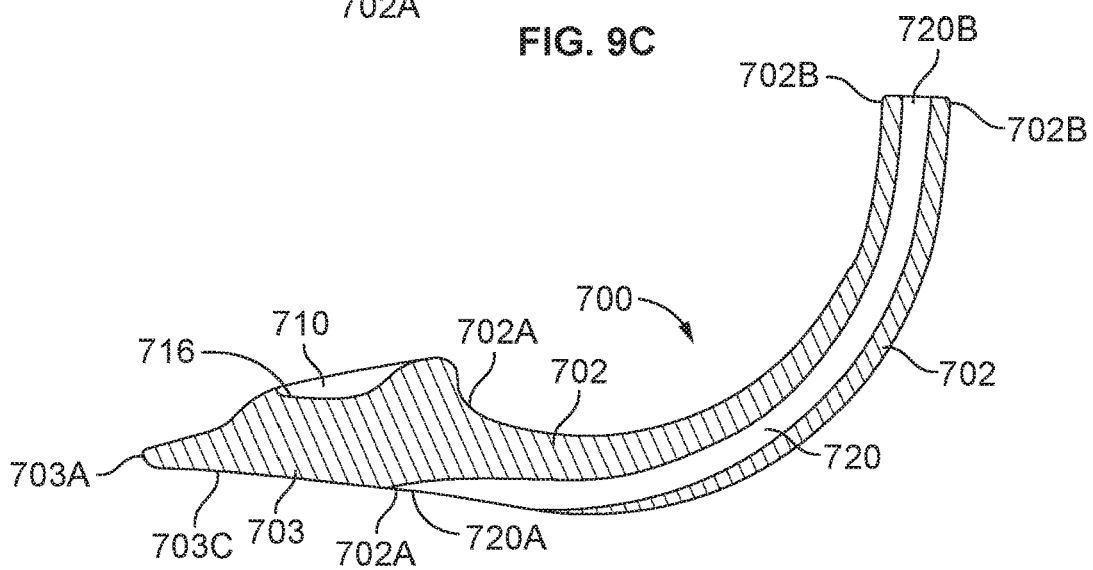
FIG. 9D is a longitudinal cross-sectional view through the gastric channel of the oral airway device of FIG. 9A.
Figure 9E:
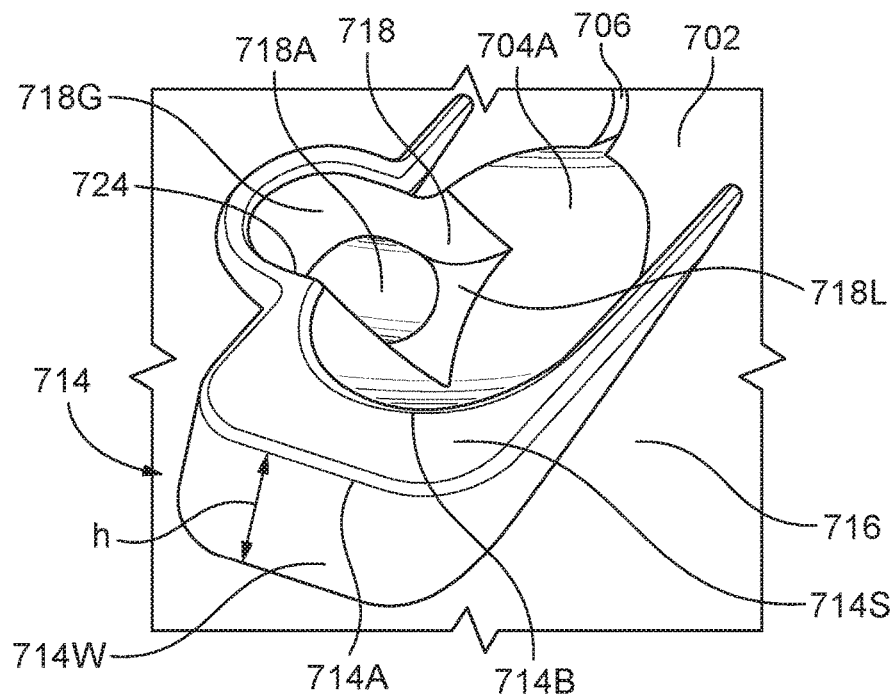
FIG. 9E depicts details of the central ramp of the oral airway device of FIG. 9A.
Figure 9F:
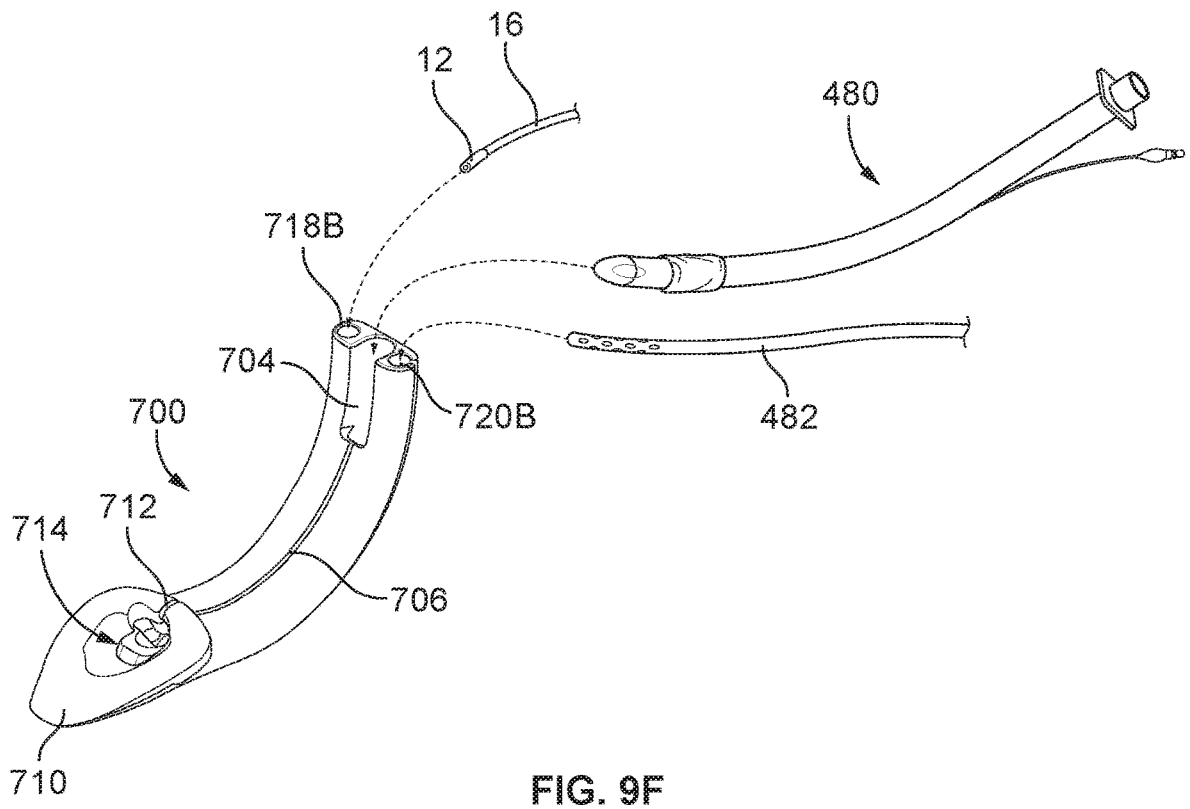
FIG. 9F depicts the oral airway device of FIG. 9A being assembled with an endotracheal tube, a camera and a suction tube.
Figure 9G:
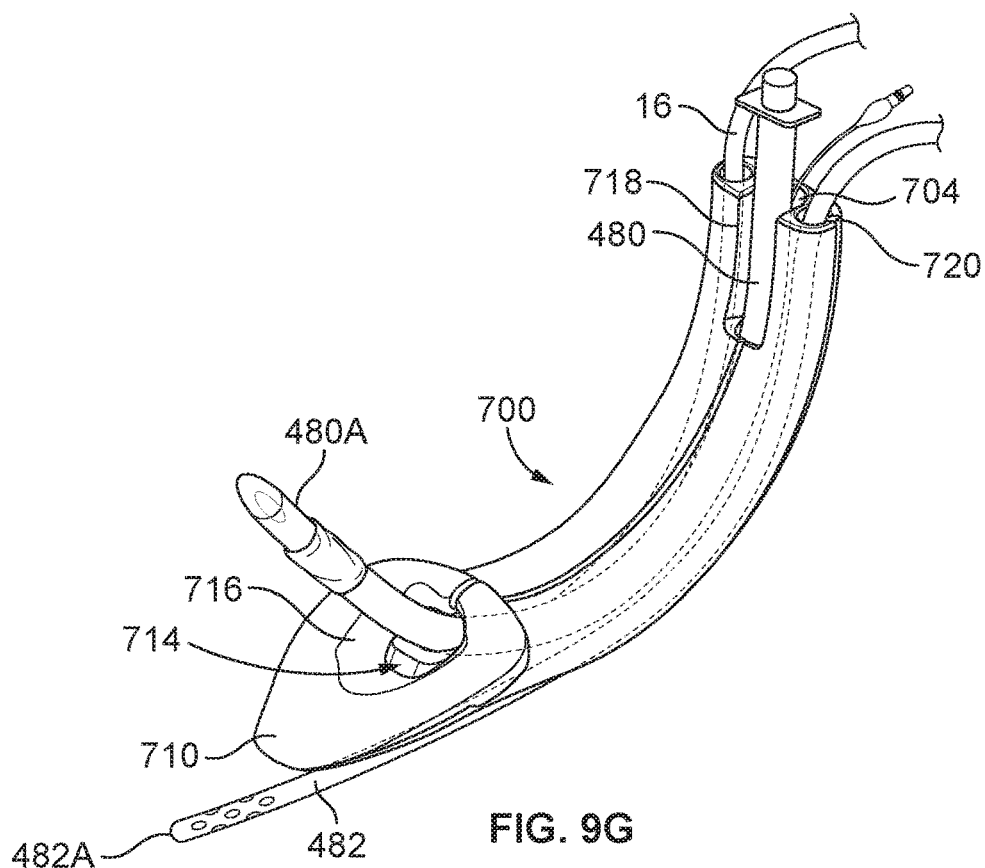
FIG. 9G depicts the oral airway device of FIG. 9A assembled with an endotracheal tube, a camera and a suction tube.
Figure 9H:
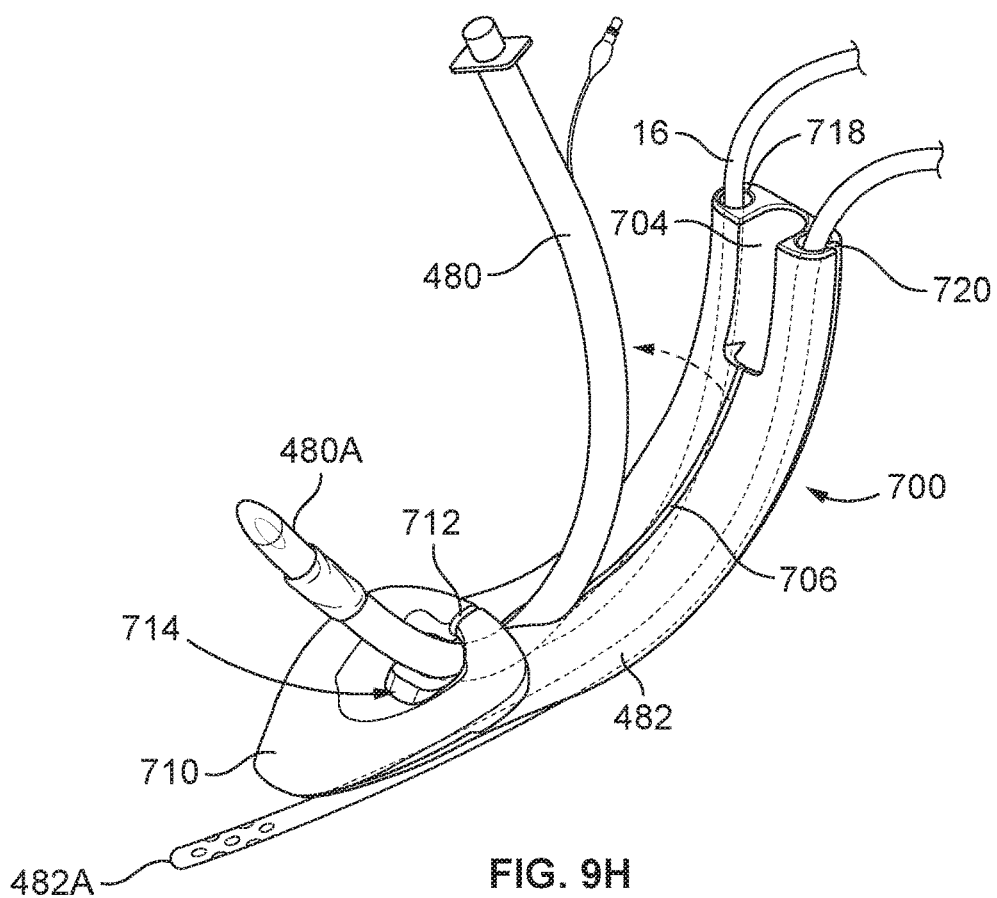
FIG. 9H depicts an endotracheal tube being separated from the assembly of FIG. 9G through the slits.
Figure 9L:
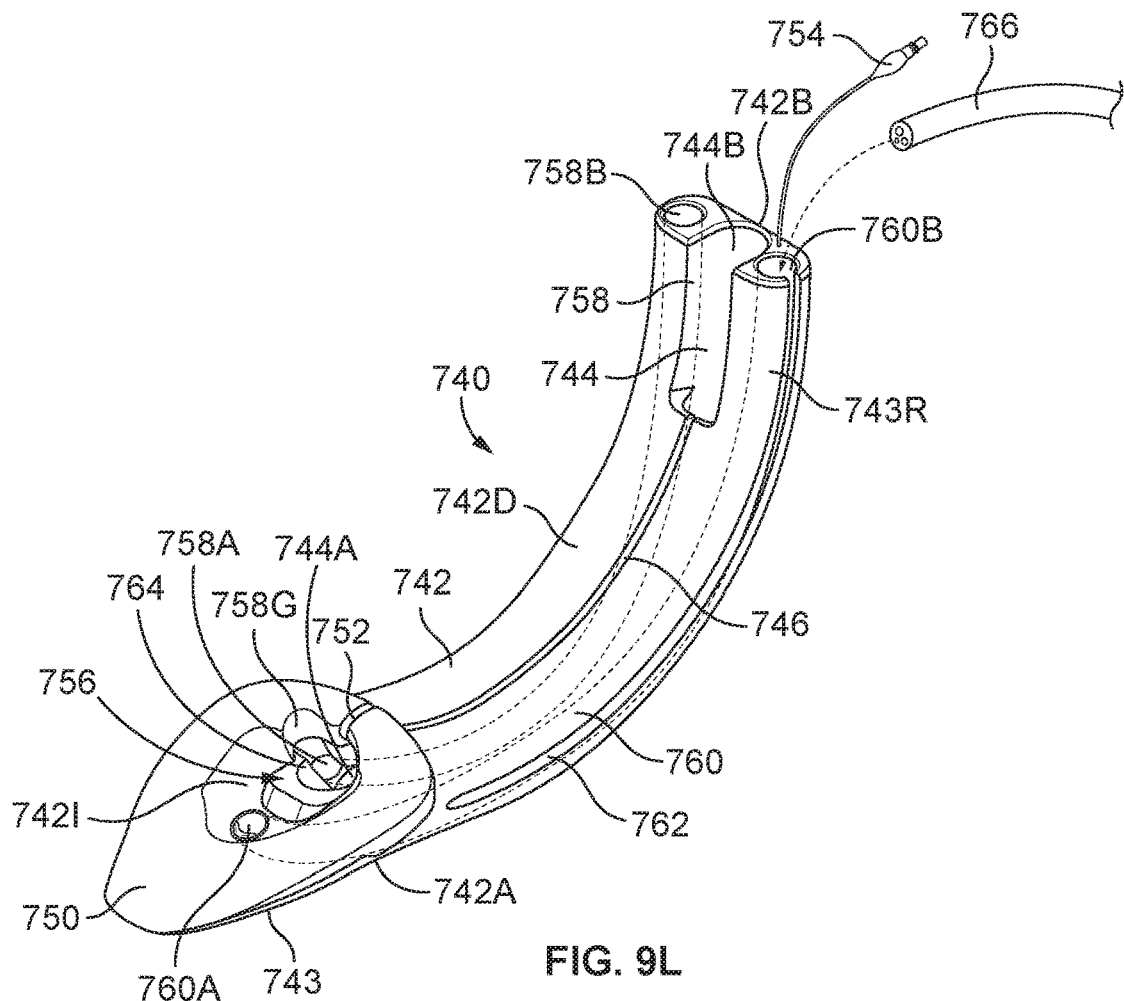
FIG. 9L depicts another embodiment of an oral airway device.
Figure 9M:
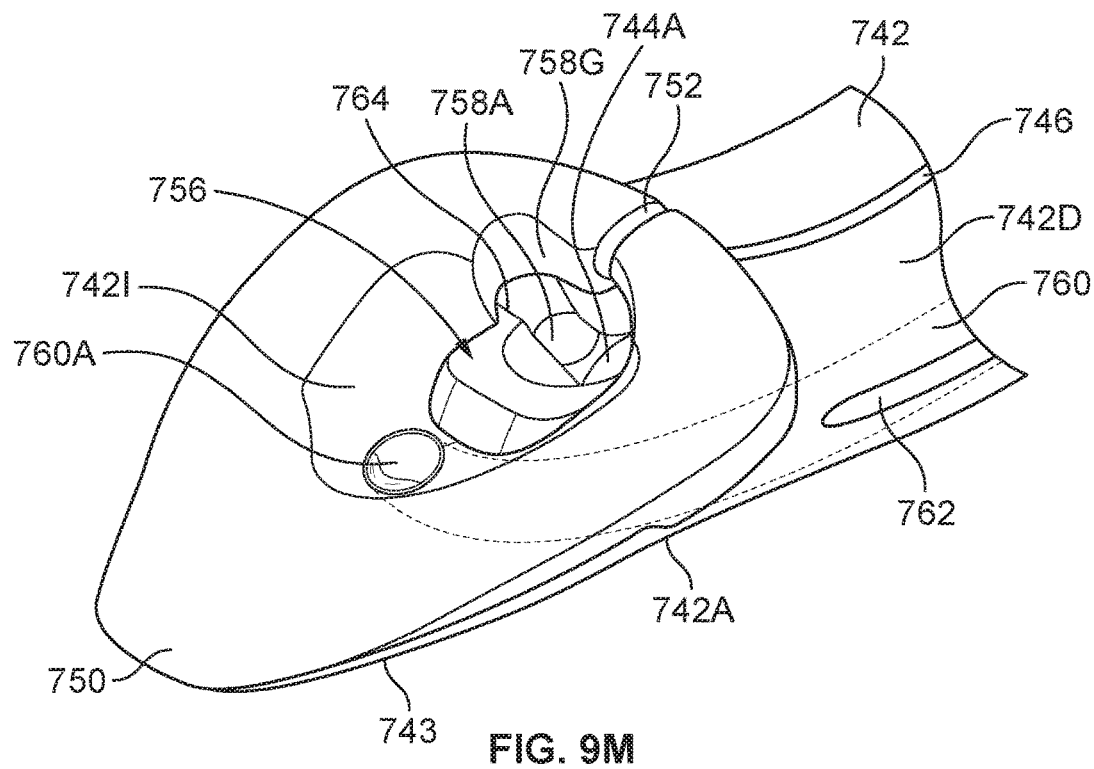
FIG. 9M is an enlarged distal portion of the oral airway device of FIG. 9L.
Figure 9R:
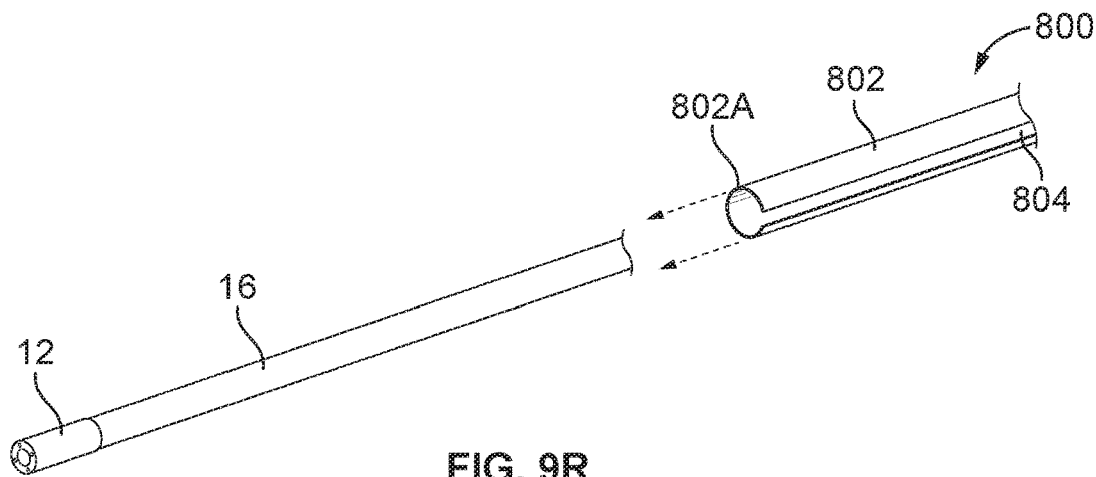
FIG. 9R depicts an adaptor with a slit for a camera and cable.
Figure 9S:
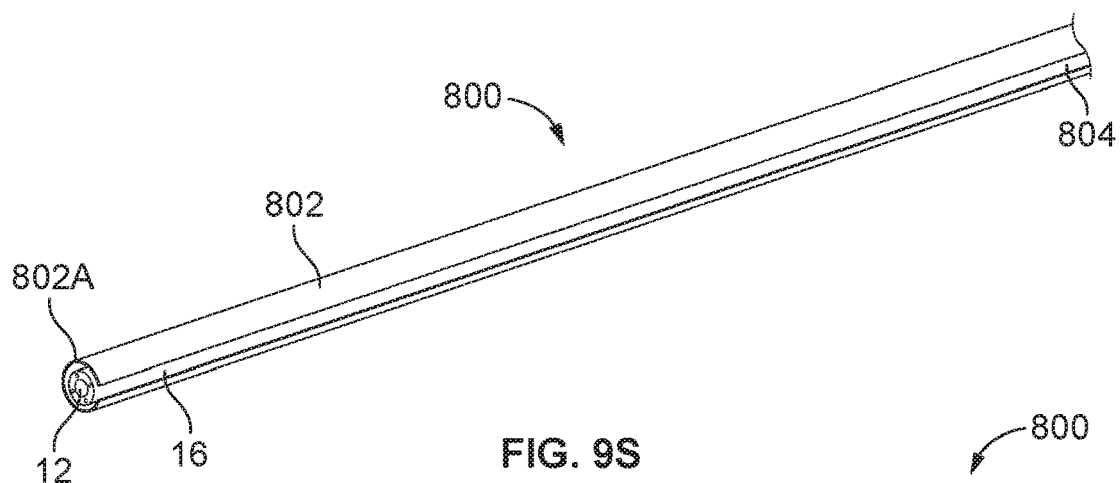
FIG. 9S depicts the adaptor of FIG. 9R hosting a camera and cable.
Figure 9T:
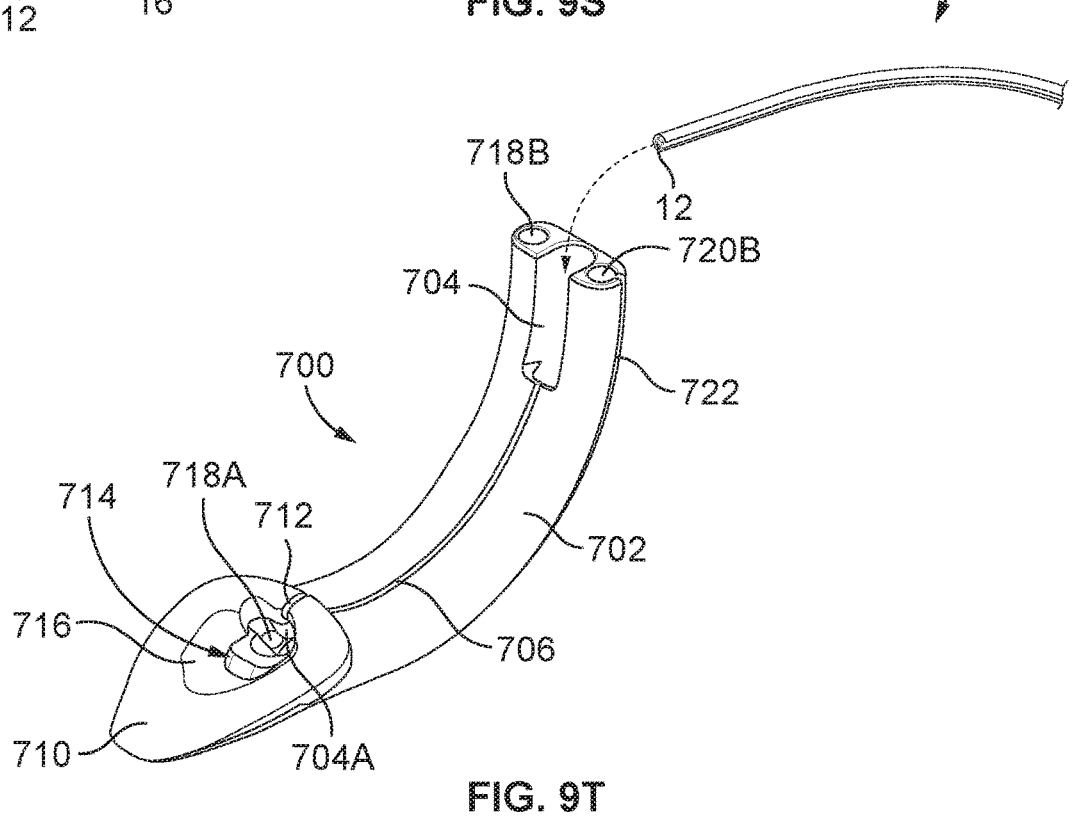
FIG. 9T depicts the assembly of FIG. 9S being combined with the oral airway device of FIG. 9A.
Figure 9U:
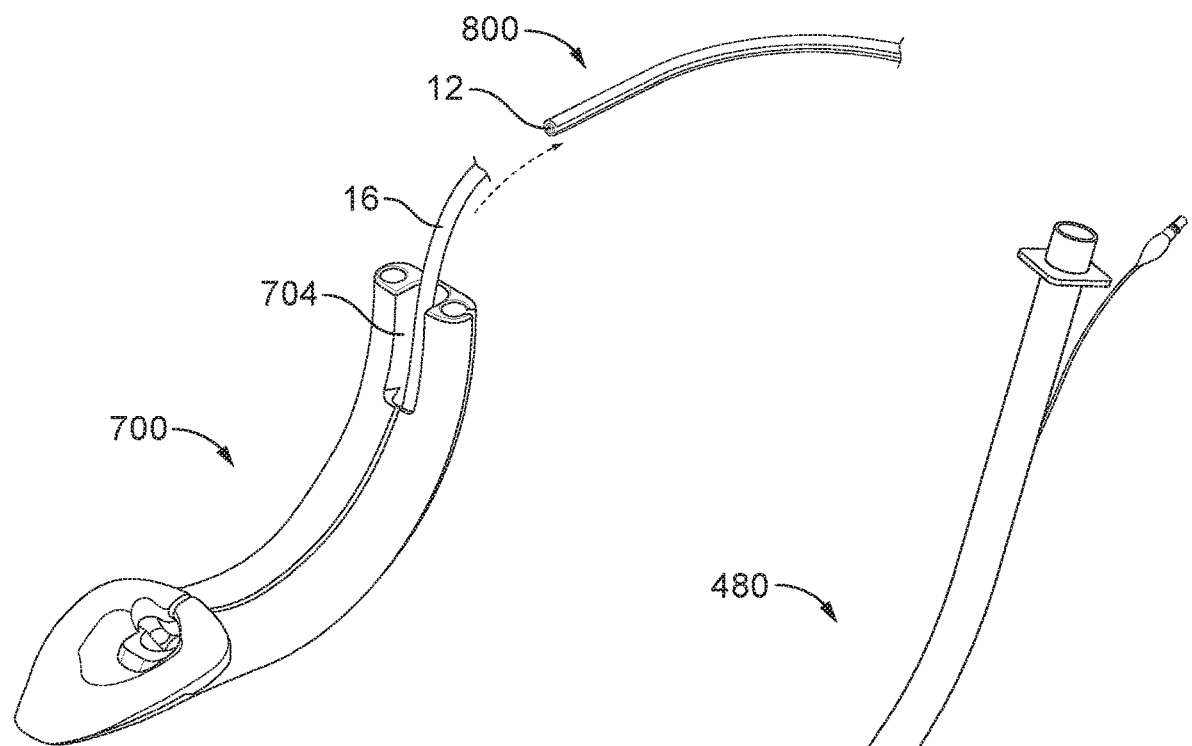
FIG. 9U depicts the assembly of FIG. 9S being combined with the oral airway device of FIG. 9A which hosts another camera.
Figure 9V:
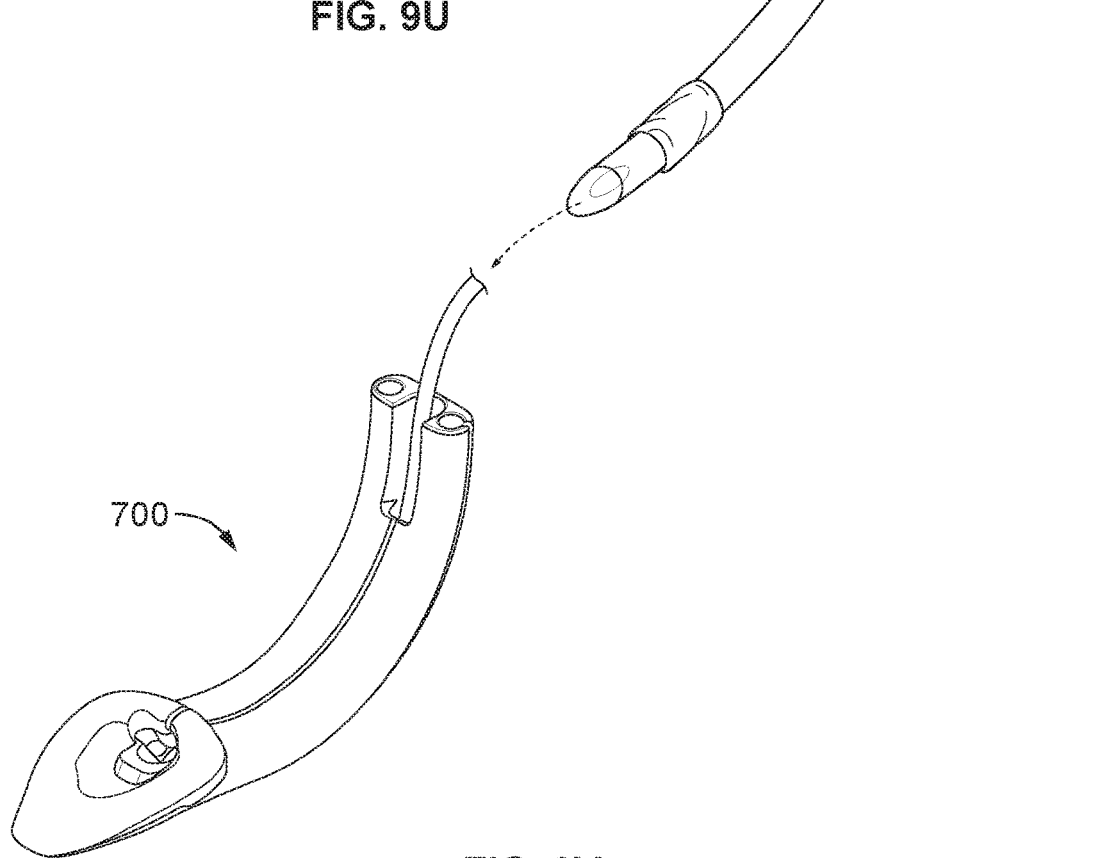
FIG. 9V depicts the assembly of FIG. 9S being combined with the oral airway device of FIG. 9A and an endotracheal tube.
Figure 9W:
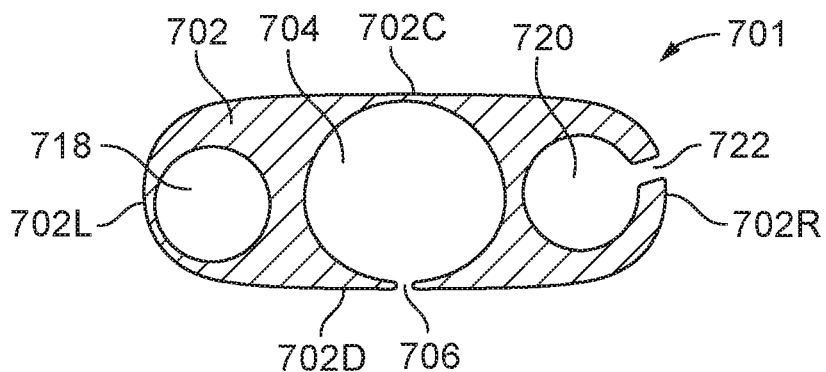
FIG. 9W is a cross-sectional view across the wall of the tubal body of the oral airway device of FIG. 9A.

In the drawing of FIG. 9W, the cross-section through the wall 702 shows a camera channel 718 in the wall 702, a central lumen 704 in the wall 702 and a gastric channel 720 in the wall 702. The dorsal surface 702C of the wall 702, the ventral surface 702D of the wall 702 and flanks 702L and 702R of the wall 702 are also shown, along with a slit 706 in the wall 702 which opens into the central lumen 704. The wall 702 can be made of a thermoplastic material which is flexible enough to be inserted into a patient's oral cavity, but also sufficiently firm to retain the curved shape. Conventional oral airway devices are tubes which are hollow plastic cylinders. Unlike the conventional oral airway devices, the wall 702 has a thickness and the tubal body 701 is not hollow. Instead, the central lumen 704 and the channels 718 and 720 are hollow passages in the wall 702 of the tubal body 701 which is filled with the thermoplastic material. See FIG. 9W.

Referring back to FIG. 9A, looking at the ventral surface 702D, from the proximal end 702B to the distal end 702A, the curved tubal body 701 is curved anteriorly in order to follow the contour of the roof of a patient's mouth during insertion and also in order to improve an alignment of the oral airway device 700 towards the laryngeal inlet.

The wall 702 comprises the dorsal surface 702C (not seen in the drawing of FIG. 9A, but see FIG. 9W), the ventral surface 702D which is opposite to dorsal surface 702C and two flanks (lateral surfaces): one on each side in between the surfaces 702C and 702D. In the drawing of FIG. 9A, the ventral surface 702D and the right flank 702R are shown. The left flank, 702L, is opposite to the right flank 702R and is not visible in the drawing of FIG. 9A, but see also FIG. 9W. Upon placement of the oral airway device 700 in a subject, the ventral surface 702D is typically positioned anterior, or in other words closer to the subject's front than the dorsal surface 702C. Upon placement of the device 700 in a subject, the proximal end 702B remains external and outside of the subject's mouth.

Because of the arch curvature, a length of the wall 702 is longer on the dorsal surface, 702C, than on the ventral surface, 702D.

At its distal end, the curved tubal body 701 ends with a tongue 703. The tongue 703 projects distally from the curved tubal body 701 and is tapered at its distal tip 703A. The tongue 703 has a ventral surface, 716, and a dorsal surface 703C, which is opposite to the ventral surface, 716, and which is not seen in FIG. 9A. However, the dorsal surface 703C of the tongue 703 is shown in FIGS. 9B, 9C and 9D as described in more detail below.

When looking at the tongue 703 from the ventral surface 716 as shown in FIG. 9A, the tip 703A of the tongue 703 may be oval, near oval, round or near round in order to facilitate insertion of the oral airway device 700 and to prevent or at least to minimize a trauma to patient's tissues.

The tongue 703 has the ventral surface 716 which serves as a platform on which several other elements are hosted, as discussed in more detail below. The ventral surface 716 may be flat or nearly flat which distinguishes the tongue 703 from laryngeal masks in which a body of the laryngeal mask is typically a bowl.

The curved tubal body 701 and the tongue 703 are made of a thermoplastic polymeric material which keeps the anterior curvature fixed or substantially fixed. The polymeric material is rigid enough to keep the shape of the oral airway device 700, including the anterior curvature. However, the material is flexible and soft enough such that there is a lesser impact on the patient's tissue during the insertion. Suitable materials may include synthetic plastic polymers, such as for example as polyvinyl chloride. Suitable materials may also include rubbers, such as for example as styrene-butadiene rubbers.

While, the curved tubal body 701 can keep its shape, a bougie can be incorporated into the wall 702, e.g. along the flank 702L, such that the bougie would provide additional backbone support for the oral airway device 700.

The wall 702 encircles a central lumen 704 which may be referred to in this disclosure as the endotracheal tube (ETT) lumen because the central lumen 704 may be used for placing an endotracheal tube. However, it will be understood that the ETT lumen 704 may be used for delivery of other breathing tubes and/or tools, such as for example as bougie 590, and/or devices suitable for managing airways. As discussed in more detail below, the ETT lumen 704 itself can be used for ventilating a patient if needed. Accordingly, the oral airway device 700 can be used with or without an endotracheal tube for managing airways.

The central lumen 704 is hollow and has a distal opening 704A and a proximal opening 704B. The proximal opening 704B opens at the proximal end 702B of the curved tubal body 702. The distal opening 704A opens to the ventral surface 716 of the tongue 703.

The central lumen 704 may be fully encircled by the wall 702 or the wall 702 may have a slit 706 as shown in FIG. 9A. The slit 706 runs along the distal-proximal 702A-702B axis on the ventral surface 702D of the wall 702 in the embodiment of FIG. 9A. In addition to the slit 706 or instead of the slit 706, some proximal portion on the ventral surface 702D may be absent as shown in FIG. 9A such that some proximal portion of the central lumen 704 is open on the ventral surface 702D and is not covered by the wall 702. In other words, the curved tubal body 701 may have a proximal recess 708 which opens into the central lumen 704. In other embodiments, the device 700 does not have the slit 706 or the slit 706 is located on the dorsal surface 702C instead of the ventral surface 702D.

A medical device, such as for example an endotracheal tube or any other tool or device suitable for managing patient's airways or a camera, can be placed in the central lumen 704 or be removed from the central lumen 704 by pushing apart the edges of the wall 702 along the slit 706.

In the embodiment of FIG. 9A, the wall 702 has the slit 706 which runs longitudinally along the distal-proximal 702A-702B axis on the ventral surface 702D. In other embodiments, the slit 706 may be placed at other surfaces, e.g. the dorsal surface 702C of the wall 702, so long the slit 706 is located such that a practitioner can access the central lumen 704 through the slit 706 by pushing apart the wall 702 at the slit 706.

In some embodiments, the slit 706 may be narrow such that the edges of the wall 702 touch or almost touch along the length of the slit 706. In some embodiments, the slit is sealable. In these embodiments, one of the edges of the wall 702 along the slit 706 comprises a groove and the other edges of the wall 702 comprises a ridge which interlocks with the groove, and thereby creates a seal through the slit 706. The seal can be reopened as needed.

In some embodiments, the slit 706 is a perforation line in the wall 702 which can be converted into an opening into the central lumen 704 by opening the wall along the perforation line. In other embodiments, the slit 706 is a gap such that there is always a gap between the edges of the wall 702 along the slit 706 and the edges of the wall 702 do not touch along the length of the slit 706. At least in some further embodiments, the wall 702 does not comprise the slit 706.

Referring to FIG. 9B, it is a longitudinal cross-sectional view through the central lumen 704 of the oral airway device 700 along the distal-proximal axis 702A-702B, showing the central lumen 704 inside the wall 702. All elements are labeled as in connection with FIG. 9A. A cross-section through the tongue 703 is shown, including its distal tip 703A, the ventral surface 716 and the dorsal surface 703C.

The curved tubal body 701 is curved anteriorly. Accordingly, the central lumen 704 which is a passage inside the wall 702 is also curved anteriorly.

Furthermore, some distal portion, 702I, of the wall 702 is sloped within the central lumen 704 near the tongue 703. This structure of the central lumen 704 determines an angle above the tongue 703 at which an endotracheal tube (or any other device or tool hosted in the central lumen 704) projects from the distal opening 704A of the central lumen 704.

The central lumen 704 is sloped at a predetermined angle such that the central lumen 704 projects from the distal opening 704A an endotracheal tube hosted in the central lumen 704 at an angle which is at least 30 degrees to the dorsal surface 703C of the tongue 703. In some embodiments, the angle is in the range from 30 degrees to 80 degrees. More preferably, the central lumen 704 is sloped and projects an endotracheal tube from the distal opening 704A at an angle in the range from 50 degrees to 80 degrees from the dorsal surface of the tongue 703. Most preferably, the central lumen 704 is sloped at an angle is the range from 60 degrees to 70 degrees to the dorsal surface 703C of the tongue 703. It will be appreciated by a person of skill that in some other embodiments, such as for example in pediatric applications, the angle may be different and may be adjusted as needed.

Referring back to FIG. 9A, in addition to the central lumen 704, the wall 702 comprises at least two peripheral hollow channels, 718 and 720. See also FIG. 9W. In some embodiments, the channel 720 may be absent, as discussed in more detail below.

The channel 718 is a hollow passage in the wall 702. See FIG. 9A and also FIG. 9W.

As shown in FIG. 9A, the channel 718 may be used for inserting the camera 12 with cable 16 and/or some other tools, e.g. a bougie, or devices. The channel 718 may be referred in this disclosure as the camera channel 718. It will be appreciated, that the channel 718 may be used for insertion of other tools and/or devices and that a camera may be inserted into other channels, e.g. the channel 704 and/or channel 720. The camera channel 718 can be also used to spray patient's tissues with a medication and/or to aspirate secretion.

The camera channel 718 has a proximal opening 718B which is an inlet into the camera channel 718 and which is positioned at the proximal end 702B of the wall 702. The camera channel 718 runs along the distal-proximal 702A-702B axis of the wall 702. The camera channel 718 ends with a distal opening 718A which is an outlet from the camera channel 718. The camera channel 718 is a peripheral channel. See the peripheral position for the proximal opening 718B in comparison to the central positioning of the proximal opening 704B of the central lumen 704 in the drawing of FIG. 9A, as well as shown in FIG. 9W.

A camera 12 with cable 16 can be inserted through the proximal opening 718B in the camera channel 718. Any camera suitable for visualization of patient's organs can be used in the oral airway device 700. The camera 12 is insertable and removable from the camera channel 718. A position of the camera 12 at the distal opening 718A of the camera channel 718 can be adjusted as needed in order to monitor patient's tissues and passage of the oral airway device 700 through the patient's oral cavity and into a pharynx during placement.

The oral airway device 700 when equipped with a camera can provide continuous visualization of patient's larynx and vocal cords. This facilitates an accurate and rapid placement of an endotracheal tube which can be accomplished without multiple and lengthy insertion attempts. The device 700 may comprise more than one cameras. For example, one of the cameras may be inserted into the camera channel 718, while the other camera can be placed in the central lumen 704 together with a bougie and/or an endotracheal tube.

In the drawing of FIG. 9A, the distal opening 718A is positioned near the distal opening 704A from the central lumen 704 such that when a camera is inserted into the channel 718 and protrudes through the distal opening 718A, the camera can provide visualization of a distal end of the device 700 and insertion of the device 700 and then also a placement of an endotracheal tube can be guided under the continuous visualization from the camera. The distal opening 718A of the camera channel 718 preferably is not sealed such that a camera can protrude distally from the camera channel 718. However, in some embodiments (not shown in FIG. 9A), the distal opening 718A of the camera channel 718 may be sealed with a window.

In some embodiments, the camera channel 718 is a hollow passage in the wall 702 and the camera channel 718 is completely separated from the ETT lumen 704, as also shown in FIG. 9W.

In other embodiments, the camera channel 718 is a semi-lumen which is connected to the ETT lumen 704 with a gap or slit. In further embodiments, there is a slit that runs along the length of the camera channel 718 on one of the surfaces of the wall 702 (not shown in FIG. 9A). In these embodiments, a camera can be inserted and removed from the camera channel 718 by being pulled through the slit.

Referring to FIG. 9C, this is a longitudinal cross-sectional view through the camera channel 718 showing that the camera channel 718 is a hollow passage in the wall 702. The camera channel 718 is curved anteriorly. The camera channel 718 is also sloped at its distal portion 718S near the distal opening 718A from the dorsal surface 703C of the tongue 703. A camera (or any other device) placed in the camera channel 718 is projected from the camera channel 718 at a predetermined angle because of the sloped structure of the camera channel 718.

When a device, such as for example a camera, is hosted in the camera channel 718 and the distal end of the camera protrudes distally from the camera channel opening 718A, the device/camera is projected from the camera channel at a predetermined angle which is defined by the slop of the camera channel 718. The projected device/camera is then supported at that angle by a camera ramp 724.

In some embodiments, the predetermined angle for the camera channel is in the range from 30 degrees to 80 degrees from the dorsal surface 703C of the tongue 703. More preferably, the angle is in the range from 50 degrees to 70 degrees. Most preferably, the angle is in the range from 55 degrees to 65 degrees. However, in other applications, such as for example in pediatric applications, a camera can be projected from the camera channel 718 at some other angle, e.g. 10-40 degrees to the dorsal surface 703C of the tongue 703.

The predetermined angle of the camera channel 718 is optimized such that the camera channel projects a camera at an angle which allows the camera to visualize the tip of the endotracheal tube hosted in the central lumen 704. It is important to note that camera channel 718 and the central lumen 704 may be designed with different slops from the dorsal surface 703C of the tongue 70s such that a camera hosted in the camera channel 718 projects at an angle different from an angle at which an endotracheal tube is projected from the central lumen 704.

In some embodiments, the projecting angle of the central lumen 704 may be greater than the projecting angle of the camera channel 718, both angles calculated from the dorsal surface 703C of the tongue 703. In some embodiments, the projecting angle of the central lumen 704 may be 5 to 10 degrees greater than the projecting angle of the camera channel 718. In other embodiments, the projecting angle of central lumen 704 may be lower than the projecting angle of the camera channel 718. In some embodiments, the projecting angle of the central lumen 7004 may be 5 to 10 degrees lower than the projecting angle of the camera channel 718. In other embodiments, both projecting angles are the same or substantially the same.

In some embodiments, the central lumen 704 is sloped at 55 to 75 degrees to the dorsal surface 703C of the tongue 703 and the camera lumen 718 is sloped at 50 to 70 degrees to the dorsal surface 703C of the tongue 703.

Because a camera can be manipulated to slide along the camera channel 718 independently from an endotracheal tube, the camera position relative to the distal tip of an endotracheal tube hosted in the central lumen 704 may be adjusted as may be needed. For example, a camera may be positioned closer or further away from the distal end of an endotracheal tube protruding distally from the distal opening 704A of the central lumen 704. One the technical advantages provides by the present oral airway device, a camera can be positioned proximally to the tip of an endotracheal tube.

Referring back to FIG. 9A, the oral airway device 700 may further comprise one or more camera channel guiding means for elevating an emerging camera or any other tool above the ventral surface 716. The guiding means may also guide an emerging tip of a device or tool, e.g. a camera and/or bougie, emerging from the distal opening 718A, toward the central line of the ventral surface 716 such that the emerging tip of the camera and/or a bougie, or any other device or tool hosted in the channel 718, is better aligned with a distal end of an endotracheal tube emerging from the distal opening 704A of the central lumen 704.

The guiding means may include one or more of the following: 1) a ledge, shown as ledge 718L in the drawing of FIG. 9A, which helps in aligning the distal tip of a camera with the distal tip of an endotracheal tube; 2) a wall guard which guides the emerging tip toward the central line of the ventral surface 716, shown as the wall guard 718G in the FIG. 9A; 3) a ramp positioned in front of the distal opening 718A and/or inside the distal opening 718A, shown as a camera channel ramp 724 in FIG. 9A; and 4) any combination thereof.

While the camera channel 718 is generally a hollow channel or a tunnel in the wall 702 which is separated from the central lumen 704 by the wall material, the camera lumen 718 may have the ledge 718L. Thus, the distal opening 718A and the distal opening 704A may be aligned such that the emerging tip of the device or tool placed in the camera lumen 718 is aligned with a tip of an endotracheal tube emerging from the distal opening 704A.

The oral airway device 700 may comprise the wall guard 718G positioned such that when a tip of a camera is emerging from the distal opening 718A, the wall guard 718G guides the tip of the camera and/or any other device, e.g. a bougie, toward the central line of the ventral surface 716 such that the camera and/or a bougie is aligned with a distal end of an endotracheal tube emerging from the distal opening 704A of the central lumen 704. The wall guard 718G may be a fold suspending in front a portion the distal opening 718A.

The oral airway device 700 may comprise the camera channel ramp 724 positioned distally and in front of the camera channel distal opening 718A. The camera channel ramp 724 supports a camera projecting from the sloped camera channel 718.

In some other embodiments, the oral airway device 700 may comprise at least one camera (not shown) which may be built in the wall 702, sealed to the wall 702 or is connected slidably along the wall 702. In further embodiments, the oral airway device 700 may comprise multiple cameras. The oral airway device 700 may further comprise a sound and/or heart tone sensor which can be combined with a camera or it can be a separate device. One or more cameras may comprise a built-in light source. In alternative, the wall 702 may have a built-in light source which is independent from a camera.

In further embodiments, the oral airway device 700 may comprise an esophageal stethoscope (not shown) which may be either built-in the wall 702 or the esophageal stethoscope may be insertable into the channel 718, the ETT lumen and/or the channel 720. In further embodiments, the oral airway device 700 may comprise a temperature probe (not shown) which may be either combined with the esophageal stethoscope (not shown) or the temperature probe may be built-in the wall 702 or the temperature probe may be insertable into the channel 718, the ETT lumen and/or the channel 720.

A central ramp 714 is positioned on the ventral surface 716 and rises above the ventral surface 716. The central ramp 714 is located distally to and in front of the opening 704A from the central lumen 704. The central ramp 714 comprises a distal wall 714W supporting a ramp surface 714S with a proximal edge 714B and a distal edge 714A.

The central ramp 714 facilitates and guides insertion of an endotracheal tube or other medical devices or tools. When an endotracheal tube (or any other device or tool) is hosted in the central lumen 704 and a distal end of the endotracheal tube (or any other device or tool) is protruding distally from the distal opening 704A of the central lumen 704, the central ramp 714 supports and elevates the protruding distal tip above the ventral surface 716 of the tongue 703.

The structure of the central ramp 714 will now be described with reference to FIG. 9E which depicts a portion of the ventral surface 716 to which the central ramp 714 is attached. The central ramp 714 is located distally and in front of the distal opening 704A of the central lumen 704 in the wall 702.

The height of the ramp 714, (shown ash in the drawing of FIG. 9E) is designed such that during insertion of the oral airway device 700, the central ramp 714 comes in contact with the arytenoids and/or lower portion of larynx. The central ramp 714 prevents the oral airway device 700 from going into an upper esophagus.

When a device or tool, such as an endotracheal tube, is inserted into the central lumen 704 and a distal tip of the device or tool protrudes distally from the opening 704A of the central lumen 704, the central ramp 714 elevates and supports the tip of the device or tool above the ventral surface 716 at a predetermined angle which may be in the range from 50 to 80 degrees, and preferably in the range from 60 to 70 degrees from the distal surface 703C of the tongue 703.

The oral airway device 700 guides an endotracheal tube and/or any other device or tool at an angle optimal for directing the endotracheal tube between the vocal cords. Thus, the central ramp 714, the arch-like curvature of the wall 702 and the sloped central lumen 704 minimize a risk of esophageal intubation or snaring on the arytenoids.

In the drawing of FIG. 9E, the distal opening 718A from the camera channel 718 is also shown, along with the camera channel ramp 724 and the camera channel ledge 718L. The camera channel guard 718G is also shown.

Returning to the FIG. 9A, in the embodiment of FIG. 9A, the oral airway device 700 comprises a second peripheral channel 720 which may be referred in this disclosure as the gastric channel 720. In other embodiments, the gastric channel 720 may be absent. In some other embodiments, the oral airway device 700 may comprise additional channels.

The gastric channel 720 is a hollow passage in the wall 702 which runs along the distal-proximal 702A-702B axis of the wall 702. The gastric channel 720 opens with a proximal opening 720B at the proximal end 702B of the wall 702. The gastric channel 720 may have a slit 722 which runs along at least a portion of the length of the gastric channel 720 and which opens the gastric channel 720 on one of the surfaces of the wall 702. In the embodiment of FIG. 9A, the slit 722 opens to the right flank 702R. In alternative embodiments, the slit 722 can open on the dorsal surface 702C of the wall 702. In further embodiments, the slit 722 may be absent.

The gastric channel 720 ends with a distal opening 720A (not shown in the drawing of FIG. 9A) on the dorsal surface 702C of the wall 702 or the distal opening 720A may open on the dorsal surface of the tongue 703 (not seen in the drawing of FIG. 9A).

The gastric channel 720 can be used for aspirating fluids and stomach contents by inserting a suction tube in the gastric channel 720. In this disclosure, the gastric channel 720 may be referred as the esophageal channel 720. The gastric channel 720 may be used for aspirating stomach contents and in order to prevent vomiting.

Referring to FIG. 9D, this is a longitudinal cross-sectional view through the esophageal channel 720 showing its relative position in the wall 702. All elements are labeled as in connection with FIG. 9A. See also FIG. 9W.

The gastric channel 720 can be also used for inserting other tools, including, but not limited to, a bougie, stylet, forceps, esophageal stethoscope and/or camera.

In other embodiments, the gastric channel 720 is a semi-lumen which is connected to the ETT lumen 704 with a slit (not shown in FIG. 9A).

Because the oral airway device 700 assembles several tools together, one practitioner can manipulate all these tools as needed, and perform a placement of the oral airway device 700.

As can be appreciated by a person of skill, in some embodiments, the channels 718 and 720 may be interchangeable, i.e. a camera can be inserted into either of the two channels, as needed. In further embodiments, the oral airway device 700 may have more than two channels in the wall 702. These additional channels may be located peripherally to the ETT lumen 704. In some procedures, a camera can be also placed into the ETT lumen 704, if needed.

Referring to FIG. 9A, a non-inflatable laryngeal cuff 710 is formed and attached around the perimeter of the ventral surface 716 of the tongue 703, including the tongue tip 703A. The laryngeal cuff 710 is also attached to the wall 702 at the flanks 702L, 702R and on the ventral surface 702D. Thus, the laryngeal cuff 710 forms a donut-like cushion of the oral airway device 700.

The laryngeal cuff 710 is shaped such that it corresponds to a contour of the larynx inlet region of a patient. Accordingly, the laryngeal cuff 710 can form a seal at the larynx inlet region such that the lungs can be inflated during artificial ventilation through the central lumen 704, as discussed in more detail below.

In the embodiment of FIG. 9A, the laryngeal cuff 710 is non-inflatable and is sufficiently soft such that it prevents or minimizes trauma to patient's tissues during insertion. The laryngeal cuff 710 can also conform to a curvature of a patient's airway. The non-inflatable laryngeal cuff 710 can be made from a silicone rubber or any other polymeric material which would provide a rubber-like texture for the laryngeal cuff 710.

In the drawing of FIG. 9A, the laryngeal cuff 710 covers the ventral surface 716 of the tongue 703 circumferentially, such that some of the central portion of the internal portion 716 is not covered with the laryngeal cuff 710. In other embodiments, the laryngeal cuff 710 may cover all or nearly all of the ventral surface 716, excluding only the central ramp 714.

In other embodiments, the laryngeal cuff 710 may be made inflatable such that the laryngeal cuff 710 is inflated with air after the device 700 is placed in a patient. In yet further embodiments, the laryngeal cuff 710 is non-inflatable and is made as a shell of silicone rubber or any other polymeric material. The shell is filled with a suitable liquid, gel or gas during manufacturing.

In further embodiments, only portions of the laryngeal cuff are inflatable, while other portions are not inflatable. In some embodiments, the distal portion of the laryngeal cuff 710 may non-inflatable, while lateral portions and/or proximal portion may be inflatable.

The laryngeal cuff 710 absorbs and softens an impact on patient's tissues during the insertion and also improves the seal once the device 700 has been placed.

In the embodiment of FIG. 9A, the laryngeal cuff 710 has a slit 712 which is aligned with the slit 706 of the wall 702 such that when the edges of the wall 702 are pushed apart at the slit 706, the laryngeal cuff 712 can be also pushed apart in order to facilitate the insertion into or removal from the central lumen 704 of an endotracheal tube or any other device. In other embodiments, the laryngeal cuff 710 does not comprise a slit 712. The slit 712 may be sealable in the same as was described in connection with the slit 706. If the laryngeal cuff 710 is inflatable, the slit 712 does not cut through the shell of the laryngeal cuff 710 and, the shell is still intact and it still holds air, gas or liquid.

One of the uses for the central lumen 704 is to deliver an endotracheal tube and facilitate its proper placement. Because of the slits 706 and 712, the endotracheal tube can be easily separated and removed from the central lumen 704 while the oral airway device 700 remains inserted in a patient. In addition, the oral airway device 700 can be separated and removed from a patient after the endotracheal tube has been placed in the patient and while the endotracheal tube remains inserted and in place in the patient without the need of removing the whole assembly from the patient.

If the oral airway device 700 has the slit 706 through the wall 702, one or more accessories can be used in order to establish a closed system through the central lumen 704. Thus, the oral airway device 700 can be used for ventilating a patient through the central lumen 704.

The oral airway device 700 can be used with the ventilator adaptor 507 as shown and described in connection with drawings in FIGS. 1T, 1U and 1V. In alternative, the device 500 can be inserted into the central lumen 704. In further embodiments, an accessory cap 770 can be used in order to establish a closed system for ventilation through the central lumen 704, as shown and described in connection with FIGS. 9N, 9O, 9P and 9Q below.

The oral airway device 700 can be made in different sizes in order to accommodate pediatric patients and adult patients depending on their weight.

Referring to FIG. 9F, it illustrates how the oral airway device 700 of FIG. 9A can be assembled with the endotracheal tube 480 which is inserted into the central lumen 704 through the proximal opening 704B. The suction tube 482 can be positioned in the channel 720 by inserting the suction tube 482 through the proximal opening 720B of the channel 720. The camera 12 with the cable 16 can be inserted into the camera channel 718 through the proximal opening 718B of the camera channel 718. In the device 700, all elements are as was described in connection with FIG. 9A.

Referring to FIG. 9G, it depicts the oral airway device 700 of FIG. 9A assembled with the endotracheal tube 480 hosted in the central lumen 704 with the distal end 480A of the endotracheal tube 480 protruding from the oral airway device 700 distally. The endotracheal tube 480 is projected from the central lumen 704 above the tongue 703 at a predetermined angle. The endotracheal tube is supported at this angle with the central ramp 714.

The suction tube 482 is positioned in the gastric channel 720. The distal end 482A of the suction tube 482 is protruding distally from the oral airway device 700 on the dorsal surface 702C of the oral airway device 700 such that the distal end 482A of the suction tube 482 is positioned externally to the laryngeal cuff 710.

After insertion, the laryngeal cuff 710 is sealing the larynx, while the suction tube 482 can be used to aspirate fluids from the stomach. The assembly further comprises the camera 12 which hosted inside the camera channel 718 and is not visible in the drawing of FIG. 9G, and the cable 16 inserted into the camera channel 718 and a portion of the camera cable 16 remaining outside the camera channel 718. The camera 12 can take images of the distal tip of the assembly and provides continuous visualization during insertion and after the insertion has been completed. The camera can transmit captured information, e.g. images and sounds, remotely.

Referring to FIG. 9H, it depicts the endotracheal tube 480 being separated from the oral airway device 700 through the slit 706 and then through the slit 712. While the endotracheal tube 480 is being removed, the camera 12 and the suction tube 482 may remain inserted, as needed.

Referring to FIG. 9I, it provides a further embodiment of an oral airway device, generally 730. All elements in the oral airway device 730 are the same as described in connection with the oral airway device 700 and as shown in connection with FIGS. 9A-9H, except that the oral airway device 730 comprises an additional element—a dorsal inflatable cuff 734 as described in more detail below.

The dorsal inflatable cuff 734 is positioned on the dorsal surface 703C of the tongue 703, proximally to the tongue tip 703A. The inflatable cuff 734 can be inflated with a means 736. When inflated, the cuff 734 provides an additional seal. It supports the seal created by the laryngeal cuff 710. Because the inflatable cuff 734 can be inflated on demand, the inflatable cuff 734 can be used to fine-tune and adjust the seal and to conform the seal with the anatomy of a patient. Thus, the device 730 can be used in patients in whom the seal with the laryngeal cuff 710 is incomplete.

The oral airway device 730 is equipped with one or more cameras as was discussed in connection with other oral airway devices, including the oral airway device 700. Adjustments in inflation of the inflatable cuff 734 can be made under the continuous visualization from a camera in order to verify the seal. All other elements and their functions as were described in connection with the oral airway device 700.

In brief, the oral airway device 730 comprises the tubal body 702 with a length between the proximal end 702B and the distal end 702A. The tubal body 702 has the slit 706 which opens the wall 702 into the central lumen 704. The laryngeal cuff 710 with the slit 712 is formed and attached to the tongue 703 and the wall 702 as was discussed in connection with FIG. 9A. The ramp 714 is positioned in front of the distal opening 704A from the central lumen 704. The camera channel 718 with the proximal opening 718B and the distal opening 718A is located peripherally to the central lumen 704 in the flank 702L. The other peripheral channel 720 is located in the other flank—702R. The channel 720 opens on the dorsal surface 702C and can be used for guiding a suction tube.

Referring to FIG. 9J, it depicts the oral airway device 730 from the ventral surface (702D). All elements are the same as discussed in connection with FIGS. 9A and 9I. This view shows a position of the distal opening 720A of the channel 720 relative to the tongue 703. The view also shows a position of the inflatable cuff 734 relative to the tongue 703. While in the embodiment of FIG. 9J, the inflatable cuff 734 is shown, in other embodiments, there is no inflatable cuff 734.

Referring to FIG. 9K, it depicts the oral airway device 730 from the dorsal surface (702C). All elements are the same as discussed in connection with FIGS. 9A, 9I and 9J. This view shows a position of the distal opening 720A of the channel 720 relative to the tongue 703. The view also shows a position of the inflatable cuff 734 relative to the laryngeal cuff 710.

Referring to FIG. 9L, it depicts a further embodiment of an oral airway device, generally 740. The oral airway device 740 is a tubal body which is curved and arches anteriorly such that the oral airway device 740 follows the contour of the roof of a patient's mouth during insertion of the oral airway device 740. The curved tubal body of the oral airway device 740 is made by a wall 742 having a length between a distal end 742A and a proximal end 742B.

In the oral airway device 740, the wall 742 is curved as an arch along the distal-proximal 742A-742B axis such that the wall 742 follows the contour of the roof of a patient's mouth. The wall 742, similarly to the wall 700, comprises a dorsal surface 742C (not seen in the drawing of FIG. 9L), a ventral surface 742D which is opposite to dorsal surface 742C and two lateral surfaces connecting the ventral surface 742D and the dorsal surface 742C into a tubal body, the left flank 742L (not seen in the drawing of FIG. 9L) and the right flank (742R). Because of the arch curvature, a length of the wall 742 is longer on the dorsal surface, 742C than on the ventral surface, 742D.

The ventral surface 742D is in contact with the patient's tongue when the device 740 is inserted into an oral cavity. The dorsal surface 742C, is opposite to the ventral surface, 742D.

In the drawing of FIG. 9L, the ventral surface 742D and the right flank 742R are shown. The left flank, 702L is opposite to the right flank 702R and is not visible in the drawing of FIG. 9L.

The wall 742 encircles a central lumen 744. The central lumen 744 is hollow and has a distal opening 744A and a proximal opening 704B, essentially as was described in connection with the central lumen 704 of the oral airway device 700. The proximal opening 744B opens at the proximal end 742B of the wall 742. The distal opening 744A opens near the distal end 742A of the wall 742.

The central lumen 744 may be fully encircled by the wall 742 or the wall 742 may have a slit 746 as shown in FIG. 9L. The slit 746 runs along the distal-proximal 742A-742B axis on the ventral surface 742D. In addition to the slit 746 or instead of the slit 746, some proximal portion of the wall 742 on the ventral surface 742D may be absent as shown in FIG. 9L such that some proximal portion of the central lumen 744 is open on the ventral surface 742D.

A medical device, such as for example an endotracheal tube or any other tool or device suitable for managing patient's airways or a camera, can be placed in the central lumen 744 or removed from the central lumen 744 by opening the wall 742 along the slit 746.

In the embodiment of FIG. 9L, the wall 742 has the slit 746 which runs along the distal-proximal 742A-742B axis on the ventral surface 742D. In other embodiments, the slit 746 may be placed at other surfaces, e.g. one of the flanks or the dorsal surface 742C of the wall 746, so long the slit 746 is located such that a practitioner can access the central lumen 744 through the slit 746 by pushing apart the wall 742 at the slit 746. The function of the slit 746 is the same as was described in connection with the slit 706 in the oral airway device 700.

At the distal end 742A, the wall 742 ends with a tongue 743. The oral airway device 740 also comprises a laryngeal cuff 750 which is positioned in the same way as the laryngeal cuff 710 and has the same function as was described in connection with the laryngeal cuff 710, except the laryngeal cuff 750 is inflatable with a means 754.

In the embodiment of FIG. 9L, the laryngeal cuff 750 is inflatable and it can be inflated with the means 754 which stay externally to the patient after the device 740 is placed in the patient. In other embodiments, the laryngeal cuff 750 can be non-inflatable as was discussed in connection with the laryngeal cuff 710 of the oral airway device 700. The laryngeal cuff 750 comprises a slit 752 which is aligned with the slit 746. The function of the slit 752 is the same as was described in connection with the slit 712 of the cuff 750.

The oral airway device 740 comprises a central ramp 756 which has the same structure and the same functions as the central ramp 714 of the oral airway device 700. In brief, the central ramp 756 lifts a projecting tip of an endotracheal tube or any other device hosted in the central lumen 744 at an angle above the ventral surface 742I, as was described in connection with the central ramp 714.

The oral airway device 740 also comprises a camera channel ramp 764 located distally and in front of the distal opening 758A from the camera channel 758. The structure and functions of the camera channel ramp 764 as was described in connection with the camera channel ramp 724 of the oral airway device 700.

The wall 742 has two peripheral hollow channels, 758 and 760. The channel 758 is a hollow passage in the wall 742. The channel 758 may be used for inserting a camera or some other tools or devices. The structure and the functions of the channel 758 as was described in connection with the camera channel 718 of the oral airway device 700.

The camera channel 758 comprises a proximal opening 758B on the proximal end 742B of the device 740, through which a camera (not shown in the drawing of FIG. 9L) can be inserted. The camera channel 758 ends with a distal opening 758A through which a distal end of the camera when hosted in the channel 758 can project distally with the help of the camera channel ramp 764 and the wall guard 758G. The central lumen 744 and the camera channel 758 are sloped as was discussed in connection with the central lumen 704 and the camera channel 718.

In the embodiment of FIG. 9L, the oral airway device 740 comprises a second peripheral channel 760 which is a hollow channel in the wall 742. The channel 760 has a proximal opening 760B located at the proximal end 742B of the wall 742.

The channel 760 is a hollow passage in the wall 742 which runs along the distal-proximal 742A-742B axis of the wall 742. The channel 760 has a distal opening 760A which opens on the ventral 742I of the tongue 743, proximally to the laryngeal cuff 750.

The channel 760 has a slit 762 which runs along at least a portion of the length of the channel 760 and which opens the channel 760 on the right flank surface 742R in the embodiment of FIG. 9L. In other embodiments, the slit 762 can open to the dorsal surface 702C of the wall 742.

The channel 760 can be used for aspirating fluids by inserting a suction tube 766 in the channel 760. Thus, the channel 760 can perform a function of an esophageal/gastric channel for aspirating stomach contents and in order to prevent vomiting when a distal tip of a suction tube is left in the slit 762 such that the suction tube can reach into the esophagus.

However, because the channel 760 opens at its distal end with the distal opening 760A which is on the ventral surface 742I of the tongue 743, the channel 760 can be used for aspirating blood and/or section in the laryngeal cavity. Furthermore, the channel 760 can be used for delivering tools, including, but not limited to, a bougie, a stylet, forceps, and/or camera to either the esophageal cavity through the slit 762 or to the laryngeal cavity through the distal opening 760A.

Referring to FIG. 9M, this is an enlarged view of the distal portion of the oral airway device 740, showing a distal portion of the channel 760 with a portion of the slit 762 and the distal opening 760A of the channel 760. All reference numbers are as in connection with FIG. 9L.

Referring to FIG. 9N, it depicts an accessory cap, generally 770. As shown in FIG. 9N, the accessory cap 770 can be inserted into the central lumen 704 of the oral airway device 700 or in the central lumen of any other of the oral airway devices with a slit in order to keep the slit 706 closed and to establish a ventilation through the central lumen 704.

The accessory cap 770 is a tubal body made by a wall 772 enclosing a central lumen 774. The wall 772 has a length between a distal end 772A and a proximal end 772B. The central lumen 774 comprises a proximal opening 774B located at the proximal end 772B and a distal opening 774A located at the distal end 772A. The central lumen 774 is a hollow cylindrical channel with the openings 774A and 774B at the ends.

The accessory cap 770 must fit into the central lumen 704 which is curved as was discussed in connection with the curvature of the wall 702 for the oral airway device 700. Accordingly, the accessory cap 770 may be made of a flexible material which assumes any shape, e.g. it would adopt to the curvature of the central lumen 704 once the accessory cap 770 is inserted in the oral airway device 700. In alternative, the accessory cap 770 may be made with the curvature that matches the curvature of the central lumen 704.

The accessory cap 770 may comprise a clip 776 with a distal end 776A and a proximal end 776B. The clip 776 is attached at the proximal end 776B to the wall 772 externally. FIG. 9O is a cross-sectional view of the wall 772 showing the clip 776 attached to the wall 772. FIG. 9P is a side-view at the clip 776 and also showing a portion of the wall 772 to which the proximal end 776B of clip 776 is attached.

As shown in FIG. 9Q, the accessory cap 770 can be placed into the central lumen 707 of the oral airway device 700. The width of the clip 776 and its positioning on the wall 772 are designed such that when the accessory cap 770 is placed into the central lumen 704, the clip 776 fits over the recess 708, and holds the edges of the wall 702 together at the slit 706. Accordingly, the edges of the wall 702 do not come apart at the slit 706 because the clip 776 holds them together. A closed ventilation system can be now established through the central lumen 707, and the oral airway device 700 can be used for ventilation.

The oral airway device 700 may further comprise two holders 778 positioned one on each side of the slit 706 near the recess 708. These holders 778 can be used to further hold the clip 776 in place on the wall 702 and prevent the slit 706 from coming apart during ventilation through the central lumen 704.

FIG. 9R depicts an adaptor 800 which is a hollow tube made by a wall 802 with a longitudinal slit 804 for holding a camera 12 with cable 16. The adaptor 800 is made of a sufficiently rigid polymeric material such that if the camera 12 with cable 16 is inserted in into the adaptor 800, the adaptor 800 holds the camera 12 with cable 16 in a predetermined shape and provides a backbone to otherwise flexible cable 16 if the cable 16 cannot keep a fixed shape, as shown in FIG. 9S. The camera 12 can be then positioned near a distal end 802A of the wall 802. The adaptor 800 can be used for hosting other tools, e.g. bougie or stylet.

FIG. 9T shows how the assembly of FIG. 9S can be placed into the central lumen 704 of the oral airway device 700. In FIG. 9T, all elements are labeled as was discussed in connection with other drawings, including 9A, 9R and 9S. FIGS. 9U and 9V depict combining the assembly of FIG. 9S with the oral airway device 700 (FIG. 9U) and further with the endotracheal tube 480 (FIG. 9V).

Figure 9X:
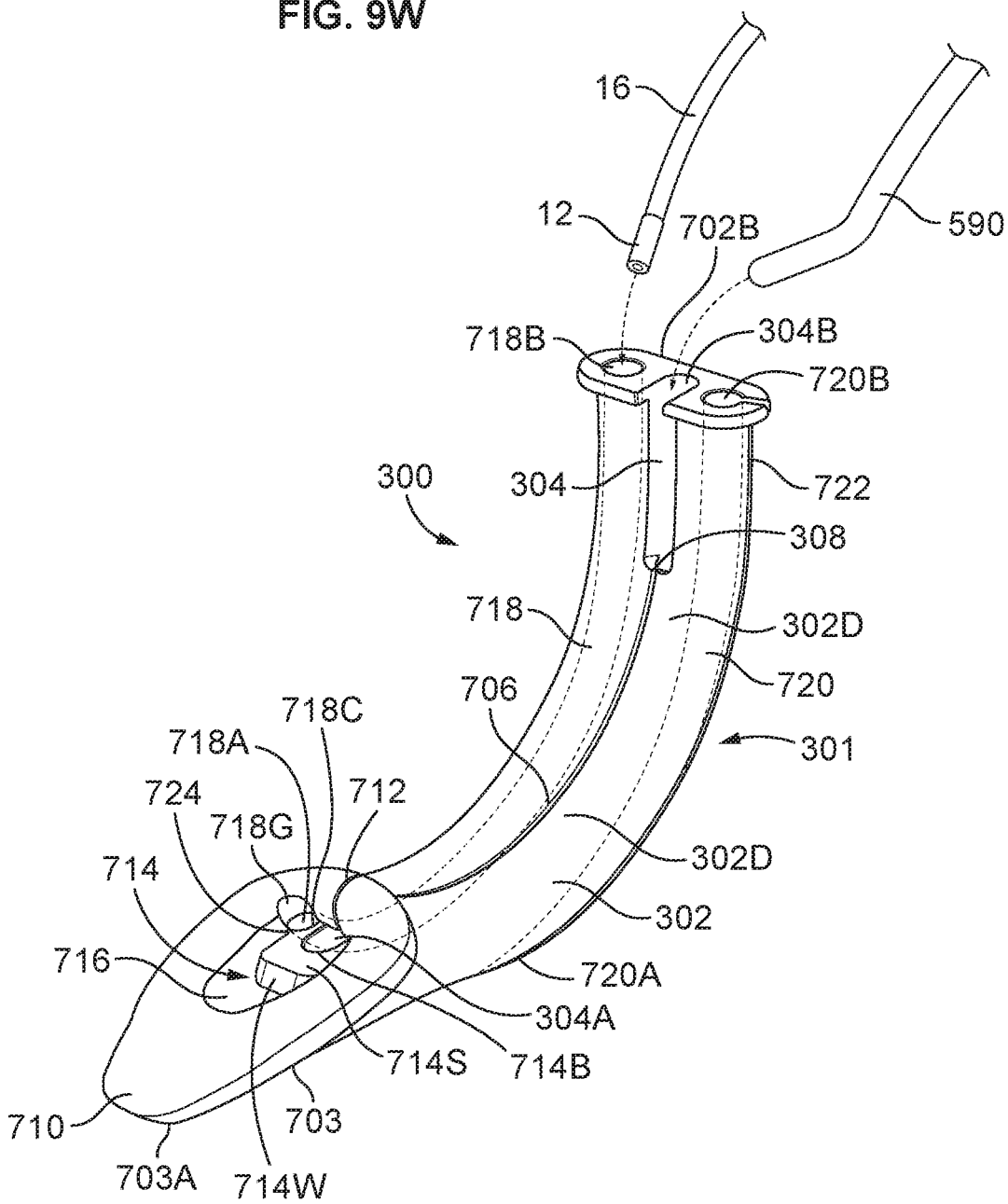
FIG. 9X depicts an oral airway device compatible with a bag mask.

Referring to FIG. 9X, it depicts another embodiment for an oral airway device of this disclosure, generally 300.

The oral airway device 300 has the same elements with the same structures and functions as were described in connection with the oral airway device 700, except the oral airway device 300 has a narrow central lumen 304 which can accommodate a bougie, e.g. the bogue 590, but the central lumen 304 does not carry an endotracheal tube because a diameter of the central lumen 304 is smaller than a diameter of an endotracheal tube. As shown in the drawing of FIG. 9X, the bogue 590 can be inserted into the central lumen 304 through a proximal opening 304B. The bougie 590 can project distally from the central lumen 304 through a distal opening 304A of the central lumen 304.

Since the central lumen 304 is narrow, the tubal body 301 with its wall 302 of the device 300 has a smaller diameter than the wall 702 of the oral airway device 700. Accordingly, the oral airway device 300 is much easier to insert and remove and has a lesser burden on the patient's tissues. The oral airway device 300 can be used to ventilate a patient through a bag-mask. The wall 302 comprises the slit 706 which is the same as was described in connection with the wall 702. Just like the oral airway device 700, the oral airway device 300 is shown from the ventral surface 302D of the wall 302.

Figures 10A, 10B:
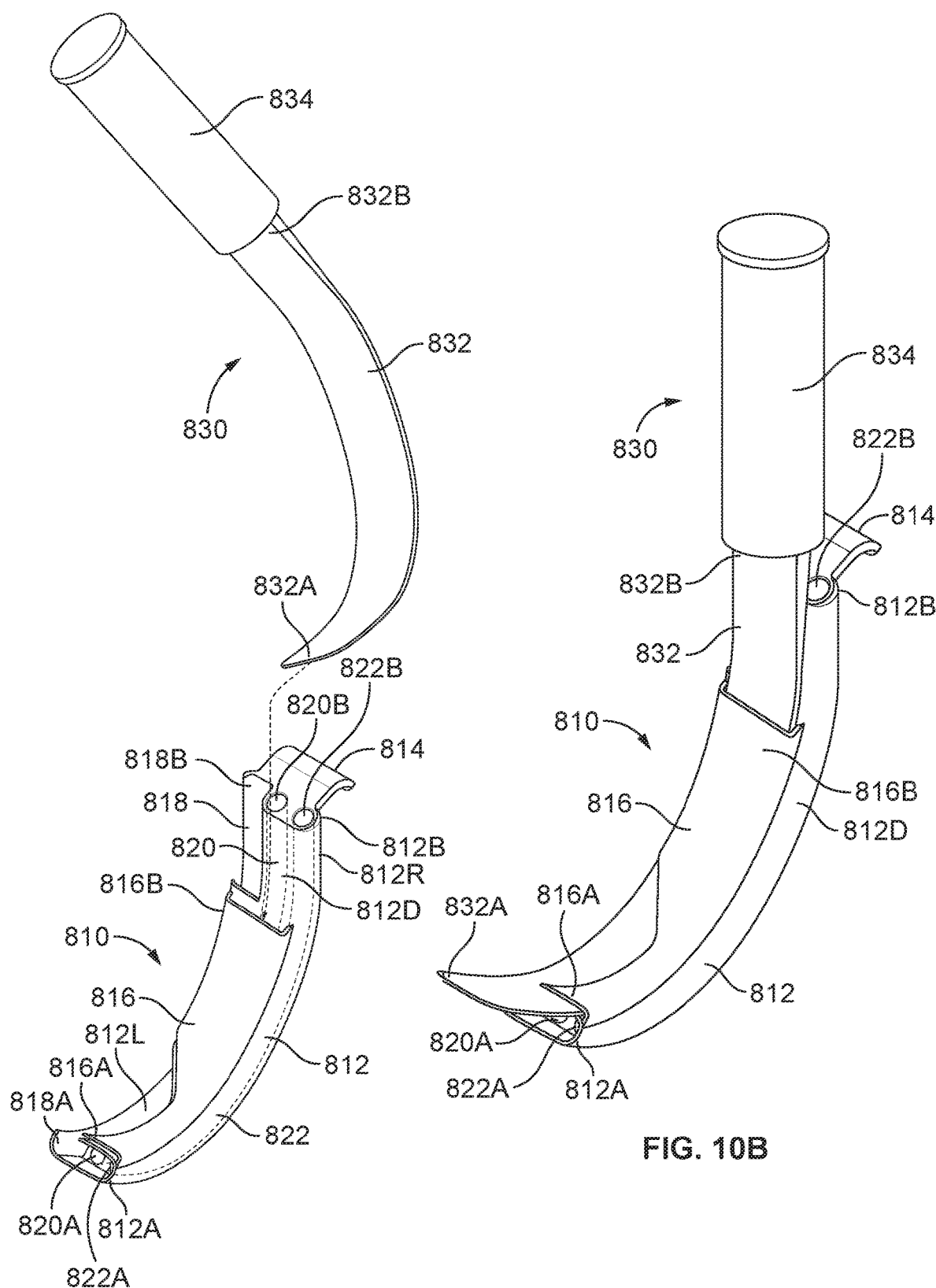
FIG. 10A depicts an oral airway device with peripheral channels and compatible with a laryngoscope.
FIG. 10B depicts the oral airway device of FIG. 10A being assembled with a laryngoscope.

Referring to FIG. 10A, it depicts an oral airway device, generally 810. The oral airway device 810 does not comprise an endotracheal lumen. Just like the oral airway device 600, the oral airway device 810 is a tubal body curved anteriorly. The tubal body of the oral airway device 810 is created by a wall 812 with a length between a distal end 812A and a proximal end 812B.

The wall 812 is curved anteriorly along the distal-proximal axis 812A-812B and follows the contour of the roof of a patient's mouth during insertion of the device 810 into the patient. The wall 812 has a dorsal surface, 812C, and a ventral surface, 812D. In the drawing of FIG. 10A, the dorsal surface 812C is not shown. There are two flanks (lateral surfaces) 812L and 812R located between the dorsal surface 812C and ventral surface 812D. Looking at the ventral surface 812D, the flank 812L is the left flank between the ventral surface 812D and the dorsal surface 812C. The flank 812R is opposite to the flank 812L. The flank 812R is the right flank between the ventral surface 812D and the dorsal surface 812C.

In some embodiments, the oral airway device 812 may comprise a handle 814 attached to the wall 812 on the dorsal surface 812C to the proximal end 812B. The handle 812 aids a practitioner in manipulating the device 810 during insertion and removal. The handle 814 may be attached removably such that the handle 814 can be separated from the wall 812 after the oral airway device 812 has been placed. In some embodiments, the oral airway device 810 does not comprise a handle.

The wall 812 creates an arch which follows the contour of the rood of a patient's mouth such that the ventral surface 812D is in contact with a patient's tongue when the device 810 is inserted in the patient. The oral airway device 810 has several channels. In the drawing of FIG. 10A, three channels are shown, 818, 820 and 822. In other embodiments, one or more of additional channels may be added or one or more of the channels 818, 820 and/or 822 may be missing.

The channels 818, 820 and 822 are hollow passages in the wall 812 along the distal-proximal 812A-812B axis.

Each of the channels, 818, 820 and 822, opens with a proximal opening 818B, 820B, and 822B, respectively, at the proximal end 812B of the wall 812. Each of the channels, 818, 820 and 822, opens with a distal opening 818A, 820A, and 822A, respectively, at the distal end 812A of the wall 812. In the embodiment of FIG. 10A, the oral airway device 810 comprises three channels. In other embodiments, this oral airway device 810 may comprise more than three, for example, 4 or 5, or fewer than 3 channels, for example, 2 or 1.

The channel 818 is a peripheral channel as it located in the flank 812L. It is a semi-lumen or a groove. The channel 818 is not covered by the wall 812 on at least portion of the ventral surface 812D.

The channel 818 creates a groove into which a camera, a bougie, a tool or a tube can be placed. Because of its groove-like shape, the channel 818 keeps the camera, tool or tube in place and prevents it from jamming or separating from the oral airway device 810.

However, as the channel 818 is open along the distal-proximal axis 812A-812B, it is easy to manipulate and/or remove the camera, the bougie or tool or tube from the channel 818 while the oral airway device 812 still remains inserted and in place in a patient.

In the drawing of FIG. 10A, the channel 818 opens externally to the ventral surface 812D. In other embodiments, the channel 818 can open into the left flank 812L of the wall 818. In other embodiments, the channel 818 may be a lumen which is covered with wall on all or substantially all surfaces.

The channel 820 is a hollow passage in the wall 812 of oral airway device 810. The channel 820 can be used for hosting a camera by placing the camera through the proximal opening 820B of the channel 820. The channel 820 is located centrally in the device 812.

The channel 822 is located peripherally to the channel 820. The channel 822 is located in the right flank 812R. In the drawing of FIG. 10A, the channel 822 is a lumen (hollow passage) which runs along the distal-proximal axis 802A-802B. In other embodiments, the channel 822 may be a semi-lumen (groove) which opens externally from the wall 812 on one of the wall surfaces: 812D, 812R or 812C.

The channel 822 creates a hollow passage into which a camera, tool or a tube can be placed. Any of the three channels, 818, 820 and/or 822, may be used for inserting a camera or a tool including for example, forceps, a suction tube, a stethoscope, a temperature probe, a bougie or a stylet and/or a device which monitors breathing and heart sounds.

The oral airway device 810 is compatible with a laryngoscope, generally 830, which comprises a blade 832 attached to a handle 834. The oral airway device 810 comprises a holder (sheath) 816 attached to the ventral surface 812D. The curvature of the holder 816 matches that of the blade 832 such that the blade 832 can be inserted into the holder 816.

As shown in FIG. 10B, the laryngoscope 830 can be assembled with oral airway device 810 by inserting the blade 832 into the holder 816. The holder 816 serves as a sheath and gloves over at least a portion of the blade 832, while the distal end 832A of the blade 832 protrudes distally from the holder 816. The proximal end 832B of the blade 832 is attached to the handle 834. A practitioner can operate the laryngoscope 830 by manipulating the handle 834 which remains outside the patient's oral cavity. Because the laryngoscope 830 is combined with the oral airway device 810, the laryngoscope 830 can be operated under the continuous visualization by one or more cameras inserted into one of the channels 818, 820 and/or 822.

Referring to FIGS. 10C and 10D, they depict how the oral airway device 810 can be combined with the camera 12 with cable 16 which is inserted into the channel 820 through the proximal opening 820B and the bougie 590 which can be inserted into the channel 818.

Figure 11A:
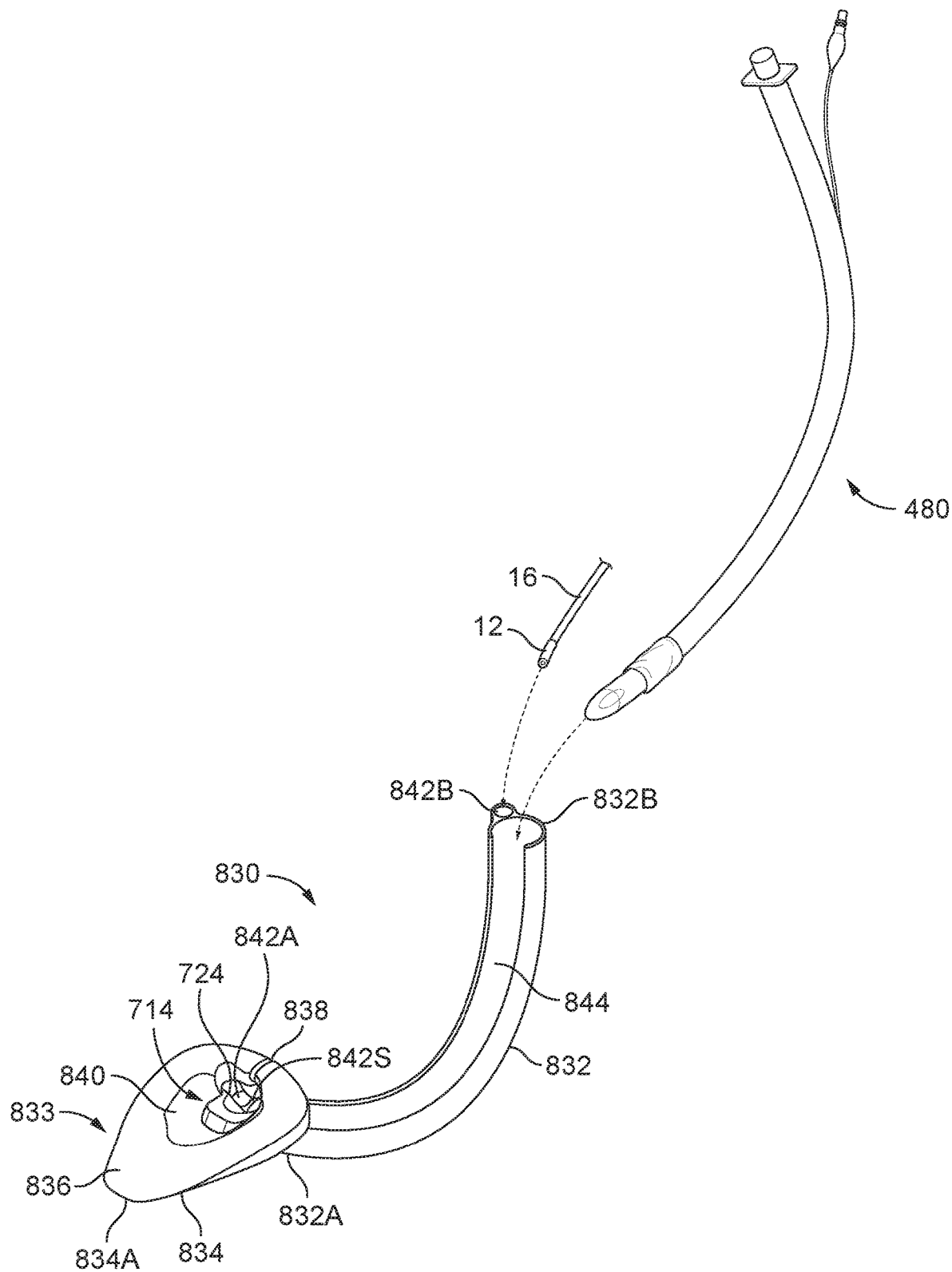
FIG. 11A depicts a laryngeal mask with a handle and a camera channel.

Referring to FIG. 11A, it depicts another oral airway device, generally 830, according to this disclosure. The device 830 comprises a laryngeal mask 833 attached to a handle 832. The handle 832 has a length between a distal end 832A and a proximal end 832B. The handle 832 is curved anteriorly such that the oral airway device 830 follows the contour of the roof of a patient's mouth during insertion of the oral airway device 830. The handle 832 is not a tubal body, instead it is a slide-like groove which forms a semi-lumen 844 into which the endotracheal tube 480, or any other tube or a device or a tool, can be loaded. At its distal end 832A, the handle 832 ends with a tongue 834 which has a ventral surface 840. A tip 834A of the tongue 834 is tapered.

A laryngeal cuff 836 is formed and attached around the perimeter of the ventral surface 840 of the tongue 834. The structure and the attachment of the laryngeal cuff 836 is the same as was described in connection with the laryngeal cuff 710, e.g. it can be non-inflatable, inflatable or some portions of the laryngeal cuff 836 may be inflatable, while other portions of the laryngeal cuff 836 are not inflatable. The laryngeal cuff 836 is shaped such that it corresponds to a contour of the larynx inlet region of a patient. Accordingly, the laryngeal cuff 836 can form a seal at the larynx inlet region. In some embodiments, the laryngeal cuff 836 may cover less than all of the perimeter of the tongue 834. In these embodiments, only a distal portion of the tongue 834 may be covered with the laryngeal cuff 836. In these embodiments, the laryngeal cuff 836 only partially occludes the larynx inlet. The laryngeal cuff 836 attached to the tongue 834 is referred to as the laryngeal mask 833.

The laryngeal cuff 836 has slit 838 which is aligned with the semi-lumen 844, such that after the endotracheal tube 480 is placed through the vocal cords, the oral airway device 830 can be separated from the endotracheal tube 480 through the slit 838 and removed, while the endotracheal tube 480 remains properly placed in a patient.

The central ramp 714 is positioned on the ventral surface 840 of the tongue 834. The position, the structure and the functions of the central ramp 714 are the same as was described in connection with the oral airway device 700. Because the handle 832 is curved at a slope from the tongue 834, the endotracheal tube 480 or any other device or tube or tool positioned in the semi-lumen 844 is projected at an angle from the ventral surface 840. The angle may be the same as was described in connection with the central lumen 704 of the oral airway device 700. The central ramp 714 supports the projected endotracheal tube 480 above the ventral surface 840.

The oral airway device 830 comprises a camera channel 842 which is a hollow passage that runs along the length of the handle 832. The camera channel 842 can be a hollow passage which is carved out in the handle 832 or the camera channel can be a tube which is attached, and in some embodiments, slidably attached to the handle 832. The camera channel 842 has a proximal opening 842B, which is an inlet into the camera channel 842. The proximal opening 842B is located at the proximal end 832B of the handle 832. The camera channel 842 has a distal opening 842A, which is an outlet from the camera channel 842. The distal end 842A opens onto the ventral surface 840. The camera channel 842 is sloped in the same way as was discussed in connection with the camera channel 718. Accordingly, the camera channel 842 projects a camera (or a tool) positioned in the camera channel 842 at a predetermined angle, as was discussed in connection with the camera channel 718. The ramp 724 is positioned in front of distal opening 842A. The ramp 724 has the same structure and function as was described in connection with the oral airway device 700. A ledge 842S has the same structure and function as was described in connection with the camera channel 718. The camera 12 with cable 16, which can be any camera as was described in connection with other embodiments, can be inserted into the camera channel 842 and provide continuous visualization of the endotracheal tube 480 and the patient's tissues.

Figure 11B:
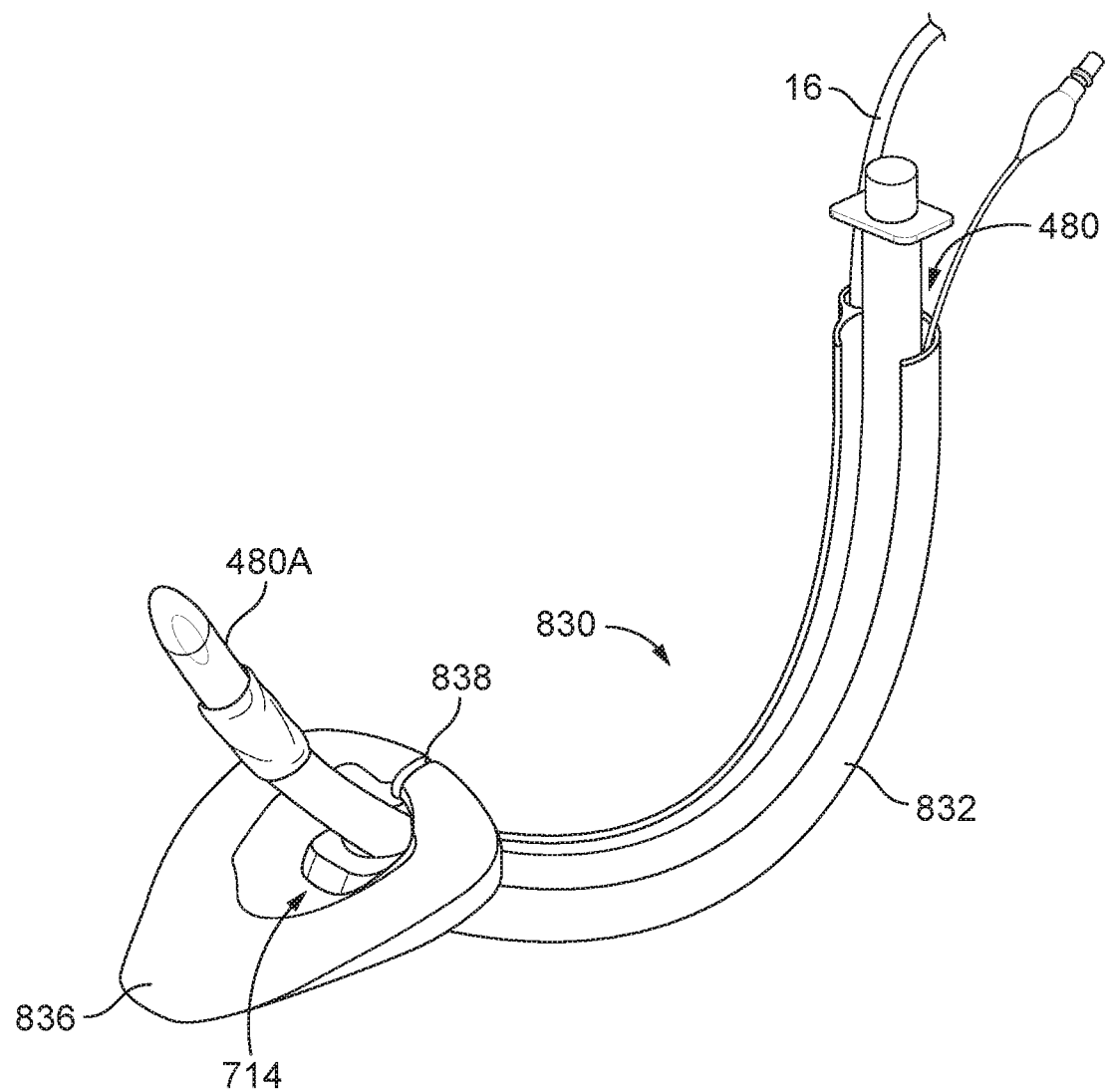
FIG. 11B depicts the laryngeal mask of FIG. 11A hosting an endotracheal tube.

Referring to FIG. 11B, it depicts the oral airway device 830 hosting the endotracheal tube 480 and the camera 12 (not shown). All elements as were discussed in connection with FIG. 9A.

Figure 12A:
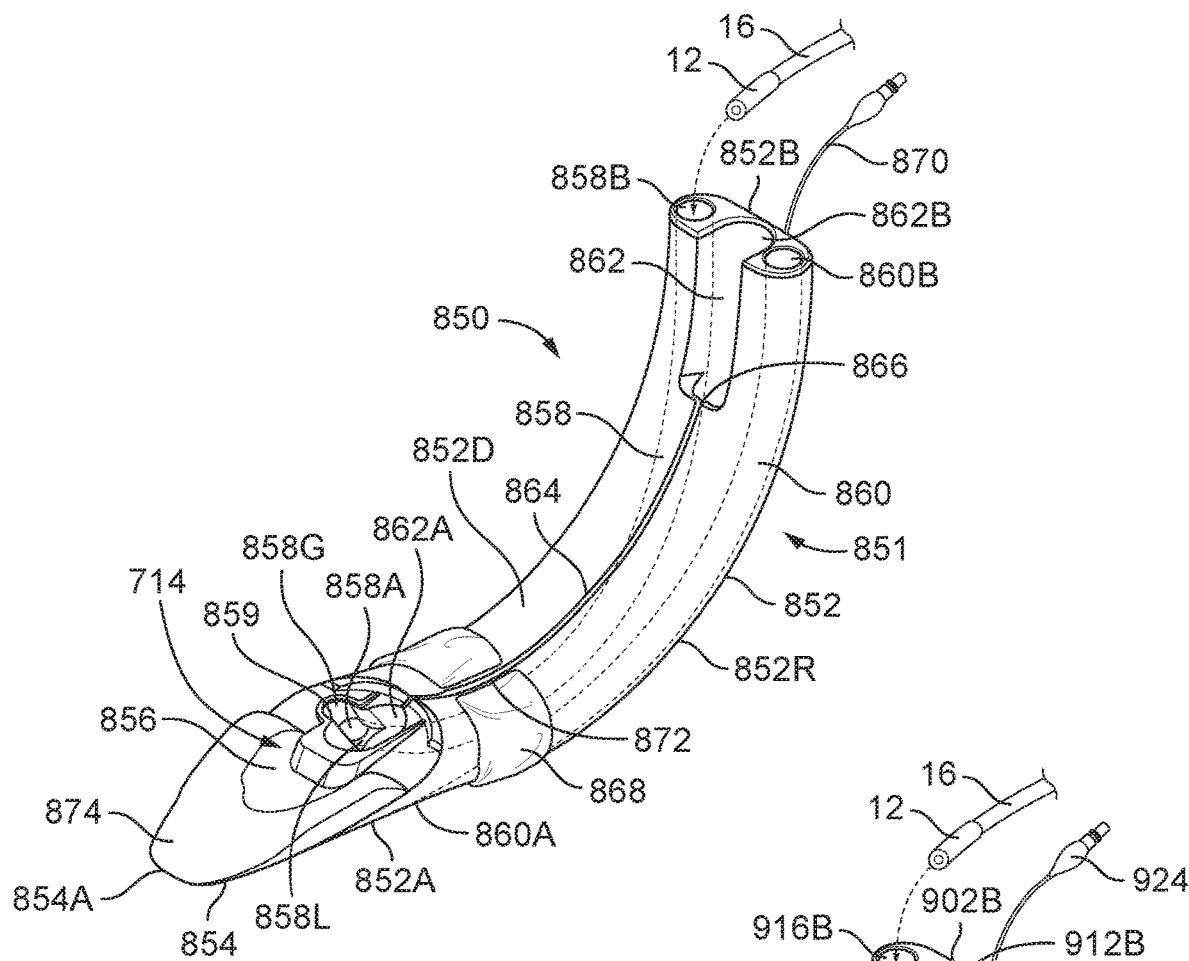
FIG. 12A depicts another embodiment of an oral airway device according to this disclosure.

Referring to FIG. 12A, it depicts a further embodiment of an oral airway device according to this disclosure, generally 850. Unlike the oral airway device 700 or the oral airway device 830, the oral airway device 850 does not completely occlude the larynx inlet.

The oral airway device 850 comprises a tubal body 851, the structure and function of which are the same as were described in connection with the tubal body 701. Specifically, the tubal body 851 is made by the wall 852, the structure and function of which are the same as were described in connection with the wall 702. The wall 852 has a length between a distal end 852A and a proximal end 852B. The wall 852 is curved as was described in connection with the wall 702.

The wall 852 has the same surfaces as were described in connection with the wall 700: a dorsal surface (not seen in FIG. 12A), a ventral surface 852D and two flanks 852R and 852L (not seen in FIG. 12A). The wall 852 hosts a central lumen 862 with a proximal opening 852B and a distal opening 852A. The structure and the functions of the central lumen 862 are the same as were described in connection with the central lumen 704 of the oral airway device 700.

The wall 852 also hosts a camera channel 852 which is a hollow passage in the wall 852. The camera channel 852 has a proximal opening 852B and a distal opening 852A. The positioning of the camera channel 852 in the wall 852, the structure and functions of the camera channel 852 are the same, as were described in connection with the camera channel 718.

The wall 852 also hosts a gastric channel 860 which is a hollow passage with a proximal opening 860B and a distal opening 860A. The positioning of the gastric channel 860 in the wall 852, the structure and functions of the gastric channel 860 are the same, as were described in connection with the gastric channel 720.

Just like the wall 702, the wall 852 comprises a slit 864 which is located on the ventral surface 852D of the wall 852. The slit 864 has the same structure and functions as were described in connection with the slit 706 of the oral airway device 700. The wall 852 also has a recess 866 which is the same as the recess 708 described in connection with the wall 702.

At its distal end 852A, the wall 852 ends with a tongue 854. A distal tip 854A of the tongue 854 is tapered. On the ventral surface 856 of the tongue 854, one finds the central ramp 714, the structure and functions of which are the same as were described in connection with the oral airway device 700. An endotracheal tube or any other device or tool hosted in the central lumen 862 is projected at a predetermined angle from the central lumen 862, as was described in connection with the central lumen 704. The central ramp 714 supports the projected endotracheal tube, as was described in connection with the oral airway device 700. The wall 852 is made of a thermoplastic material and is curved as was described in connection with the wall 702. Accordingly, the central lumen 862 is sloped from the tongue 854, as was described in connection with the central lumen 704.

The camera channel 858 can host the camera 12 with the cable 16 in the same way was described in connection with the camera channel 718. A camera hosted in the camera channel 858 is projected at a predetermined angle from the distal end 858A of the camera channel 858, as was described in connection with the camera channel 718. The projecting camera is aligned with an endotracheal tube with the help of a guard 758G, a camera channel ramp 859 and a ledge 858L, as was described in connection with elements 718G, 724 and 718L.

There is a non-inflatable partial laryngeal cuff 874 formed around at least some distal portion of the perimeter of the ventral surface 856 of the tongue 854.

The partial laryngeal cuff 874 is different from the laryngeal cuff 710 because the partial laryngeal cuff 874 covers only a portion of the larynx inlet. Thus, the partial laryngeal cuff 874 does not occlude the larynx completely. In some embodiments, the partial laryngeal cuff 874 covers only about 70 to 90% of the larynx inlet.

The oral airway device 850 comprises an inflatable peripheral cuff 868 which can be inflated with a means 870. While in the embodiment of FIG. 12A, the peripheral cuff 868 is inflatable, the peripheral cuff 868 is not inflatable in other embodiments.

The peripheral cuff 868 wraps around the tubal body 851 and is attached to the wall 852. The peripheral cuff 868 is located proximally to the distal end 852A of the wall 852. The position of peripheral cuff 868 on the wall 852 is such that the peripheral cuff 852 can seal the area around the oral airway device 850. Accordingly, the oral airway device 850 can be used to ventilate a patient with an endotracheal tube or through the central lumen 862. The peripheral cuff 868 has a slit 872 which is aligned over the slit 864. Accordingly, an endotracheal tube can be separated from the oral airway device 850 through the slits 872 and 864. Thus, the endotracheal tube remains in place, while the oral airway device 850 can be removed from the patient.

It should be noted that any of other oral airway devices provided in this disclosure, including the devices 700, 730, 740 and/or 300, may also comprise the peripheral cuff 868.

Figure 12B:
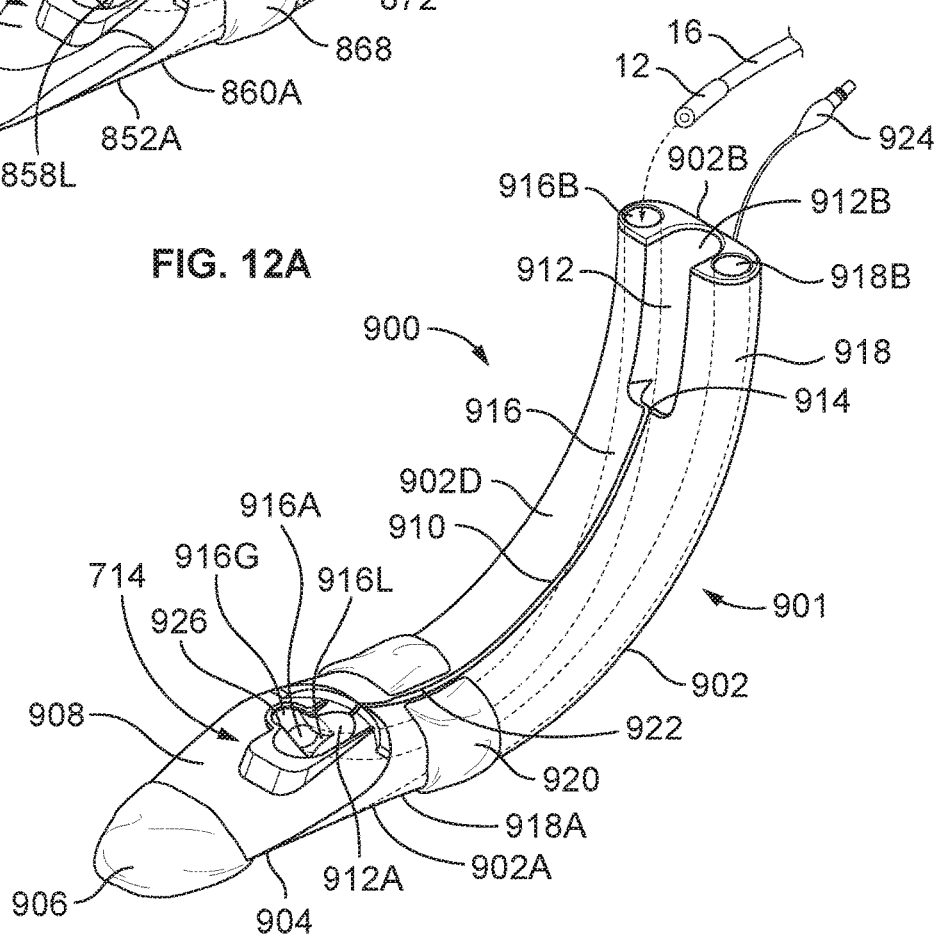
FIG. 12B depicts another embodiment of an oral airway device according to this disclosure.

Referring to FIG. 12B, it depicts a further embodiment of an oral airway device according to this disclosure, generally 900. Unlike the oral airway device 700 or the oral airway device 830, the oral airway device 900 does not comprise a laryngeal cuff and it does not occlude the larynx inlet. Instead, the oral airway device 900 comprises an upper esophagus cuff 906, as described in more detail below.

Unlike the oral airway device 850, the oral airway device 900 does not comprise the cuff 874. Instead, the oral airway device 900 comprises the upper esophagus cuff 906. All other elements of the oral airway device 900 are the same as were described in connection with the oral airway device 850.

The oral airway device 900 comprises a tubal body 901, the structure and function of which are the same as were described in connection with the tubal body 701. Specifically, the tubal body 901 is made by the wall 902, the structure and function of which are the same as were described in connection with the wall 702. The wall 902 has a length between a distal end 902A and a proximal end 902B. The wall 902 is curved as was described in connection with the wall 702.

The wall 902 has the same surfaces as were described in connection with the wall 700: a dorsal surface (not seen in FIG. 12B), a ventral surface 902D and two flanks 902R and 902L (not seen in FIG. 12B). The wall 902 hosts a central lumen 912 with a proximal opening 912B and a distal opening 912A. The structure and the functions of the central lumen 912 are the same as were described in connection with the central lumen 704 of the oral airway device 700.

The wall 902 also hosts a camera channel 916 which is a hollow passage in the wall 902. The camera channel 916 has a proximal opening 916B and a distal opening 916A. The positioning of the camera channel 916 in the wall 902, the structure and functions of the camera channel 916 are the same, as were described in connection with the camera channel 718.

The wall 902 also hosts a gastric channel 918 which is a hollow passage with a proximal opening 918B and a distal opening 918A. The positioning of the gastric channel 918 in the wall 902, the structure and functions of the gastric channel 918 are the same, as were described in connection with the gastric channel 720.

Just like the wall 702, the wall 902 comprises a slit 910 which is located on the ventral surface 902D of the wall 902. The slit 910 has the same structure and functions as were described in connection with the slit 706 of the oral airway device 700. The wall 902 has a recess 914 which is the same as was described as recess 908 in connection with the wall 702 of the device 700.

At its distal end 902A, the wall 902 ends with a tongue 904. A distal tip 904A of the tongue 904 is tapered. On the ventral surface 908 of the tongue 904, one finds the central ramp 714, the structure and functions of which are the same as were described in connection with the oral airway device 700. An endotracheal tube or any other device or tool hosted in the central lumen 912 is projected at a predetermined angle from the central lumen 912, as was described in connection with the central lumen 704. The central ramp 714 supports the projected endotracheal tube, as was described in connection with the oral airway device 700. The wall 902 is made of a thermoplastic material and is curved as was described in connection with the wall 702. Accordingly, the central lumen 912 is sloped from the tongue 904, as was described in connection with the central lumen 912.

The camera channel 916 can host the camera 12 with the cable 16 in the same way was described in connection with the camera channel 718. A camera hosted in the camera channel 916 is projected at a predetermined angle from the distal end 916A of the camera channel 916, as was described in connection with the camera channel 916. The projecting camera is aligned with an endotracheal tube with the help of a guard 916G, a camera channel ramp 926 and a ledge 916L, as was described in connection with elements 718G, 724 and 718L.

There is a no laryngeal cuff formed around at least some distal portion of the perimeter of the ventral surface 908 of the tongue 904. Accordingly, the oral airway device 900 does not occlude the larynx inlet. However, the distal tip of the tongue 904 is covered with an upper esophagus cuff 906 which can be used for blocking esophagus. The upper esophagus cuff 906 is non-inflatable in the drawing of FIG. 12B. In other embodiments, the upper esophagus cuff 906 can be inflatable.

The oral airway device 900 comprises an inflatable peripheral cuff 920 which can be inflated with a means 924. While in the embodiment of FIG. 12B, the peripheral cuff 920 is inflatable, the peripheral cuff 920 is not inflatable in other embodiments.

The peripheral cuff 920 wraps around the tubal body 901 and is attached to the wall 902. The peripheral cuff 920 is located proximally to the distal end 902A of the wall 902. The position of peripheral cuff 920 on the wall 902 is such that the peripheral cuff 920 can seal the area around the oral airway device 900. Accordingly, the oral airway device 900 can be used to ventilate a patient with an endotracheal tube or through the central lumen 912. The peripheral cuff 920 has a slit 922 which is aligned over the slit 910. Accordingly, an endotracheal tube can be separated from the oral airway device 900 through the slits 922 and 910. Thus, the endotracheal tube remains in place, while the oral airway device 900 can be removed from the patient.

In further aspects, this disclosure provides kits or systems for managing patient's airways. The kits/systems may comprise at least one of the devices described in this disclosure and further comprising additional tools and/or materials. These kits may include the oral airway device 460, 510, 520, 530, 540, 560, 580, 600, 700, 730, 740, 810, 300, 830, 850 and/or 900 together with any of the following: the adaptor 500 and or the adaptor 770, the ventilator adaptor 507, the camera 12, the plug 546, the bougie 590, the adaptor 620, the adaptor 640, the adaptor 660, the adaptor 680, or any combination thereof. The kit/system may further comprise other tools and/or a manual. The kit/system may include any of the oral airway devices in several different sizes, including the oral airway devices adopted for pediatric patients. Any of the devices described in this disclosure may be made in different sizes in order to accommodate pediatric patients and adult patients of different body weights.

In further aspects, this disclosure provides methods for managing patient airways, including ventilating and monitoring a patient. In these methods, at least one of the oral airway devices 460, 510, 520, 530, 540, 560, 580, 600, 700, 730, 740, and 810 is combined with at least a camera and preferably at least with a camera and a tool, such as for example a stylet or bougie, which can assist in placement of the oral airway device 460, 510, 520, 530, 540, 560, 580, and/or 600 into a patient. The oral airway devices may be also combined with a suction tube and/or a monitor of patient's heart tones and sounds. Any of these assemblies are then inserted into the patient's oral cavity and the oral airway device is then positioned in the patient's pharynx. If needed, a closed system can be established by using any of the cuffs 476, 494, 542, 710 and/or the adaptors 500, 507, 770 and/or plugs 546. The assembly is then connected to a ventilator and the patient is ventilated through the ETT lumen 468 or one of the channels 584, 586 and/or 588.

If a patient must be intubated, an endotracheal tube can be loaded into the ETT lumen of the oral airway device 460, 510, 520, 530, 540, 560, 700, 730 or 740. The assembly can then deliver the endotracheal tube to the patient's trachea and ensure its proper placement.

The insertion of the oral airway device 460, 510, 520, 530, 540, 560, 580, 600, 700, 730, 740 and/or 810 into the patient's oral cavity then can be conducted by one single practitioner under continuous visualization from one or more cameras which ensures accurate and rapid placement of the device into the patient's pharynx. If the oral airway device 460, 510, 520, 530, 540, 560, 700, 730 or 740 carries an endotracheal tube, the oral airway devices can be easily separated and removed through the slit in the endotracheal lumen from the endotracheal tube while the endotracheal tube still remains inserted and in place in the patient. These methods avoid repetitive intubation/extubation.

Furthermore, because the oral airway devices 460, 510, 520, 530, 540, 560, 700, 730 and 740 comprise an endotracheal tube lumen which is curved anteriorly at a predetermined angle and also because the devices comprise a ramp, the devices project and hold the endotracheal tube an angle optimal for insertion through the vocal cords. This improves the efficiency of intubation, shorts the time needed for intubation and minimizes the risk of trauma.

After the intubation has been completed, the intubated patient can be monitored continuously with the camera(s) and also for heart tones and sounds and/or temperature as needed.

The present devices and methods can be used for intubating patients who are difficult to intubate and also for patients with damaged airways. The present devices and methods are suitable for monitoring a patient for an adverse reaction such as for example, vomiting and/or obstruction.

While certain medical devices are described above, a person of skill would appreciate that this invention also includes embodiments with various obvious modifications as would be easily apparent to a person of skill.

What is claimed is:

1. An oral airway device having a tubal body curved anteriorly and made by a wall wherein the wall has a length between a distal end and a proximal end, the tubal body ends with a tongue at the distal end,
   wherein the wall has a dorsal surface and a ventral surface and the tongue has a dorsal surface and a ventral surface,
   the wall encircles a central lumen, wherein the central lumen is a ventilation lumen, and wherein the central lumen has a proximal opening located at the proximal end of the wall and a distal opening located at the distal end of the wall, the distal opening of the central lumen opens the central lumen onto the ventral surface of the tongue, wherein the central lumen is sloped at a first predetermined angle from the dorsal surface of the tongue and the central lumen projects an endotracheal tube or a tool above the ventral surface of the tongue and toward the trachea when the endotracheal tube or the tool is hosted in the central lumen and the oral airway device has been placed in a patient;
   the wall has a slit along the distal-proximal axis on the ventral surface of the wall, the slit opens into the central lumen;
   wherein the oral airway device further comprises a central ramp located on the ventral surface of the tongue in front of the distal opening of the central lumen;
   wherein the wall further comprises a camera channel which is a hollow passage in the wall, the camera channel runs along the distal/proximal axis, the camera channel has a distal opening which is an outlet from the wall and a proximal opening which is an inlet in the wall, the distal opening of the camera channel opens the camera channel onto the ventral surface of the tongue,
   wherein the camera channel is sloped at a second predetermined angle from the dorsal surface of the tongue and the camera channel projects a camera above the ventral surface of the tongue and toward the trachea when the camera is hosted in the camera channel and the oral airway device has been placed in the patient;
   wherein the oral airway device further comprises a gastric channel which is a hollow channel in the wall, the gastric channel having a proximal opening located at the proximal end of the wall and a distal opening which opens on the dorsal surface of the wall and wherein the distal opening of the gastric channel is facing toward the esophagus when the oral airway device has been placed in the patient; and wherein
   the oral airway device further comprises a laryngeal cuff formed around the perimeter of the ventral surface of the tongue.

2. The oral airway device of claim 1, wherein the laryngeal cuff of the oral airway device is formed only around the distal portion of the perimeter of the ventral surface of the tongue and the laryngeal cuff does not occlude the larynx inlet completely or the laryngeal cuff is absent and is replaced with an upper esophagus cuff, and wherein the oral airway device further comprises a peripheral cuff with a slit, the peripheral cuff being wrapped around the wall proximally to the distal end of the wall, the slit of the peripheral cuff being aligned over the slit of the wall.

3. The oral airway device of claim 1, wherein the first predetermined angle is greater than the second predetermined angle.

4. The oral airway device of claim 1, wherein the laryngeal cuff is non-inflatable, lateral portions of the laryngeal cuff are inflatable, or the laryngeal cuff is inflatable.

5. The oral airway device of claim 1, wherein the laryngeal cuff comprises a slit which is aligned with the slit of the wall.

6. The oral airway device of claim 1, wherein a diameter of the central lumen is smaller than a diameter of an endotracheal tube, and the central lumen does not carry the endotracheal tube, and wherein the oral airway device can be used with a bag-mask to ventilate a patient.

7. The oral airway device of claim 1, wherein the oral airway device further comprises at least one camera, wherein the camera is insertable into the camera channel, the camera is built-in the wall, the camera is sealed to the wall, or the camera is connected slidably along the wall.

8. The oral airway device of claim 7, wherein the at least one camera transmits images, heart tones, temperature measurements and/or breath sounds wirelessly to one or more monitors being positioned at one or more remote locations.

9. The oral airway device of claim 1, wherein the oral airway device further comprises one or more of the following: a plug insertable and removable from a proximal opening the camera channel; and an accessory cap which is a hollow tube with a clip attached to the wall, the accessory cap insertable into and removable from the central lumen and the clip capable of holding edges of the wall together at the slit.

10. The oral airway device of claim 1, wherein the oral airway device comprises one or more cameras, each of the cameras:
   being insertable into the camera channel and/or central lumen,
   being built-in the wall,
   being sealed to the wall, or
   being connected slidably along the wall.

11. The oral airway device of claim 1, wherein the oral airway device further comprises a dorsal inflatable cuff positioned on the dorsal surface of the tongue.

12. A method for ventilating a patient, the method comprising:
inserting a camera into the camera channel in the oral airway device of claim 1, inserting the assembly of the oral airway device of claim 1 with the camera into the patient's oral cavity under continuous visualization by the camera, and positioning the assembly in the patient's pharynx,
establishing a closed system in the assembly, and
connecting the assembly to a ventilator.

13. The method of claim 12, wherein the method further comprises inserting at least one of a tool and/or suction tube into the oral airway device of claim 1 and wherein the closed system is established by at least one of the following: placing a ventilation adaptor over the wall of the oral airway device of claim 1 and/or inserting the accessory cap in the central lumen of the oral airway device of claim 1.

14. A system for managing airways in a patient, the system comprising:
the oral airway device of claim 1;
a camera insertable and removable from the camera channel; and
a ventilator adaptor with at least one cap for establishing a closed system in the oral airway device.

15. A method for intubating a patient, the method comprising:
a) inserting an endotracheal tube into the central lumen of the oral airway device of claim 1,
b) positioning the assembly of step a) in the patient and inserting the endotracheal tube through the vocal cords under visualization by a camera;
c) separating the endotracheal tube from the oral airway device through the slit; and
d) removing the oral airway device from the patient while the endotracheal tube remains inserted.

16. A method for extubating or exchanging an endotracheal tube in a patient intubated with a first endotracheal tube placed in the oral airway device of claim 1, the method comprising:
a) removing the first endotracheal tube from the patient while the oral airway device remains placed in the patient under continuous visualization from a camera placed in the camera channel of the oral airway device of claim 1; and
b) if the first endotracheal tube should be exchanged, inserting a second endotracheal tube into the central lumen of the oral airway device which is still placed in the patient and placing the second endotracheal tube through the patient's vocal cords under continuous visualization by the camera.

17. An oral airway device comprising a tubal body created by a wall which has a length between a distal end and a proximal end, the tubal body being curved anteriorly, the wall having a dorsal surface and a ventral surface and two flanks, a first flank and a second flank, wherein the oral airway device comprises three channels, a first channel, a second channel and a third channel, wherein the first channel, the second channel and the third channel are laterally aligned, and wherein the second channel and the third channel are hollow passages in the wall along the distal-proximal axis of the wall, each of the two channels opening with a proximal opening at the proximal end of the wall, and each of the channels opening with a distal opening at the distal end of the wall,
wherein the first channel is located peripherally in the first flank and is a groove capable of hosting a bougie, and wherein the groove runs along the proximal-distal axis of the wall and the first channel is not covered by the wall at least on a portion of the ventral surface and/or the first flank of the wall, the first channel opens with a proximal opening at the proximal end of the wall and the first channel opens with a distal opening at the distal end of the wall;
wherein the second channel is located centrally in the oral airway device and second channel is compatible with a camera which can be inserted and removed from the second channel,
and the third channel is located peripherally in the second flank and the third channel is compatible with a camera which can be inserted and removed from the third channel, and
wherein the oral airway device does not comprise an endotracheal lumen.

18. The oral airway device of claim 17, wherein the oral airway device is compatible with a laryngoscope which comprises a blade attached to a handle, and wherein the oral airway device has a holder attached to the ventral surface of the wall, the blade of the laryngoscope being insertable and removable from the holder.

* * * * *